(12) United States Patent
Birkus et al.

(10) Patent No.: US 8,163,718 B2
(45) Date of Patent: Apr. 24, 2012

(54) NUCLEOSIDE ANALOGUES CONTAINING PHOSPHONATE OR PHOSPHONAMIDE GROUPS

(75) Inventors: Gabriel Birkus, San Francisco, CA (US); Adrian S. Ray, Redwood City, CA (US); Daniel B. Tumas, San Carlos, CA (US); William J. Watkins, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 474 days.

(21) Appl. No.: 12/388,789

(22) Filed: Feb. 19, 2009

(65) Prior Publication Data

US 2009/0232768 A1 Sep. 17, 2009

Related U.S. Application Data

(60) Provisional application No. 61/030,148, filed on Feb. 20, 2008.

(51) Int. Cl.
*C07F 9/6561* (2006.01)
*A61K 31/675* (2006.01)
*A61P 31/20* (2006.01)
*A61P 35/00* (2006.01)

(52) U.S. Cl. .................................... 514/81; 544/244
(58) Field of Classification Search ............... 544/244; 514/81
See application file for complete search history.

(56) References Cited

U.S. PATENT DOCUMENTS

| | | | |
|---|---|---|---|
| 5,854,228 A * | 12/1998 | Webb et al. ............... | 514/81 |
| 5,977,061 A | 11/1999 | Holy et al. | |
| 7,553,825 B2 * | 6/2009 | Cheng et al. ............... | 514/81 |
| 2003/0072814 A1 | 4/2003 | Maibach et al. | |
| 2003/0187261 A1 | 10/2003 | Havlicek et al. | |
| 2009/0202484 A1 * | 8/2009 | Chong et al. ............... | 424/85.6 |

FOREIGN PATENT DOCUMENTS

| | | |
|---|---|---|
| CN | 101066981 A | 11/2007 |
| WO | WO-2005/066189 A1 | 7/2005 |
| WO | WO-2008/005555 A1 | 1/2008 |

OTHER PUBLICATIONS

Yu, Journal of Medicinal Chemistry (1992), 35(16), 2958-69.*
Camp, N et al. (1995) "Synthesis of Peptide Analogues Containing Phosphonamidate Methyl Ester Functionality: HIV-1 Proteinase Inhibitors Possessing Unique Cell Uptake Properties," *Bioorganic & Medicinal Chemistry* 3(3):297-312.
Holy, A. et al. (2001) Synthesis and Cytostatic Activity of N-[2-(Phosphonomethoxy)Alkyl] Derivatives of $N^6$-Substituted Adenines, 2,6-Diaminopurines and Related Compounds, *Collect. Czech. Chem. Commun.* 66:1545-1592.
International Search Report and Written Opinion for PCT/US2009/034471, filed Feb. 19, 2009, mailed Aug. 18, 2009.
Extended European Search Report for EP Application No. 11151008.7-1211 mailed Apr. 7, 2011.

* cited by examiner

*Primary Examiner* — Mark Berch
(74) *Attorney, Agent, or Firm* — J. Elin Hartrum; Francis O. Ginah

(57) ABSTRACT

Novel compounds having structure (1)

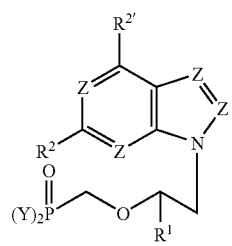

(1)

wherein Z, is N or CH to form a purine, Y, $R^1$, $R^{2'}$ and $R^2$ are defined in the specification, are provided for use in the treatment of tumors and the prophylaxis or treatment of viral infections.

10 Claims, No Drawings

NUCLEOSIDE ANALOGUES CONTAINING PHOSPHONATE OR PHOSPHONAMIDE GROUPS

This application is filed under 35 U.S.C. 111(a) claiming the benefit under 35 U.S.C. 119(e) to provisional application 61/030,148 filed Feb. 20, 2008 which is herein incorporated by reference in its entirety.

Nucleotide analogues containing phosphonate groups are disclosed for example in U.S. Pat. Nos. 4,659,825, 4,808,716, 4,724,233, 5,142,051, 5,302,585, 5,208,221, 5,352,786, 5,356,886, 5,663,159, 5,977,061 and 5,459,256, in EP publication numbers EP 421,819, 434,450, 481,214, 468,119, 269,947, 481,214, 630,381, 369,409, 454,427, 618,214 and 398,231 and in WO 95/07920, 27002808A1, 09526734A1, 94/03467, 94/03467, 95/07920, 07/002,912, 05/066189, 02108241 and 94/03467, CN 101066981, Daluge et al. (34th Interscience Conference on Antimicrobial Agents and Chemotherapy, Oct. 4-7, 1994), Cihlar et al., "Antimicrobial Agents and Chemotherapy" 39(1):117-124 (1995) and Holy et al., "ACS Symp. Ser." 401:57-71 (1989) and Holy, "Kem. Ind." 38(10):457-462 (1989), Naessens et al., "Biochem. Pharmacol." 1999 Jul. 15; 58(2):311-23, Valerianova et al. "Anticancer Res." 2001 May-June; 21(3B):2057-64, Parker W B, Shaddix S C, Rose L M, Pham P T, Hua M, Vince R. Nucleosides Nucleotides Nucleic Acids. 2000 April; 19(4): 795-804, Daluge S M, Good S S, Faletto M B, Miller W H, St Clair M H, Boone L R, Tisdale M, Parry N R, Reardon J E, Dornsife R E, Averett D R, Krenitsky T A. Antimicrob Agents Chemother. 1997 May; 41(5):1082-1093, and WO2007/136650.

This invention in one embodiment is a compound having structure (1)

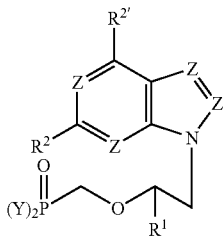

(1)

wherein
Y independently is —OR$^3$; an amino acid, amino acid amide or amino acid ester or amino acid thioester linked through an amino group of the amino acid;
R$^1$ is CH$_3$ or H;
R$^{2'}$ and R$^2$ independently are H, halo, NH$_2$, NH(R$^{10}$), N(R$^{10}$)2 or X, but at least one R$^2$ or R$^{2'}$ is X;
R$^3$ independently is H; unsubstituted aryl, heterocycle, C$_1$-C$_{12}$ alkyl, C$_2$-C$_{12}$ alkenyl or C$_2$-C$_{12}$ alkynyl; or aryl, heterocycle, C$_1$-C$_{12}$ alkyl, C$_2$-C$_{12}$ alkenyl or C$_2$-C$_{12}$ alkynyl substituted by C$_1$-C$_{12}$ alkoxy, halo, carboxyl, carboxylester, hydroxyl, amino, CN, NO$_2$, OH, thiol, thiolester, azido, arylamino, C$_1$-C$_{12}$ haloalkyl (1-6 halogen atoms), C$_2$-C$_{12}$ alkenyl or C$_2$-C$_{12}$ alkynyl;
X is —OR$^{10}$,
R$^{10}$ is unsubstituted C$_1$-C$_{15}$ alkyl, C$_2$-C$_{15}$ alkenyl, C$_6$-C$_{15}$ arylalkenyl, C$_6$-C$_{15}$ arylalkynyl, C$_2$-C$_{15}$ alkynyl, C$_1$-C$_6$-alkylamino-C$_1$-C$_6$ alkyl-, C$_5$-C$_{15}$ aralkyl, C$_6$-C$_{15}$ heteroaralkyl, C$_5$-C$_6$ aryl, C$_2$-C$_6$ heterocycloalkyl;
or R$^{10}$ is C$_2$-C$_{15}$ alkyl, C$_3$-C$_{15}$ alkenyl, C$_6$-C$_{15}$ arylalkenyl, C$_3$-C$_{15}$ alkynyl, C$_7$-C$_{15}$ arylalkynyl, C$_1$-C$_6$-alkylamino-C$_1$-C$_6$ alkyl-, C$_5$-C$_{15}$ aralkyl, C$_6$-C$_{15}$ heteroaralkyl or C$_3$-C$_6$ heterocycloalkyl wherein 1 to 2 methylene groups in the alkyl moiety not adjacent to the oxygen of —OR$^{10}$ have been replaced by —O—, —S— or N(R$^3$);
or one of the foregoing R$^{10}$ groups which is substituted with 1 to 3 of halo, R$^3$, CN or N$_3$;
Z is N or CH, provided that the heterocyclic nucleus varies from purine by no more than one Z;
and therapeutically acceptable salts and/or enriched optical isomers thereof.

In another embodiment, the invention is a compound having structure (1)

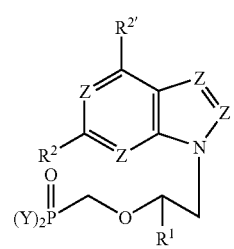

(1)

wherein
Y independently is —OR$^3$; an amino acid, amino acid amide or amino acid ester or amino acid thioester linked through an amino group of the amino acid, or a group of the structure (2)

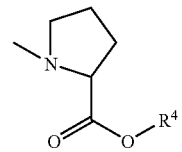

(2)

provided that at least one Y is a group of structure (2);
R$^1$ is CH$_3$ or H;
R$^{2'}$ and R$^2$ independently are H, halo, NH$_2$, NH(R$^{10}$), N(R$^{10}$)$_2$ or X;
R$^3$ independently is H; unsubstituted aryl, heterocycle, C$_1$-C$_{12}$ alkyl, C$_2$-C$_{12}$ alkenyl or C$_2$-C$_{12}$ alkynyl; or aryl, heterocycle, C$_1$-C$_{12}$ alkyl, C$_2$-C$_{12}$ alkenyl or C$_2$-C$_{12}$ alkynyl substituted by C$_1$-C$_{12}$ alkoxy, halo, carboxyl, carboxylester, hydroxyl, amino, CN, NO$_2$, OH, thiol, thiolester, azido, arylamino, C$_1$-C$_{12}$ haloalkyl (1-6 halogen atoms), C$_2$-C$_{12}$ alkenyl or C$_2$-C$_{12}$ alkynyl;
R$^4$ is R$^3$, or OR$^4$ is NH$_2$, NH(R$^{10}$) or N(R$^{10}$)$_2$;
X is —OR$^{10}$,
R$^{10}$ is unsubstituted C$_1$-C$_{15}$ alkyl, C$_2$-C$_{15}$ alkenyl, C$_6$-C$_{15}$ arylalkenyl, C$_6$-C$_{15}$ arylalkynyl, C$_2$-C$_{15}$ alkynyl, C$_1$-C$_6$-alkylamino-C$_1$-C$_6$ alkyl-, C$_5$-C$_{15}$ aralkyl, C$_6$-C$_{15}$ heteroaralkyl, C$_5$-C$_6$ aryl, C$_2$-C$_6$ heterocycloalkyl;
or R$^{10}$ is C$_2$-C$_{15}$ alkyl, C$_3$-C$_{15}$ alkenyl, C$_6$-C$_{15}$ arylalkenyl, C$_3$-C$_{15}$ alkynyl, C$_7$-C$_{15}$ arylalkynyl, C$_1$-C$_6$-alkylamino-C$_1$-C$_6$ alkyl-, C$_5$-C$_{15}$ aralkyl, C$_6$-C$_{15}$ heteroaralkyl or C$_3$-C$_6$ heterocycloalkyl wherein 1 to 2 methylene groups in the alkyl moiety not adjacent to the oxygen of —OR$^{10}$ have been replaced by —O—, —S— or N(R$^3$);
or one of the foregoing R$^{10}$ groups which is substituted with 1 to 3 of halo, R$^3$, CN or N$_3$;
Z is N or CH, provided that the heterocyclic nucleus varies from purine by no more than one Z; and therapeutically acceptable salts and/or enriched optical isomers thereof.

In another embodiment, the present invention provides a compound having structure (3)

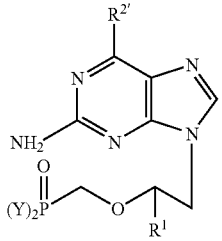

(3)

wherein

Y independently is —OR³; an amino acid, amino acid amide or amino acid ester or amino acid thioester linked through an amino group of the amino acid, R¹ is CH₃ or H;

R²' is —OR¹⁰;

R³ independently is H; unsubstituted aryl, heterocycle, $C_1$-$C_{12}$ alkyl, $C_2$-$C_{12}$ alkenyl or $C_2$-$C_{12}$ alkynyl; or aryl, heterocycle, $C_1$-$C_{12}$ alkyl, $C_2$-$C_{12}$ alkenyl or $C_2$-$C_{12}$ alkynyl substituted by $C_1$-$C_{12}$ alkoxy, halo, carboxyl, carboxylester, hydroxyl, amino, CN, NO₂, OH, thiol, thiolester, azido, arylamino, $C_1$-$C_{12}$ haloalkyl (1-6 halogen atoms), $C_2$-$C_{12}$ alkenyl or $C_2$-$C_{12}$ alkynyl; wherein when R³ is unsubstituted $C_1$-$C_{12}$ alkyl, 1 to 4 methylene groups on R³ not adjacent to the oxygen of —OR³ is optionally replaced by —O— or —S— or —C(O)—;

R¹⁰ is unsubstituted $C_1$-$C_{15}$ alkyl, $C_2$-$C_{15}$ alkenyl, $C_6$-$C_{15}$ arylalkenyl, $C_6$-$C_{15}$ arylalkynyl, $C_2$-$C_{15}$ alkynyl, $C_1$-$C_6$-alkylamino-$C_1$-$C_6$ alkyl-, $C_5$-$C_{15}$ aralkyl, $C_6$-$C_{15}$ heteroaralkyl, $C_5$-$C_6$ aryl, $C_2$-$C_6$ heterocycloalkyl;

or R¹⁰ is $C_1$-$C_{15}$ alkyl, $C_3$-$C_{15}$ alkenyl, $C_6$-$C_{15}$ arylalkenyl, $C_3$-$C_{15}$ alkynyl, $C_6$-$C_{15}$ arylalkynyl, $C_1$-$C_6$-alkylamino-$C_1$-$C_6$ alkyl-, $C_5$-$C_{15}$ aralkyl, $C_6$-$C_{15}$ heteroalkyl or $C_3$-$C_6$ heterocycloalkyl wherein 1 to 2 methylene groups in the alkyl moiety not adjacent to the oxygen of —OR¹⁰ have been replaced by —O—, —S— or N(R³);

or one of the foregoing R¹⁰ groups is substituted with 1 to 3 of halo, R³, CN or N₃;

and therapeutically acceptable salts and/or enriched optical isomers thereof.

In another embodiment, the present invention provides a compound having structure (3), wherein Y independently is —OR³; an amino acid, amino acid amide or amino acid ester or amino acid thioester linked through an amino group of the amino acid, or a group of the structure (2)

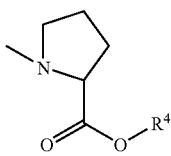

(2)

provided that at least one Y is a group of structure (2);

R¹ is CH₃ or H;

R²' is —OR¹⁰;

R³ independently is H; unsubstituted aryl, heterocycle, $C_1$-$C_{12}$ alkyl, $C_2$-$C_{12}$ alkenyl or $C_2$-$C_{12}$ alkynyl; or aryl, heterocycle, $C_1$-$C_{12}$ alkyl, $C_2$-$C_{12}$ alkenyl or $C_2$-$C_{12}$ alkynyl substituted by $C_1$-$C_{12}$ alkoxy, halo, carboxyl, carboxylester, hydroxyl, amino, CN, NO₂, OH, thiol, thiolester, azido, arylamino, $C_1$-$C_{12}$ haloalkyl (1-6 halogen atoms), $C_2$-$C_{12}$ alkenyl or $C_2$-$C_{12}$ alkynyl; wherein when R³ is unsubstituted $C_1$-$C_{12}$ alkyl, 1 to 4 methylene groups on R³ not adjacent to the oxygen of —OR³ is optionally replaced by —O— or —S— or —C(O)—;

R¹⁰ is unsubstituted $C_1$-$C_{15}$ alkyl, $C_2$-$C_{15}$ alkenyl, $C_6$-$C_{15}$ arylalkenyl, $C_6$-$C_{15}$ arylalkynyl, $C_2$-$C_{15}$ alkynyl, $C_1$-$C_6$-alkylamino-$C_1$-$C_6$ alkyl-, $C_5$-$C_{15}$ aralkyl, $C_6$-$C_{15}$ heteroaralkyl, $C_5$-$C_6$ aryl, $C_2$-$C_6$ heterocycloalkyl;

or R¹⁰ is $C_2$-$C_{15}$ alkyl, $C_3$-$C_{15}$ alkenyl, $C_6$-$C_{15}$ arylalkenyl, $C_3$-$C_{15}$ alkynyl, $C_6$-$C_{15}$ arylalkynyl, $C_1$-$C_6$-alkylamino-$C_1$-$C_6$ alkyl-, $C_5$-$C_{15}$ aralkyl, $C_6$-$C_{15}$ heteroalkyl or $C_3$-$C_6$ heterocycloalkyl wherein 1 to 2 methylene groups in the alkyl moiety not adjacent to the oxygen of —OR¹⁰ have been replaced by —O—, —S— or N(R³);

or one of the foregoing R¹⁰ groups is substituted with 1 to 3 of halo, R³, CN or N₃;

and therapeutically acceptable salts and/or enriched optical isomers thereof.

In another embodiment, the present invention provides a compound having structure (4):

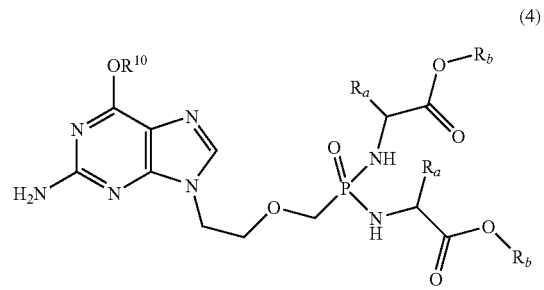

(4)

wherein each Ra independently is $C_1$-$C_6$ alkyl, $C_2$-$C_6$ alkenyl, $C_2$-$C_6$ alkynyl, $C_6$-$C_{10}$ aryl-$C_1$-$C_4$ alkyl-, wherein Ra and the nitrogen on the —NH— optionally form a (5-7) membered ring;

each Rb independently is $C_1$-$C_8$ alkyl, $C_2$-$C_8$ alkenyl, $C_2$-$C_8$ alkynyl, $C_6$-$C_{10}$ aryl-$C_1$-$C_4$ alkyl-;

R¹⁰ is $C_1$-$C_8$ alkyl, or $C_2$-$C_8$ alkenyl, or $C_2$-$C_8$ alkynyl, wherein $C_1$-$C_8$ alkyl is optionally substituted by one $C_1$-$C_4$ alkoxy group, and therapeutically acceptable salts and/or enriched optical isomers thereof.

Preferably, the present invention provides a compound of structure (4), wherein each Ra independently is $C_1$-$C_4$ alkyl, or benzyl, each Rb independently is $C_1$-$C_4$ alkyl, R¹⁰ is $C_1$-$C_8$ alkyl, or $C_2$-$C_8$ alkenyl, or $C_2$-$C_8$ alkynyl, wherein $C_1$-$C_8$ alkyl is optionally substituted by one $C_1$-$C_4$ alkoxy group; and therapeutically acceptable salts and/or enriched optical isomers thereof.

In another embodiment, the present invention provides a compound having structure (5):

(5)

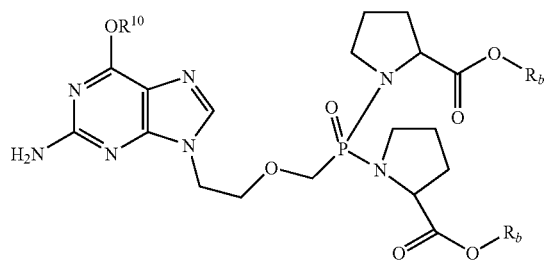

wherein
each Rb independently is $C_1$-$C_8$ alkyl, or $C_2$-$C_8$ alkenyl, or $C_2$-$C_8$ alkynyl, or $C_6$-$C_{10}$ aryl-$C_1$-$C_4$ alkyl-;
$R^{10}$ is $C_1$-$C_8$ alkyl, or $C_2$-$C_8$ alkenyl, or $C_2$-$C_8$ alkynyl, wherein $C_1$-$C_8$ alkyl is optionally substituted by one $C_1$-$C_4$ alkoxy group; and therapeutically acceptable salts and/or enriched optical isomers thereof.

Preferably, the present invention provides a compound of structure (5), wherein each Rb independently is $C_1$-$C_4$ alkyl, or benzyl, $R^{10}$ is $C_1$-$C_4$ alkyl; and therapeutically acceptable salts and/or enriched optical isomers thereof.

In another embodiment, the present invention provides a compound having structure (6):

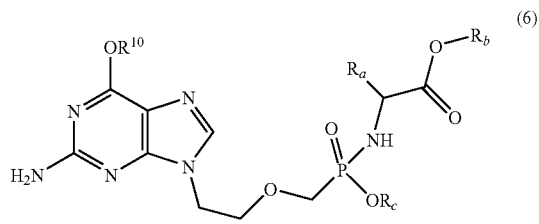

wherein
Ra is $C_1$-$C_4$ alkyl, $C_2$-$C_4$ alkenyl, $C_2$-$C_4$ alkynyl, $C_6$-$C_{10}$ aryl-$C_1$-$C_4$ alkyl-, wherein Ra and the nitrogen on the —NH— optionally form a (5-7) membered ring;
Rb is $C_1$-$C_8$ alkyl, or $C_2$-$C_8$ alkenyl, or $C_2$-$C_8$ alkynyl, or $C_6$-$C_{10}$ aryl-$C_1$-$C_4$ alkyl-,
Rc is $C_6$-$C_{10}$ aryl that is optionally substituted by one or two substituents selected from halogen, cyano, or $C_1$-$C_4$ alkyl;
$R^{10}$ is $C_1$-$C_4$ alkyl; and therapeutically acceptable salts and/or enriched optical isomers thereof.

Preferably, the present invention provides a compound of structure (6), wherein Ra is $C_1$-$C_4$ alkyl or benzyl, Rb is $C_1$-$C_4$ alkyl, Rc is phenyl; and therapeutically acceptable salts and/or enriched optical isomers thereof.

In another embodiment, the present invention provides a compound having structure (7):

(7)

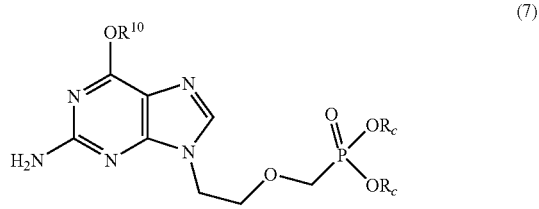

wherein
each Rc independently is $C_1$-$C_4$ alkyl that is substituted by one $C_1$-$C_4$ alkyl-O—C(O)—O— group; $R^{10}$ is $C_1$-$C_4$ alkyl; and therapeutically acceptable salts and/or enriched optical isomers thereof.

In another embodiment, the present invention provides a compound having structure (8);

(8)

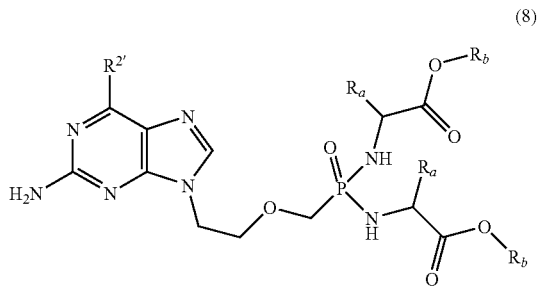

wherein $R^{2'}$ is $C_4$-$C_7$ cycloalkyl-NH—; each Ra independently is $C_1$-$C_4$ alkyl, $C_2$-$C_4$ alkenyl, $C_2$-$C_4$ alkynyl, wherein Ra and the nitrogen on the —NH— optionally form a (5-7) membered ring; each Rb independently is $C_1$-$C_8$ alkyl, or $C_2$-$C_8$ alkenyl, or $C_2$-$C_8$ alkynyl, or $C_6$-$C_{10}$ aryl$C_1$-$C_4$ alkyl-; and therapeutically acceptable salts and/or enriched optical isomers thereof.

In another embodiment, the present invention provides a compound having structure (9);

(9)

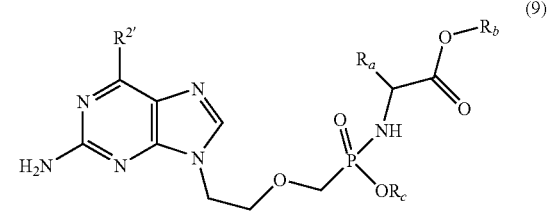

wherein $R^{2'}$ is $C_4$-$C_7$ cycloalkyl-NH—; each Ra independently is $C_1$-$C_4$ alkyl, $C_2$-$C_4$ alkenyl, $C_2$-$C_4$ alkynyl, wherein Ra and the nitrogen on the —NH— optionally form a (5-7) membered ring; Rb is $C_1$-$C_8$ alkyl, or $C_2$-$C_8$ alkenyl, or $C_2$-$C_8$ alkynyl, or $C_6$-$C_{10}$ aryl-$C_1$-$C_4$ alkyl-; Rc is Rc is $C_6$-$C_{10}$ aryl that is optionally substituted by one or two substituents selected from halogen, cyano, or $C_1$-$C_4$ alkyl; and therapeutically acceptable salts and/or enriched optical isomers thereof.

In another embodiment, the present invention provides a compound having structure (10):

(10)

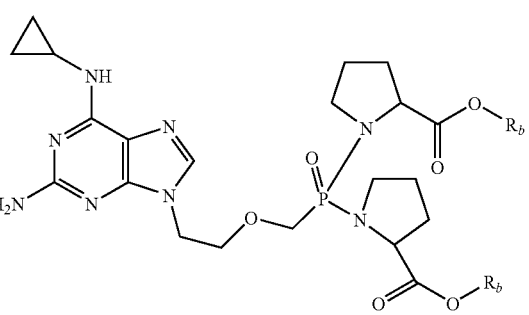

wherein Rb independently is $C_1$-$C_8$ alkyl, or $C_2$-$C_8$ alkenyl, or $C_2$-$C_8$ alkynyl, or $C_6$-$C_{10}$ aryl-$C_1$-$C_4$ alkyl-; and therapeutically acceptable salts and/or enriched optical isomers thereof.
Preferably, Rb is $C_1$-$C_4$ alkyl.

Other embodiments of the invention include compound (1) in combination with a pharmaceutically acceptable carrier, the use of said compound in the treatment of malignancies or for the prophylaxis or therapy of viral infections, and the combination of compound (1) with other antiviral or antitumor agents.

The present invention provides for compounds of formula I, pharmaceutical compositions employing such compounds and for methods of using such compounds. For purposes of interpreting this specification, the following definitions will apply and whenever appropriate, terms used in the singular will also include the plural and vice versa.

As used herein, and unless modified by the immediate context:

Alkyl means $C_1$-$C_{15}$ branched, normal or cyclic saturated hydrocarbons. Preferably, the alkyl comprises 1 to 8 carbon atoms, or 1 to 6 carbon atoms, or 1 to 4 carbon atoms. Representative examples of alkyl include, but are not limited to, methyl, ethyl, propyl, cyclopropyl, cyclobutyl, isopropyl, n-, sec-, iso- and tert-butyl, pentyl, isopentyl, 1-methylbutyl, 1-ethylpropyl, neopentyl, and t-pentyl, n-hexyl, 3-methylhexyl, 2,2-dimethylpentyl, 2,3-dimethylpentyl, n-heptyl, n-octyl, n-nonyl, n-decyl and the like.

Alkenyl means $C_2$-$C_{15}$ branched, normal or cyclic hydrocarbons containing at least 1 (generally 1-3) cis or trans oriented conjugated or unconjugated double bond, including allyl, ethenyl, propenyl, isopropenyl, 1-, 2- and 3-butenyl, 1- and 2-isobutenyl and the like.

Alkynyl means $C_2$-$C_{15}$ branched, normal, or cyclic hydrocarbon bearing at least 1 (generally 1-3) triple bond, e.g., 2-propynyl.

Alkoxy means alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having 1-7 carbons and preferably 1-4 carbons.

As used herein, the term "halo" or "halogen" refers to fluoro, chloro, bromo, and iodo.

Haloalkyl means alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

Alkylamino means alkyl-NH—, wherein alkyl is defined herein.

Heteroalkyl means a straight or branched chain hydrocarbon radical, or combinations thereof, consisting of the stated number of carbon atoms and from one to three heteroatoms selected from C, N, Si, and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "aryl" refers to monocyclic or bicyclic aromatic hydrocarbon groups having 6-14 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C(O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, aryl means an aromatic substituent containing only carbon ring atoms which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine. Arylamino means aryl-$NH_2$—.

Aralkyl means aryl-alkyl-, wherein aryl and alkyl are defined herein.

Aralkenyl means aryl-alkenyl-, wherein aryl and alkenyl are defined herein.

Aralkynyl means aryl-alkynyl-, wherein aryl and alkynyl are defined herein.

Cycloalkyl means saturated, monocyclic or bicyclic hydrocarbon rings, generally having a specified number of carbon atoms that comprise the ring (i.e., $C_3$-$C_7$ cycloalkyl refers to a cycloalkyl group having 3, 4, 5, 6 or 7 carbon atoms as ring members). The cycloalkyl may be attached to a group or to a substrate at any ring atom, unless such attachment would violate valence requirements.

Heteroaryl means 5-14 membered monocyclic- or bicyclic- or fused polycyclic-ring system that is aromatic, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl. The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoquinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, 1-3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo

[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. A heteroaryl group may be mono-, bi-, tri-, or polycyclic, preferably mono-, bi-, or tricyclic, more preferably mono- or bicyclic.

Heteroaralkyl means heteroaryl-alkyl-, wherein both heteroaryl and alkyl are defined herein.

Heterocycle or heterocyclo means an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1, 4-trioxo-1,2,5-thiadiazolidin-2-yl and the like.

Exemplary bicyclic heterocyclic groups include indolyl, dihydroindolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

Heterocycloalkyl means any fully saturated alkyl group forming a ring having $C_3$-$C_7$ in which 1 to 3 $CH_2$ groups have been substituted with N(R), O or S. Heterocycloalkyl includes the saturated counterparts of heteroaryl groups, and non-limiting examples include for example piperazinyl, morpholino, aziridinyl, pyrrolidinyl, imidazolidinyl, pyrazolidinyl, piperidinyl, tetrahydrofuranyl.

Isomer refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (-) depending on the direction (dextro- or levorotatory) which they rotate plane-polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

A pharmaceutically acceptable carrier includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

As used herein, the term "pharmaceutically acceptable carrier/excipient" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces proliferation of cancer cells, or inhibiting or reducing tumor/cancer growth in vitro or in vivo, or inhibiting or reducing a neoplastic disease in a subject such as a mammal. In another preferred embodiment, it also refers to the amount that reduces the primary tumor/cancer size, inhibits cancer cell infiltration into peripheral organs, slows or stops tumor metastasis, or relieves at least to some extent one or more symptoms associated with tumor or cancer, etc.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary,* (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. In one embodiment, it refers to ability to cause reduction of a tumor or cancer growth, or reduction of the tumor or cancer size.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value failing within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Alkaryl, alkenylaryl, alkynylaryl, arylalkyl, arylalkynyl, or aralkenyl means alkyl, alkynyl or alkenyl substituted with at least 1 (generally 1-3) aryl groups, or aryl substituted with at least 1 (generally 1-3) alkyl, alkynyl or alkenyl groups.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis (Z)- or trans (E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the hydroxamide or sulfonamide moiety may thus be employed to resolve the compounds of the present invention into their optical antipodes, e.g., by fractional crystallization of a metal (e.g., $Zn^{2+}$) complex formed with an optically active co-ligand, e.g., L- or D-histidine. Racemic products can also be resolved by chiral chromatography, e.g., high pressure liquid chromatography (HPLC) using a chiral adsorbent.

Finally, compounds of the present invention are either obtained in the free form, as a salt thereof.

When a basic group is present in the compounds of the present invention (such as in a substituent group), the compounds can be converted into acid addition salts thereof, preferably pharmaceutically acceptable salts thereof. These may be formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$) alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$) alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, such as calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids such as arginine, lysine and the like. Salts may be formed using conventional methods, advantageously in the presence of an ethereal or alcoholic solvent, such as a lower alkanol. From the solutions of the latter, the salts may be precipitated with diethyl ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

Furthermore, the compounds of the present invention, including their salts, can also be obtained in the form of their hydrates, or include other solvents used for their crystallization.

$R^1$ typically is H, where $R^1$ is not H, $R^1$ typically is in (R) configuration.

$R^2$ and $R^{2'}$ are usually X, H or $NH_2$, but typically at least one of $R^{2'}$ or $R^2$ is X. In some embodiments, both of $R^{2'}$ and $R^2$ are X, which then may be the same or different, but in general only 1 $R^2$ or $R^{2'}$ is X. Ordinarily, X is found at the 6 position and the 2-position is substituted with $NH_2$ or H. $R^2$ or $R^{2'}$ also are halo such as chloro or bromo, whereupon in some embodiments the other $R^2$ or $R^{2'}$ is X. The halo compounds are particularly useful as intermediates.

Preferably $R^2$ is amino.

The ester-forming groups herein, including $R^3$, may vary widely. They include $C_3$-$C_6$ aryl (including phenyl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl), $C_3$-$C_6$ aryl substituted with halo, alkyl $C_1$-$C_{12}$ alkoxy, CN, $NO_2$, OH, carboxy, carboxyester, thiol, thiolester, $C_1$-$C_{12}$ haloalkyl (1-6 halogen atoms), $C_2$-$C_{12}$ alkenyl or $C_2$-$C_{12}$ alkynyl [including 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl], 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, —$C_6H_4$—C(O)—O alkyl $C_1$-$C_5$, ($C_1$-$C_4$ alkyl, including 2-, 3- and 4-ethylsalicylphenyl), 2-, 3- and 4-acetylphenyl, 1,8-dihydroxynaphthyl (—O—$C_{10}H_6$—OH) and aryloxyethyl [$C_6$-$C_9$ aryl (including phenoxyethyl)], 2,2'-dihydroxybiphenyl, alkoxyethyl [$C_1$-$C_6$ alkyl including —$CH_2$—$CH_2$—O—$CH_3$ (2-methoxyethyl)], alkyl substituted by OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4$—$CH_3$, —$(CH_2)_5CH_3$, —$CH_2CH_2F$, —$CH_2CH_2Cl$, —$CH_2CF_3$, and —$CH_2CCl_3$), 2-, 3- and 4-N,N-dialkylaminophenyl, —$C_6H_4CH_2$—$N(CH_3)_2$,

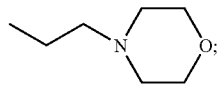

—N-2-propylmorpholino, 2,3-dihydro-6-hydroxyindene, sesamol, catechol monoester, —$CH_2$—C(O)—$N(R^{11})_2$ wherein each $R^{11}$ is the same or different H or $C_1$-$C_4$ alkyl, —$CH_2$—S(O)($R^{11}$), —$CH_2$—$S(O)_2(R^{11})$, —$CH_2$—CH(OC (O)$CH_2R^{11}$)—$CH_2(OC(O)CH_2R^{11})$, cholesteryl, a 5 or 6 carbon monosaccharide, disaccharide or oligosaccharide (3 to 9 monosaccharide residues), enolpyruvate (HOOC—C (=$CH_2$)O), glycerol, alpha-D-beta-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids), trimethoxybenzyl, triethoxybenzyl, 2-alkylpyridinyl ($C_{1-4}$ alkyl),

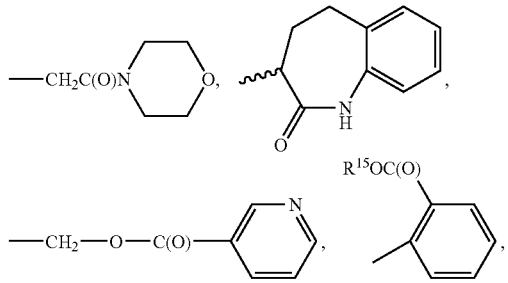

$C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2$—$CCl_3$), $C_1$-$C_{12}$ alkyl (including methyl and ethyl), $C_2$-$C_{12}$ alkenyl or $C_2$-$C_{12}$ alkynyl, and other compounds set forth in Table 1a below. The hydroxyl groups of the compounds herein optionally are substituted with one of groups III, IV or V disclosed in WO94/21604.

$R^4$ is $R^3$, or $OR^4$ is $NH_2$, $NH(R^{10})$, or $N(R^{10})_2$, but typically substitution at this site is $R^3$. An amino acid amide is an amino acid having its carboxyl group(s) substituted by $NH_2$, $NH(R^{10})$, or $N(R^{10})_2$. In general, the amino acids are the known naturally occurring amino acids found as protein constituents in nature.

Typically, $R^{10}$ is relatively small, on the order of 1 to 6 carbon atoms and 0 to 1 N and optionally an S or O atom. The heteroatom is usually O. Ordinarily the heteroatom(s)present in $R^{10}$ is located within the carbon backbone, and not in the terminus distal to the reminder of the molecule, $R^{10}$ generally is not a hydroxyl protecting group such as benzyl. Ordinarily, $R^{10}$ is $C_1$-$C_6$ alkyl; $C_3$-$C_6$ cycloalkyl or $C_3$-$C_4$ cycloalkyl; $C_3$-$C_4$ cycloalkyl-substituted $C_1$-$C_2$ alkyl; $C_3$-$C_4$ cycloalkyl which is mono-, di- or tri-substituted with $C_1$-$C_3$ alkyl; —CH(Phe)$_2$; allyl; $C_1$-$C_6$ alkyl —O—$C_1$-$C_6$ alkyl, or $C_3$-$C_6$ alkyl —O—$C_3$-$C_6$ alkyl, or allyl, in each instance optionally 1 or 2H atoms are substituted with $C_1$-$C_3$ alkyl. $R^{10}$ is n-, s- or cyclo-propyl, n-, s-, t- or cyclo-butyl, n-, s-, t- or cyclo-pentyl, n-, s-, t- or cyclo-hexyl.

$R^{10}$ includes

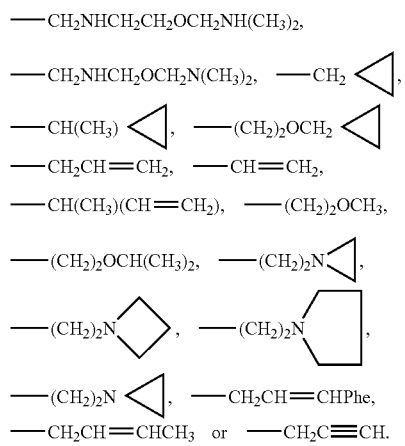

Hydrogen atoms of $R^{10}$ groups, particularly those described in the preceding two paragraphs, and especially alkyl or alkene, in turn are optionally substituted with 1 to 3 of any of halogen (especially F), cyano or azido, or combinations thereof. Typical embodiments include —CH$_2$F, —CH$_2$CN, —(CH$_2$)$_2$N$_3$, —(CH$_2$)$_2$CH$_2$F, —CH$_2$N$_3$, —CH$_2$ (fluorocyclopropyl), —CHFCH$_3$ or —(CH$_2$)$_2$NH(CH$_3$) (CH$_2$F).

$R^{10}$ groups may bear chiral N or C atoms. These are suitably used as the racemic or diastereomeric mixtures, or they may be chirally pure. In general, it is preferred that they be chirally pure.

When $R^1$ is $CH_3$ the compound is the (R) diastereomer, in accord with the understanding in the art that this diastereomer is more antivirally active than the (S) diastereomer. The (R) isomer typically is chirally enriched or isolated. For antitumor compounds of structure (1), $R^1$ is usually H.

Z usually is selected in order to produce a purine nucleus, although optionally it is chosen in order to yield an aza or deaza (monoaza or monodeaza) purine nucleus such as 1-deaza, 3-deaza, 8-aza or 7-deaza.

Y typically will be a group of structure II. The other Y then optionally is $OR^3$. It also optionally is another non-prolyl amino acid or amino acid ester or amino acid amide. When Y is an amino acid (including structure II, which is a proline residue) the amino acid carboxyl group generally is esterified. It also optionally is an amide (where $OR^4$ is amino or $R^{10}$ substituted amino). The amino acid ester or the Y group ester typically is $R^3$. The amino acid esters typically are $C_1$-$C_6$ alkyl, while the Y groups as esters are usually phenyl.

The compounds of the present invention are useful in inhibiting tumor/cancer cell growth or cell proliferation in tumor/cancer cells, slowing down cell cycle progression in tumor/cancer cells. In addition, the compounds of the present invention induce apoptosis. Induction of apoptosis has been used as an important chemotherapy approach in treating cancer/tumor. Accordingly, the compounds of the present invention have valuable pharmaceutical properties, and they can be useful as anti-proliferation and anti-tumor/anti-cancer agents.

Therefore, in one aspect, the compounds of the present invention can be used for inhibiting cell proliferation both in vitro and in vivo. In one embodiment, the compounds of the present invention can used to inhibit cell proliferation in a tumor/cancer cell by contacting the tumor/cancer cell with an effective amount of said compounds. In one embodiment, the compounds of the present invention can be used to treat cellular proliferation diseases or conditions. Said diseases can include, but are not limited to, cancer, autoimmune disease, fungal disorders, arthritis, graft rejection, inflammatory bowel disease, cellular proliferation induced after medical procedures, including, but not limited to, surgery, angioplasty, and the like.

In another aspect, the compounds of the present invention can be used for inhibiting tumor/cancer growth both in vitro and in vivo. In one embodiment, the compounds can be used for inhibiting tumor/cancer cell growth by contacting the tumor/cancer cell with an effective amount of said compounds. In one embodiment, the invention provides a method of using the compounds of the present invention for inhibiting tumor or cancer growth. Tumors or cancers that are treatable according to the methods include, for example, hematological malignancies such as leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia and the like, tumors or cancers located in the breast, lung, thyroid, lymph node, genitourinary system, kidney, ureter, bladder, ovary, testis, prostate, musculoskeletal system, bone, skeletal muscle, bone marrow, gastrointestinal tract, stomach, esophagus, small bowel, colon, rectum, pancreas, liver, smooth muscle, central or peripheral nervous system, brain, spinal cord, nerves, head, neck, ear, eye, nasopharynx, oropharynx, salivary gland, cardiovascular system, oral cavity, tongue, larynx, hypopharynx, soft tissues, skin, cervix, anus, retina, and/or heart of a mammal.

In one embodiment the invention provides a method of using the compounds of the present invention to treat a neoplastic disease, or a tumor/cancer. As used herein, the term "neoplastic disease" refers to any abnormal growth of cells or tissues being either benign (non-cancerous) or malignant (cancerous). Neoplastic diseases that are treatable according to the methods of the invention include, for example, neoplasms from acute myelogenous leukemia, chronic lymphocytic leukemia, chronic myelogenous leukemia, cutaneous T-cell lymphoma, hairy-cell leukemia and non-Hodgkin's lymphoma.

The compounds of this invention are useful in the treatment of cancer or tumors (including dysplasias such as uterine dysplasia). These includes hematological malignancies, oral carcinomas (for example of the lip, tongue or pharynx), digestive organs (for example esophagus, stomach, small intestine, colon, large intestine, or rectum), liver and biliary passages, pancreas, respiratory system such as larynx or lung (small cell and non-small cell), bone, connective tissue, skin (e.g., melanoma), breast, reproductive organs (uterus, cervix, testicles, ovary, or prostate), urinary tract (e.g., bladder or kidney), brain and endocrine glands such as the thyroid. In summary, the compounds of this invention are employed to treat any neoplasm, including not only hematologic malignancies but also solid tumors of all kinds.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be sub-divided into Hodgkin's Disease and Non-Hodgkin's lymphoma (NHL). The later group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

Additionally, the present invention provides:
a compound of the present invention for use as a medicament;
use of a compound of the present invention for the preparation of a medicament for inhibiting cell proliferation in tumor/cancer cells, or slowing down cell cycle progression in tumor/cancer cells;
use of a compound of the present invention for the preparation of a medicament for treating cellular proliferation diseases or conditions;
use of a compound of the present invention for the preparation of a medicament for inhibiting tumor/cancer growth both in vitro and in vivo;
use of a compound of the present invention for the preparation of a medicament for treating a neoplastic disease.
use of a compound of the present invention for the preparation of a medicament for treating a tumor or cancer,
use of a compound of the present invention for the preparation of a medicament for treating hematological malignancies.

The compounds of this invention also are suitable for the treatment or prophylaxis of viral infections, including DNA viruses and RNA viruses, in particular HSV and HIV. The viruses to be treated will depend upon the antiviral activity of the underlying parent drug. For instance, compounds of the PME series are useful against both DNA and retroviruses, while the PMP compounds are effective against retroviruses.

Exemplary viral infections include infections caused by DNA or RNA viruses including herpesviruses (CMV, HSV 1, HSV 2, EBV, varicella zoster virus [VZV], bovid herpesvirus type 1, equid herpesvirus type 1, HHV-6, papillomaviruses (HPV types 1-55 including carcinogenic HPV), flaviviruses (including yellow fever virus, African swine fever virus and Japanese encephalitis virus), togaviruses (including Venezuelan equine encephalomyelitis virus), influenza viruses (types A-C), retroviruses (HIV-1, HIV-2, HTLV-1, HTLV-II, SIV, FeLV, FIV, MoMSV), adenoviruses (types 1-8), poxviruses (vaccinia virus), enteroviruses (poliovirus types 1-3, Coxsackie, hepatitis A virus, and ECHO virus), gastroenteritis viruses (Norwalk viruses, rotaviruses), hantaviruses (Hantaan virus), polyomavirus, papovaviruses, rhinoviruses, parainfluenza virus types 1-4, rabies virus, and respiratory synctial virus (RSV).

Therefore, the present invention provides use of a compound of the present invention for the preparation of a medicament for viral infections.

The therapeutically useful compounds of this invention are useful in oral or sustained release forms. In these uses an ester or other group is removed in vivo, e.g., hydrolyzed or oxidized, so as to yield for example a free amino or hydroxyl group. Suitable protecting or precursor esters or amidates are selected based on the substrate specificity of esterases and/or peptidases expected to be found within cells where precursor hydrolysis is desired. To the extent that the specificity of these enzymes is unknown, one will screen a plurality of nucleotide analogues of this invention until the desired substrate specificity is found. This will be apparent from the appearance of free phosphonate or of antitumor or antiviral activity. One generally selects compounds that are (i) not hydrolyzed or hydrolyzed comparatively slowly in the upper gut, (ii) gut and cell permeable and (iii) hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, optionally are treated with a precursor that is hydrolyzed at substantially the same rate and to substantially the same degree in all tissues. Assays known in the art are suitable for these purposes, including intestinal lumen stability, cell permeation, liver homogenate stability and plasma stability assays. These assays are used to determine the bioavailability characteristics of the precursors. However, even if the derivatives are not converted in vivo they remain useful as chemical intermediates.

Compounds herein and their physiologically acceptable salts (hereafter collectively referred to as the active ingredients) are formulated for administration by any route appropriate to the condition to be treated. The compounds and formulations preferably will be sterile.

The active ingredients are placed into pharmaceutical formulations. The formulations, both for veterinary and for human use, comprise at least one active ingredient, as above defined, together with one or more acceptable carriers and optionally other therapeutic ingredients. The carrier(s) must be "acceptable" in the sense of being compatible with the other ingredients of the formulation and not deleterious to the recipient.

The formulations conveniently are presented in unit dosage form and may be prepared by any of the methods well known in the art of pharmacy. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

For external infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), typically 0.2 to 15% w/w and most typically 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The oily phase of the emulsions of this invention may be constituted from known ingredients in a known manner. This phase may comprise an emulsifier alone, or a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate. Suitable oils or fats include straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate or 2-ethylhexyl palmitate. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is typically is present in such formulations in a concentration of 0.01 to 20% by weight.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by rapid inhalation through the nasal passage from a container of the powder. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

The present invention further provides veterinary compositions comprising at least one active ingredient as above defined together with a veterinary carrier therefor. Veterinary carriers are materials for administering the composition and may be solid, liquid or gaseous materials which are otherwise inert or acceptable in the veterinary art and are compatible with the active ingredient. These veterinary compositions may be administered orally, parenterally or by any other desired route.

Compounds herein optionally are used in controlled release pharmaceutical formulations containing as active ingredient one or more active compounds in which the release of the active ingredient is controlled and regulated to allow less frequent dosing or to improve the pharmacokinetic or toxicity profile of a given compound. In general, the compounds are administered from controlled release systems such as the intravitreous implant of WO 92/14450 or U.S. Pat. No. 5,098,443, or the matrices of U.S. Pat. No. 4,740,365 or U.S. Pat. No. 5,141,752. Many others are known and are suitable for use herein.

Additionally, the present invention provides:
  a composition of the present invention for use as a medicament;
  use of a composition of the present invention for the preparation of a medicament for inhibiting cell proliferation in tumor/cancer cells, or slowing down cell cycle progression in tumor/cancer cells;
  use of a composition of the present invention for the preparation of a medicament for treating cellular proliferation diseases or conditions;
  use of a composition of the present invention for the preparation of a medicament for inhibiting tumor/cancer growth both in vitro and in vivo;
  use of a composition of the present invention for the preparation of a medicament for treating a neoplastic disease.
  use of a composition of the present invention for the preparation of a medicament for treating a tumor or cancer.
  Use of a composition of the present invention for the preparation of a medicament for treating a viral infection.

Suitable routes for administration include oral, rectal, nasal, topical (including ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

For each of the above-indicated therapeutic indications the amount required of an active ingredient (as above defined) will depend upon a number of factors including whether the use is anti-tumor or anti-viral, the severity of the condition to be treated, the infectious agent, whether the use is prophylactic or to treat an acute infection, the site of infection or tumor (e.g. CMV retinitis is treated systemically or by intravitreous injection, or in the treatment of HHV-6 in multiple sclerosis patients, optionally by intrathecal administration) and other factors ultimately at the discretion of the attending physician or veterinarian. In general, however, a suitable dose for consideration by the clinician will be in the range of analogous methoxyphosphonates (see supra), taking into account differences in potency, generally 0.1 to 250 mg per kilogram bodyweight of recipient per dose (including active ingredient(s) in a range between 0.1 mg and 250 mg/Kg/dose in increments of 0.5 mg/Kg/dose such as 2.5 mg/Kg/dose, 3.0 mg/Kg/dose, 3.5 mg/Kg/dose, etc), typically in the range 0.5 to 50 mg per kilogram body weight per dose and most usually in the range 1 to 15 mg per kilogram body weight per dose.

The desired dose is administered at appropriate intervals in unit dosage forms, usually with a relatively higher induction dose and lower, less frequent maintenance doses. In the case of viral infections, the compounds also are used prophylactically, for example, by administration on about from 1 to 7 days before viral infection. HPV tumors or growths and herpes lesions often are treated topically, either by local injection or by topical gels, ointments or the like.

The compounds of the invention optionally are employed in combination with one, two, or more other therapeutic agents for the treatment or prophylaxis of the infections or tumors indicated above. Examples of such further therapeutic agents include agents that are effective for the treatment or prophylaxis of viral infections or for treatment of tumors and related conditions.

Other therapeutic agents include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chloro-2'-deoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-beta-D-arabinosyl)-5-iodocytidine (FIAC), tetrahydroimidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, valacyclovir, penciclovir, famciclovir, ganciclovir, acyclic nucleotides such as HPMPC, PMEA, PMEG, PMPA, PMPDAP, FPMPA, HPMPA and HPMPDAP, (2R,5R)-9-[tetrahydro-5-(phosphonomethoxy)-2-furanyl]adenine, (2R,5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), cytokines including TNF and TGF-beta, interferons including IFN-alpha, IFN-beta and IFN-gamma, interleukins including interleukin 1, 2, 3, 4, 5, 6, 7, 8, 10, 12, 13, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and, particularly in treatment of HIV, cotherapy with IFN-alpha, IL-2 or IL-12.

Additionally, other therapeutic agents are anti-tumor/cancer agents that are selected from antineoplasts including, e.g., adjuncts (e.g., levamisole, gallium nitrate, granisetron, sargramostim strontium-89 chloride, filgrastim, pilocarpine, dexrazoxane, and ondansetron); androgen inhibitors (e.g., flutamide and leuprolide acetate); antibiotic derivatives (e.g., doxorubicin, bleomycin sulfate, daunorubicin, dactinomycin, and idarubicin); antiestrogens (e.g., tamoxifen citrate, analogs thereof, and nonsteroidal antiestrogens such as toremifene, droloxifene and roloxifene); antimetabolites (e.g., fludarabine phosphate, interferon alfa-2b recombinant, methotrexate sodium, plicamycin, mercaptopurine, and thioguanine); cytotoxic agents (e.g., doxorubicin, carmustine [BCNU], lomustine [CCNU], cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozocin); hormones (e.g., medroxyprogesterone acetate, estradiol, megestrol acetate, octreotide acetate, diethylstilbestrol diphosphate, testolactone, and goserelin acetate); immunomodulators (e.g., aldesleukin); nitrogen mustard derivatives (e.g., melphalan, chlorambucil, mechlorethamine, and thiotepa) and steroids (betamethasone sodium phosphate and betamethasone acetate) and the like.

Other therapeutic agents further include the following anti-cancer agents: abarelix (Plenaxis Depot®); aldesleukin (Prokine®), Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycinD (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); folvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®);

hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine-CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); vairubicin (Valstar®); vinblastine (Velban®); vincristine (Oncovin®); vinorelbine (Navelbine®); and zoledronate (Zometa®).

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

To the extent any compound of this invention cannot be produced/synthesized by the methods analogous to those set forth in the examples below, other methods will be apparent to the artisan. See for instance Liotta et al. "Compendium of Organic Synthesis Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; March, J., "Advanced Organic Chemistry, Third Edition", (John Wiley & Sons, New York, 1985); as well as "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

The synthesis of the 6-alkoxypurine derivatives of this invention is conveniently achieved by the displacement of a leaving group at the 6-position with the phosphonic acid protected in a suitable fashion.

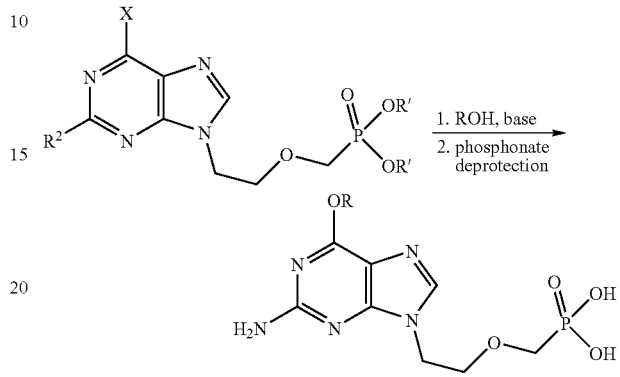

Thus, heating a [2-(2-Amino-6-halo-purin-9-yl)-ethoxymethyl]-phosphonic acid dialkyl ester such as that described in patent application WO2005/066189 together with a suitable alcohol in the presence of a base typically used to generate the alkoxide, such as sodium hydride, sodium hexamethyldisilazide, cesium carbonate, or potassium t-butoxide, optionally in a solvent such as tetrahydrofuran, dimethoxyethane or dimethylformamide, provides the desired 6-alkoxypurine intermediate. This transformation may be facilitated by microwave irradiation. Removal of the protecting groups of the phosphonic acid is conveniently achieved, in this case, by dealkylation with a reagent such as bromotrimethyl silane or iodotrimethylsilane, optionally in the presence of an acid and cation scavenger such as a lutidine derivative and/or an aprotic solvent, at temperatures typically, but not necessarily, below ambient. It will be apparent to the artisan that other phosphonic acid protecting groups such as (but not limited to) benzyl or p-methoxybenzyl esters may also be of utility for this purpose, being removed by typical methods such as hydrogenation or treatment with oxidizing agents or strong acids.

The phosphonic diamides of this invention are typically generated by activation of the corresponding phosphonic acids with a coupling reagent, followed by condensation with the desired amine nucleophile.

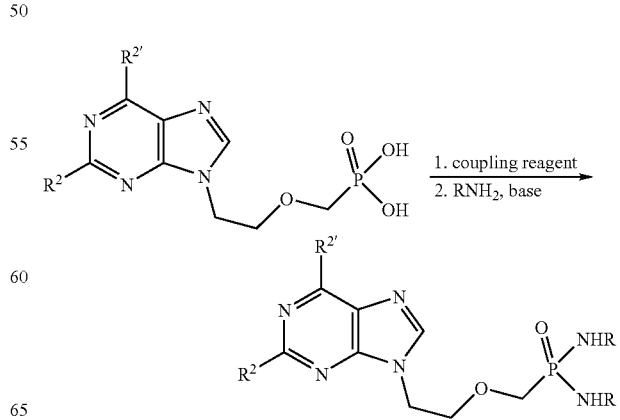

Suitable coupling reagents include those often used in peptide bond formation such as dicyclohexylcarbodiimide or PyBOP, as well as 2,2'-dipyridyl disulfide in combination with triphenylphosphine, in the presence of an organic base such as a trialkylamine, pyridine or lutidine and optionally in an inert solvent such as DMF. The reaction may be facilitated by heating in an inert atmosphere.

These methods are also useful for the synthesis of phosphonic acid monoarylester monoamides of this invention. These are conveniently obtained under similar conditions but with the addition of the desired alcohol to form the ester bond. Alternatively they are accessible from the requisite phosphonic acid diester, following saponification to the monoester by treatment with a reagent such as an alkali metal hydroxide in an ethereal solvent such as THF; the monoester is subjected to the coupling conditions described above to form the desired phosphonamide.

Phosphonic acid diesters of this invention may be synthesized by alkylation of the corresponding phosphonic acids.

EXAMPLES

Silica gel chromatography was performed utilizing Teledyne ISCO chromatography systems and 12 g columns, with dichloromethane and 50% methanol in dichloromethane as solvents A and B respectively. Typical gradient elution was from 0% to 30% B over 55 column volumes, but was varied slightly to optimize each individual separation.

Analytical HPLC chromatography was performed using a Phenomenex Gemini 5 µM $C_{18}$ 4.6×50 mm column, with 1% acetonitrile/0.05% formic acid in water as solvent A and 1% water/0.05% formic acid in acetonitrile as solvent B. Gradient elution was from 5% to 100% B in 2.5 minutes, with additional 1 minute at 100% B for a total run time of 3.5 minutes. MS data were collected using electrospray (ESI) ionization in a ThermoFinnigan detector.

Preparative HPLC chromatography was performed using a Phenomenex Synergi 4 µM Hydro Combi-HTS 30×150 mm column, with water as solvent A and acetonitrile as solvent B. Typical gradient elution was from 2% to 80% B over 20 minutes, but was varied slightly to optimize each individual separation.

Example 1

[2-(2-Amino-6-propoxy-purin-9-yl)-ethoxymethyl]-phosphonic acid (1)

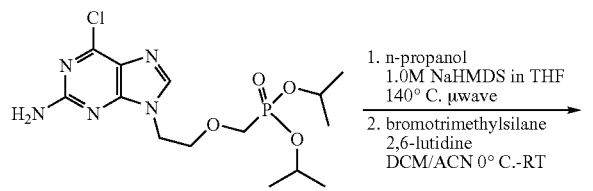

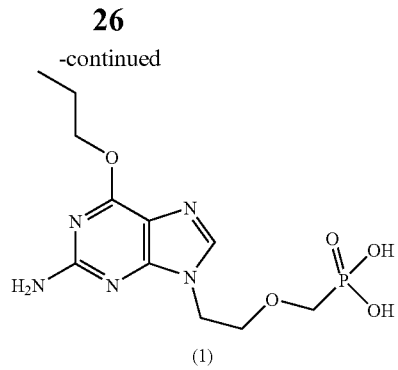

(1) CAS #183194-25-4, [[2-(2-amino-6-chloro-9H-purin-9-yl)ethoxy]methyl]-phosphonic acid, bis(1-methylethyl) ester, was prepared as described in patent WO2005/066189.

An aliquot of n-propanol (7 mL, 93 mmol) was purged with $N_2$ and then cooled in an ice/water bath to 0° C. Sodium hexamethyldisilazide (as 1.0M THF solution, 8 mL, 8 mmol, 5 eq.) was added dropwise and the solution was then stirred 30 minutes. This solution was then added to a 20 mL microwave vial containing Phosphonic acid, P-[[2-(2-amino-6-chloro-9H-purin-9-yl)ethoxy]methyl]-, bis(1-methylethyl)ester 1(625 mg, 1.6 mmol, 1 eq.), and the mixture was heated by microwave to 140° C. for 20 minutes. The mixture was then poured into a flask, evaporated to a solid, and left on high vacuum overnight. Dichloromethane and acetonitrile (8 mL of each) were then added to the flask, and the reaction mixture was again cooled in an ice water bath to 0° C. 2,6-Lutidine (3.7 mL, 32 mmol, 20 eq.) was added to the flask, and then bromotrimethylsilane (3.1 mL, 24 mmol, 15 eq.) was added dropwise. The ice bath was removed after addition was complete, and the reaction was stirred overnight. The reaction was then quenched by the slow addition of methanol (30 mL) with 1 hour of stirring. The solution was evaporated to a solid and redissolved in water (8 mL). (1) was isolated from this solution by reverse-phase HPLC as a white solid (318 mg, 0.96 mmol, 60%).

$^1$H NMR (300 MHz, $CD_3OD$) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, $CD_3OD$) d 16.47.

LC/MS: r.t.=1.48 min (3.5 min run), mass=332 (M+1).

Examples 2 & 3

(2)-(3) were prepared by the same method as (1) using the appropriate starting alcohol.

[2-(2-Amino-6-methoxy-purin-9-yl)-ethoxymethyl]-phosphonic acid (2)

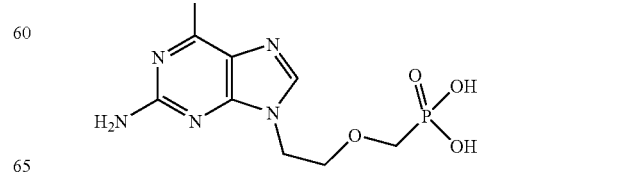

Reverse phase HPLC afforded (2) as a white solid (376 mg, 1.24 mmol, 77%).

$^1$H NMR (300 MHz, CD$_3$OD) d=8.05 (s, 1H), 4.32 (t, J=5.05 Hz, 2H), 4.06 (s, 3H), 3.90 (t, J=5.05 Hz, 2H), 3.64 (d, J=8.9 Hz, 2H).

$^{31}$P NMR (75 MHz, CD$_3$OD) d 15.43.

LC/MS: r.t.=1.21 min (3.5 min run), mass=304 (M+1).

[2-(2-Amino-6-isopropoxy-purin-9-yl)-ethoxymethyl]-phosphonic acid (3)

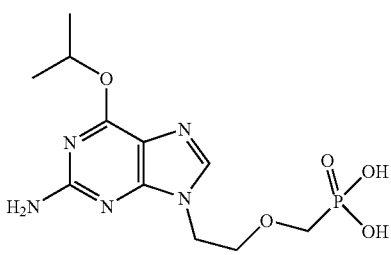

(3)

Reverse phase HPLC afforded (3) as a white solid (202 mg, 0.61 mmol, 38%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, CD$_3$OD) d 16.47.

LC/MS=332 (M$^+$+1).

Example 4

[2-(2-Amino-6-butoxy-purin-9-yl)-ethoxymethyl]-phosphonic acid (4)

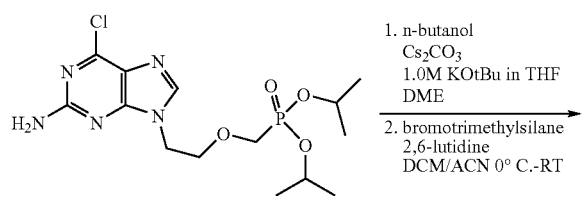

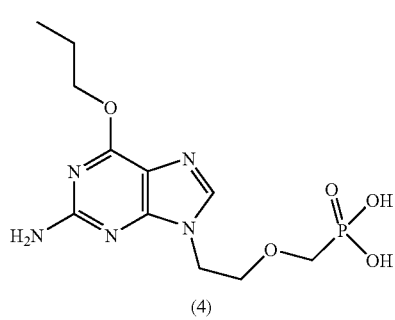

(4)

Phosphonic acid, P-[[2-(2-amino-6-chloro-9H-purin-9-yl)ethoxy]methyl]-, bis(1-methylethyl)ester (727 mg, 1.86 mmol, 1 eq.) and cesium carbonate (1.21 g, 3.72 mmol, 2 eq.) were weighed into a small flask and purged with N$_2$. 1,2-Dimethoxyethane (8 mL) and n-propanol (0.68 mL, 7.44 mmol, 4 eq.) were then added, and the mixture was stirred for 10 minutes. Potassium tert-butoxide (as 1.0 M solution in tetrahydrofuran, 2.05 mL, 2.05 mmol, 1.1 eq.) was then added dropwise.

The reaction was stirred 2.5 hours at room temperature and then concentrated to a solid. Following suspension in dichloromethane, the solids were removed by filtration. Concentration of the filtrate yielded a yellow oil from which product was isolated by column chromatography (SiO$_2$, 12% MeOH in dichloromethane) as a clear oil (616 mg, 1.435 mmol, 77%). This was then dissolved in dichloromethane (8 mL) under an atmosphere of N$_2$, and the reaction flask was cooled in an ice water bath to 0° C. 2,6-Lutidine (3.7 mL, 32 mmol, 20 eq.) was added, and then bromotrimethylsilane (3.1 mL, 24 mmol, 15 eq.) was added dropwise. The ice bath was removed after addition was complete, and the reaction was stirred overnight. The reaction was then quenched by the slow addition of methanol (30 mL) with 1 hour of stirring. The solution was then evaporated and the residue was redissolved in water (8 mL). Compound (4) was isolated from this solution by reverse-phase HPLC as a white solid (399 mg, 1.16 mmol, 62%).

$^1$H NMR (300 MHz, CD$_3$OD) d=8.35 (s, 1H), 4.55 (t, J=6.0 Hz, 2H), 4.40 (bs, 2H), 3.93 (bs, 2H), 3.73 (d, J=9.1 Hz, 2H), 1.83 (m, 2H), 1.54 (m, 2H), 1.01 (t, J=7.35 Hz, 3H).

$^{31}$P NMR (75 MHz, CD$_3$OD) d 17.19.

LC/MS: r.t.=1.67 min (3.5 min run), mass=346 (M+1).

Examples 5-12

(5)-(12) were prepared by the same method as (4), using the appropriate starting alcohol.

[2-(2-Amino-6-ethoxy-purin-9-yl)-ethoxymethyl]-phosphonic acid (5)

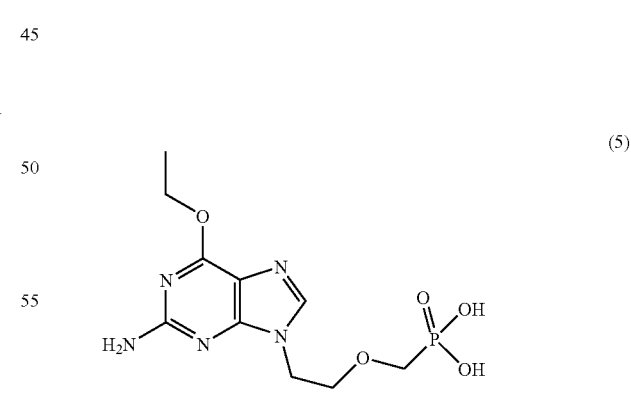

(5)

Reverse phase HPLC afforded (5) as a white solid (306 mg, 0.965 mmol, 78%).

$^1$H NMR (300 MHz, CD$_3$OD) d=7.98 (s, 1H), 4.54 (q, J=7.1 Hz, 2H), 4.30 (t, J=4.9 Hz, 2H), 3.88 (t, J=4.9 Hz, 2H), 3.59 (d, J=8.9 Hz, 2H), 1.43 (t, J=7.2 Hz, 3H).

$^{31}$P NMR (75 MHz, CD$_3$OD) d 14.69.

LC/MS: r.t.=0.82 min (3.5 min run), mass=318 (M+1).

[2-(2-Amino-6-cyclohexyloxy-purin-9-yl)-ethoxymethyl]-phosphonic acid (6)

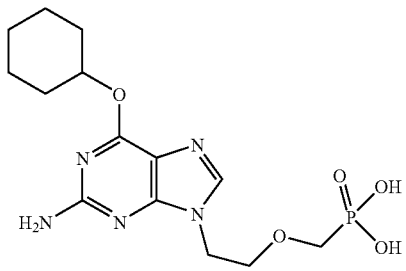

(6)

Reverse phase HPLC afforded (6) as a tan solid (306 mg, 0.965 mmol, 78%).

$^1$H NMR (300 MHz, CD$_3$OD) d=8.67 (s, 1H), 5.38 (m, 1 Hz), 4.45 (t, J=4.7 Hz, 2H), 3.96 (t, J=4.9 Hz, 2H), 3.76 (d, J=8.9 Hz, 2H), 2.06 (bm, 2H), 1.84 (bm, 2H), 1.65 (m, 3H) 1.45 (m, 3H).

$^{31}$P NMR (75 MHz, CD$_3$OD) d 17.94.

LC/MS: r.t.=1.52 min (3.5 min run), mass=372 (M+1).

[2-(2-Amino-6-pentyloxy-purin-9-yl)-ethoxymethyl]-phosphonic acid (7)

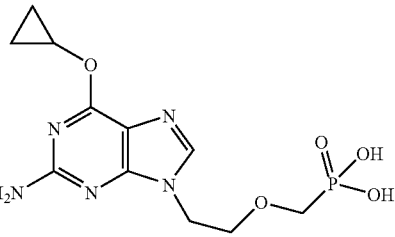

(7)

Reverse phase HPLC afforded (7) as a white solid (164 mg, 0.457 mmol, 47%).

$^1$H NMR (300 MHz, CD$_3$OD) d =8.17 (s, 1H), 4.51 (t, J=6.7 Hz, 2H), 4.36 (t, J=4.8 Hz, 2H), 3.91 (t, J=4.9 Hz, 2H), 3.69 (d, J=9.1 Hz, 2H), 1.84 (m, 2H), 1.45 (m, 4H), 0.953 (t, J=7.2 Hz, 3H).

$^{31}$P NMR (75 MHz, CD$_3$OD) d 16.36.

LC/MS; r.t.=1.57 min (3.5 min run), mass=360 (M+1).

[2-(2-Amino-6-cyclopropoxy-purin-9-yl)-ethoxymethyl]-phosphonic acid (8)

(8)

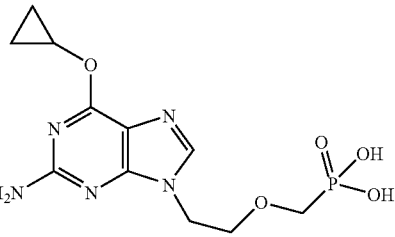

Reverse phase HPLC afforded (8) as a white solid (315 mg, 0.957 mmol, 47%).

$^1$H NMR (300 MHz, CD$_3$OD) d=8.02 (s, 1H), 4.56 (m, 1H), 4.31 (t, J=4.9 Hz, 2H), 3.89 (t, J=5.0 Hz, 2H), 3.62 (d, J=8.9 Hz, 2H), 0.84 (s, 4H).

$^{31}$P NMR (75 MHz, CD$_3$OD) d 15.32.

LC/MS: r.t.=1.02 min (3.5 min run), mass=330 (M+1).

[2-(2-Amino-6-cyclobutoxy-purin-9-yl)-ethoxymethyl]-phosphonic acid (9)

(9)

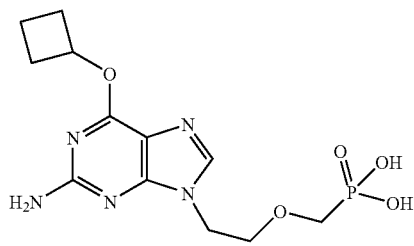

Reverse phase HPLC afforded the compound of Example 9 as a white solid (253 mg, 0.738 mmol, 69%).

$^1$H NMR (300 MHz, CD$_3$OD) d=8.14 (s, 1H), 5.42 (m, 1H) 4.34 (t, J=4.9 Hz, 2H), 3.90 (t, J=5.0 Hz, 2H), 3.68 (d, J=8.9 Hz, 2H), 2.52 (m, 2H), 2.23 (m, 2H), 1.80 (m, 2H).

$^{31}$P NMR (75 MHz, CD$_3$OD) d 16.22.

LC/MS: r.t.=1.29 min (3.5 min run), mass=344 (M+1).

[2-(2-Amino-6-cyclopentyloxy-purin-9-yl)-ethoxymethyl]-phosphonic acid (10)

(10)

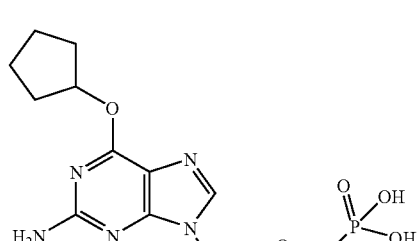

Reverse phase HPLC afforded (10) as a beige solid (319 mg, 0.738 mmol, 69%).

$^1$H NMR (300 MHz, CD$_3$OD) d=8.11 (s, 1H), 5.68 (m, 1H), 4.34 (t, J=4.9 Hz, 2H), 3.90 (t, J=4.9 Hz, 2H), 3.67 (d, J=8.8 Hz, 2H), 1.85 (bm, 8H), $^{31}$P NMR (75 MHz, CD$_3$OD) d 15.85

LC/MS: r.t.=1.66 min (3.5 min run), mass=358 (M+1)

{2-[2-Amino-6-(2-methoxy-ethoxy)-purin-9-yl]-ethoxymethyl}-phosphonic acid (11)

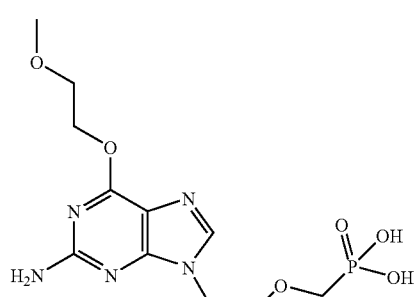

(11)

Reverse phase HPLC afforded the compound of Example 11 as a white solid (450 mg, 1.3 mmol, 62%).

$^1$H NMR (300 MHz, CD$_3$OD) d=8.11 (s, 1H), 4.63 (t, J=4.6 Hz, 2H), 4.33 (t, J=4.9 Hz, 2H), 3.91 (t, J=5.0 Hz, 2H), 3.79 (t, J=4.8 Hz, 2H), 3.68 (d, J=8.9 Hz, 2H), 3.41 (s, 3H).

$^{31}$P NMR (75 MHz, CD$_3$OD) d 16.01.

LC/MS: r.t.=1.03 min (3.5 min run), mass=348 (M+1).

[2-(2-Amino-6-cyclopropylamino-purin-9-yl)-ethoxymethyl]-phosphonic acid (12)

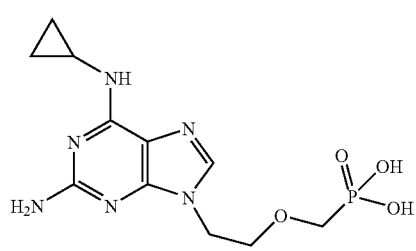

(12)

Diacid (12), CAS #182798-83-0, was prepared as described in patent WO2005/066189.

Example 13

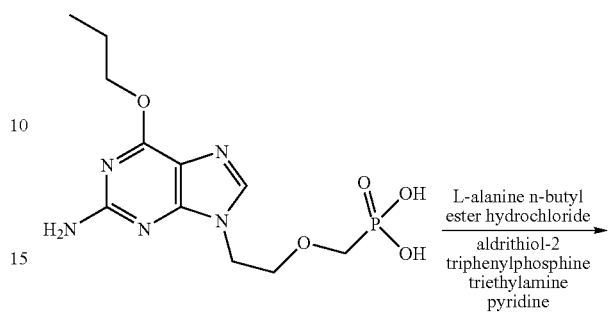

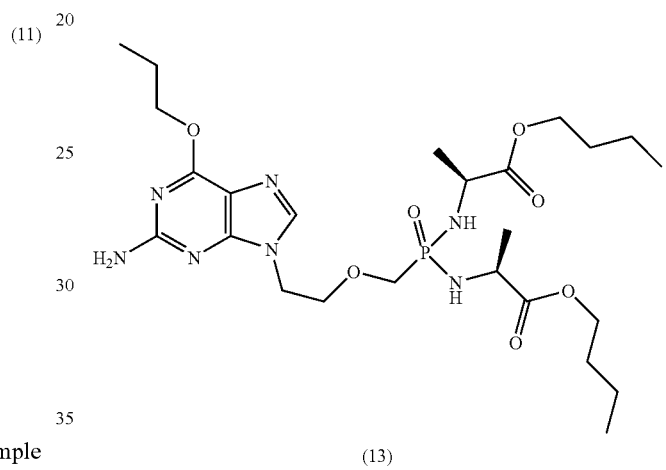

(13)

(1) (52 mg, 0.159 mmol, 1 eq.) and L-alanine n-butyl ester hydrochloride (200 mg, 1.10 mmol, 7 eq.) were weighed into a small flask and purged with N$_2$. Pyridine (1 mL) was added, and the mixture was warmed to 60° C. with stirring. A solution of aldrithiol-2 (243 mg, 1.10 mmol, 7 eq.), triphenylphosphine (289 mg, 1.10 mmol, 7 eq.) and triethylamine (265 μL, 1.90 mmol, 12 eq.) in 1 mL pyridine was added. The reaction was stirred at 60° C. under N$_2$ overnight. The reaction was then concentrated to a solid and left under high vacuum for 1 hour to remove residual pyridine. Column chromatography (SiO$_2$, 0-15% MeOH in dichloromethane) provided the desired product as a yellow solid (25 mg, 0.042 mmol, 27%).

$^1$H NMR (300 MHz, CD$_3$OD) d=7.93 (s, 1H), 4.44 (t, J=6.6 Hz, 2H), 4.30 (m, 2H), 4.10 (m, 4H), 3.89 (m, 4H), 3.76 (d, J=8.3 Hz, 2H), 1.85 (m, 2H), 1.61 (m, 4H), 1.40, (m, 10H), 1.07 (t, J=7.5 Hz, 3H), 0.92 (m, 6H).

$^{31}$P NMR (75 MHz, CD$_3$OD) d 23.49.

LC/MS: r.t.=2.39 min (3.5 min run), mass=586 (M+1).

Compounds (14) through (25) were prepared from (1) by the same method as (13) except for differences in the amino acid reagent. "Same method" as used herein means the same general procedure, with appropriate adjustments for the reagent(s).

Example 14

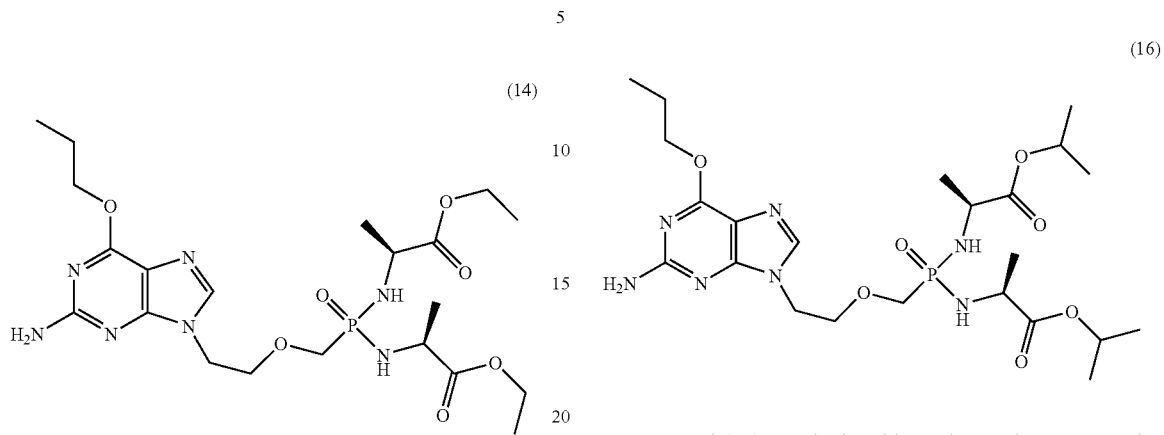

Compound (14) was isolated by column chromatography (SiO$_2$, 0-15% MeOH in dichloromethane) as an off-white solid (18 mg, 0.034 mmol, 21%).

$^1$H NMR (300 MHz, CD$_3$OD) d=7.92 (s, 1H), 4.44 (t, J=6.7 Hz, 2H), 4.32 (m, 2H), 4.12 (m, 4H), 3.91 (m, 4H), 3.75 (d, J=8.9 Hz, 2H), 1.86 (m, 2H), 1.51 (m, 2H), 1.30 (m, 10H), 1.07 (t, J=7.4 Hz, 3H).

$^{31}$P NMR (75 MHz, CD$_3$OD) d 23.56.

LC/MS: r.t=2.00 min (3.5 min run), mass=530 (M+1).

Example 15

Compound (15) was isolated by column chromatography (SiO$_2$, 0-15% MeOH in dichloromethane) as a yellow solid (15 mg, 0.022 mmol, 7%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, CD$_3$OD) δ 23.03.

LC/MS: r.t=2.51 min (3.5 min run), mass=682 (M+1).

Example 16

Compound (16) was isolated by column chromatography (SiO$_2$, 0-15% MeOH in dichloromethane) as a tan solid (20 my, 0.036 mmol, 22%).

$^1$H NMR (300 MHz, CD$_3$OD) d=8.01 (s, 1H), 5.11 (bm, 2H), 4.42 (t, J=6.6 Hz, 2H), 4.34 (t, J=4.7 Hz, 2H), 3.89 (m, 4H), 3.76 (d, J=8.2 Hz, 2H), 1.85 (m, 2H), 1.25 (bm, 18H), 1.07 (t, J=7.5 Hz, 3H).

$^{31}$P NMR (75 MHz, CD$_3$OD) d 23.495.

LC/MS: r.t=2.19 min (3.5 min run), mass=558 (M+1).

Example 17

Compound (17) was isolated by column chromatography (SiO$_2$, 0-15% MeOH in dichloromethane) as an off-white solid (25 mg, 0.034 mmol, 20%).

$^1$H NMR (300 MHz, CO$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, CD$_3$OD) d 22.99.

LC/MS: r.t=2.86 min (3.5 min run), mass=738 (M+1).

Example 18

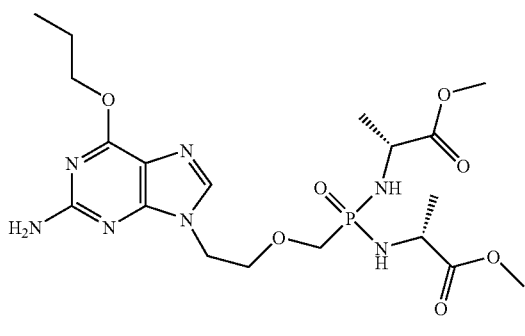

(18)

Compound (18) was isolated by column chromatography (SiO$_2$, 0-15% MeOH in dichloromethane) as an off-white solid (10 mg, 0.020 mmol, 10%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, CD$_3$OD) d 23.51.

LC/MS: r.t=1.81 min (3.5 min run), mass=502 (M+1).

Example 19

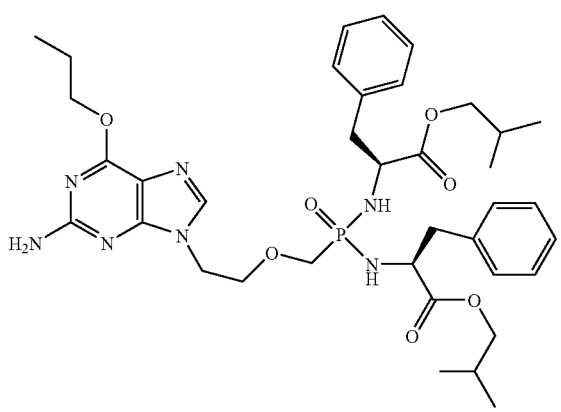

(19)

Compound (19) was isolated by column chromatography (SiO$_2$, 0-15% MeOH in dichloromethane) as an off-white solid (20 mg, 0.027 mmol, 15%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, CD$_3$OD) d 22.93.

LC/MS: r.t=2.78 min (3.5 min run), mass=738 (M+1).

Example 20

(20)

Compound (20) was isolated by column chromatography (SiO$_2$, 0-15% MeOH in dichloromethane) as a white solid (80 mg, 0.113 mmol, 54%).

$^1$H NMR (300 MHz, CD$_3$OD) d=7.82 (s, 1H), 7.33 (m, 10H), 5.09 (m, 4H), 4.42 (t, J=6.7 Hz, 2H), 4.21 (m, 4H), 3.6-3.9 (bm, 4H), 2.9-3.2 (bm, 4H), 2.05 (m, 2H), 1.6-1.9 (bm, 8H), 1.05 (t, J=7.5 Hz, 3H).

$^{31}$P NMR (75 MHz, CD$_3$OD) d 23.26.

LC/MS: r.t=2.34 min (3.5 min run), mass=706 (M+1).

Example 21

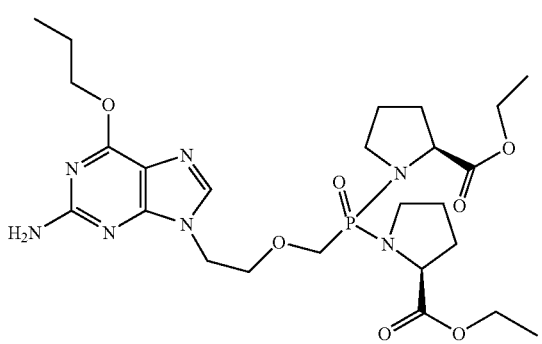

(21)

Compound (21) was isolated by column chromatography (SiO$_2$, 0-15% MeOH in dichloromethane) as a colorless, glassy solid (43 mg, 0.074 mmol, 36%).

$^1$H NMR (300 MHz, CD$_3$OD) d=7.89 (s, 1H), 4.45 (t, J=6.6 Hz, 2H), 4.31 (m, 2H), 3.9-4.2 (bm, 8H), 3.82 (m, 2H), 3.0-3.3 (bm, 4H), 2.11 (bm, 2H), 1.7-1.95 (bm, 8H), 1.25 (m, 6H), 1.06 (t, J=7.5 Hz, 3H).

$^{31}$P NMR (75 MHz, CD$_3$OD) d 23.27.

LC/MS: r.t=1.90 min (3.5 min run), mass=582 (M+1).

Example 22

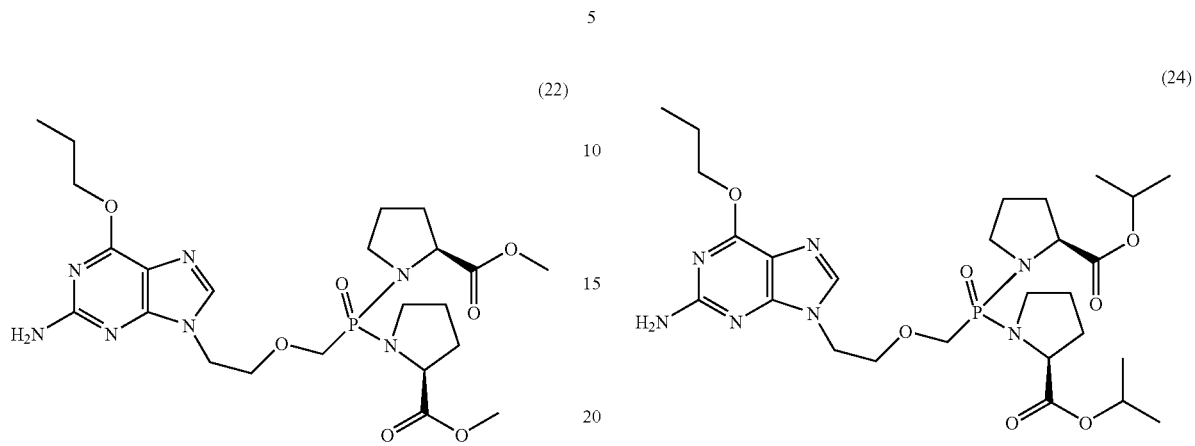

Compound (22) was isolated by column chromatography (SiO$_2$, 0-15% MeOH in dichloromethane) as a white solid (68 mg, 0.123 mmol, 59%).

$^1$H NMR (300 MHz, CD$_3$OD) d=7.88 (s, 1H), 4.45 (t, J=6.5 Hz, 2H), 4.32 (m, 2H), 4.21 (m, 1H), 4.18 (m, 1H), 3.99 (m, 1H) 3.76 (bm, 3H), 3.66 (m, 6H), 3.08-3.24 (bm, 4H), 2.09, (m, 2H), 1.85 (bm, 8H), 1.06 (t, J=7.4 Hz, 3H).

$^{31}$P NMR (75 MHz, CD$_3$OD) d 23.34.

LC/MS: r.t=1.97 min (3.5 min run), mass=554 (M+1).

Example 23

Compound (23) was isolated by column chromatography (SiO$_2$, 0-15% MeOH in dichloromethane) as a tan solid (52 mg, 0.085 mmol, 41%).

$^1$H NMR (300 MHz, CD$_3$OD) d=7.88 (s, 1H), 4.45 (t, J=6.6 Hz, 2H), 4.26 (m, 3H), 4.10 (m, 6H), 3.88 (m, 3H), 3.19 (m, 4H), 2.11 (m, 2H), 1.85 (bm, 8H), 1.68 (m, 4H), 1.065 (t, J=7.4 Hz, 3H), 0.93 (m, 6H).

$^{31}$P NMR (75 MHz, CD$_3$OD) d 23.28.

LC/MS: r.t=2.43 min (3.5 min run), mass=610 (M+1).

Example 24

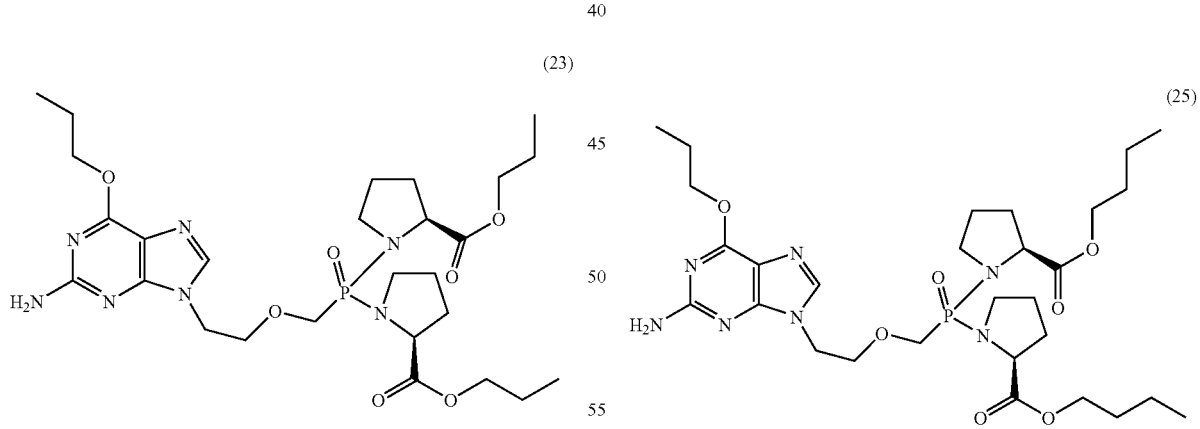

Compound (24) was isolated by column chromatography (SiO$_2$, 0-15% MeOH in dichloromethane) as a white solid (47 mg, 0.077 mmol, 37%).

$^1$H NMR (300 MHz, CD$_3$OD) d=7.89 (s, 1H), 4.93 (m, 2H), 4.45 (t, J=6.7 Hz, 2H), 4.33 (bm, 2H), 4.17 (bm, 1H), 4.02 (m, 2H), 3.87 (m, 3H), 3.25 (bm, 4H), 2.11 (m, 2H), 1.84 (m, 8H), 1.21 (m, 12H), 1.06 (t, J=7.5 Hz, 3H).

$^{31}$P NMR (75 MHz, CD$_3$OD) d 23.19.

LC/MS: r.t=3.56 min (6 min run), mass=610 (M+1).

Example 25

Compound (25) was isolated by column chromatography (SiO$_2$, 0-15% MeOH in dichloromethane) as a light tan solid (75 mg, 0.118 mmol, 57%).

$^1$H NMR (300 MHz, CD$_3$OD) d=7.88 (s, 1H), 4.45 (t, J=6.7 Hz, 2H), 4.32 (m, 2H), 4.21 (m, 1H), 4.08 (m, 6H), 3.87 (m, 3H), 3.19 (m, 4H), 2.07 (m, 2H), 1.81 (bm, 9H), 1.61 (m, 2H), 1.38 (m, 5H), 1.06 (t, J=7.35 Hz, 3H), 0.95 (m, 6H). $^{31}$P NMR (75 MHz, CD$_3$OD) d 23.31.

LC/MS: r.t=4.03 min (6 min run), mass=638 (M+1).

Example 26

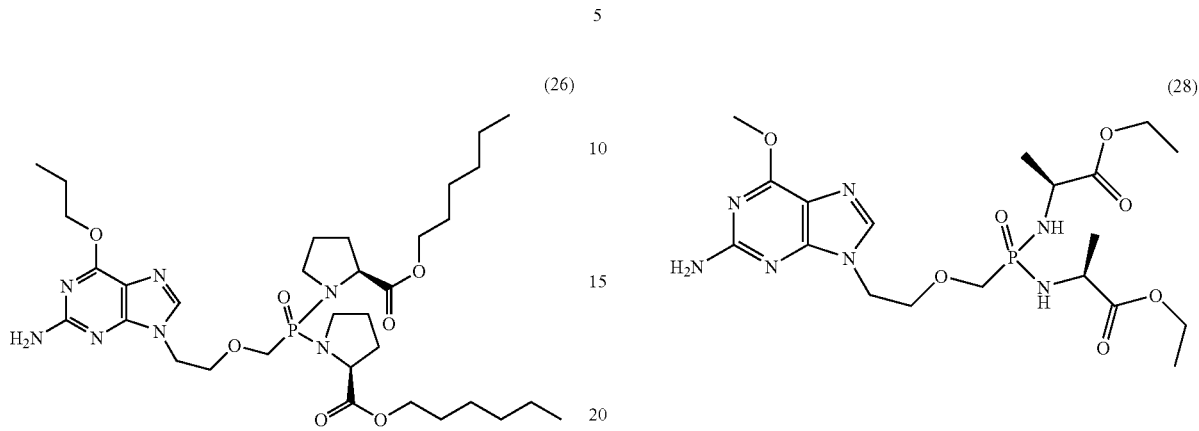

Compound (26) was isolated by column chromatography (SiO$_2$, 0-15% MeOH in dichloromethane) as a yellow oil (8 mg, 0.012 mmol, 9%).

$^1$H NMR (300 MHz, CD$_3$OD) d=7.88 (s, 1H), 4.45 (t, J=6.7 Hz, 2H), 4.32 (m, 2H), 4.21 (m, 1H), 4.04 (m, 6H), 3.90 (m, 3H), 3.19 (m, 4H), 2.11 (m, 2H), 1.81 (bm, 8H), 1.61 (bm, 4H), 1.38 (m, 12H), 1.07 (t, J=7.35 Hz, 3H), 0.91 (m, 6H).

$^{31}$P NMR (75 MHz, CD$_3$OD) d23.35.

LC/MS: r.t=4.71 min (6 min run), mass=694 (M+1).

Compounds 27 through 32 were prepared from (2) by the same method as that described in Example 13.

Example 27

Compound (27) was isolated by column chromatography (SiO$_2$, 0-15% MeOH in dichloromethane) as an off-white solid (10 mg, 0.018 mmol, 14%).

$^1$H NMR (300 MHz, CD$_3$OD) d=7.93 (s, 1H), 4.32 (m, 2H), 4.10 (m, 4H), 4.05 (s, 3H), 3.82 (m, 4H), 3.75 (d, J=8.3 Hz, 2H), 1.61 (m, 4H), 1.40 (m, 4H), 1.33 (m, 6H), 0.95 (m, 6H). $^{31}$P NMR (75 MHz, CD$_3$OD) d 23.49.

LC/MS: r.t=2.23 min (3.5 min run), mass=558 (M+1).

Example 28

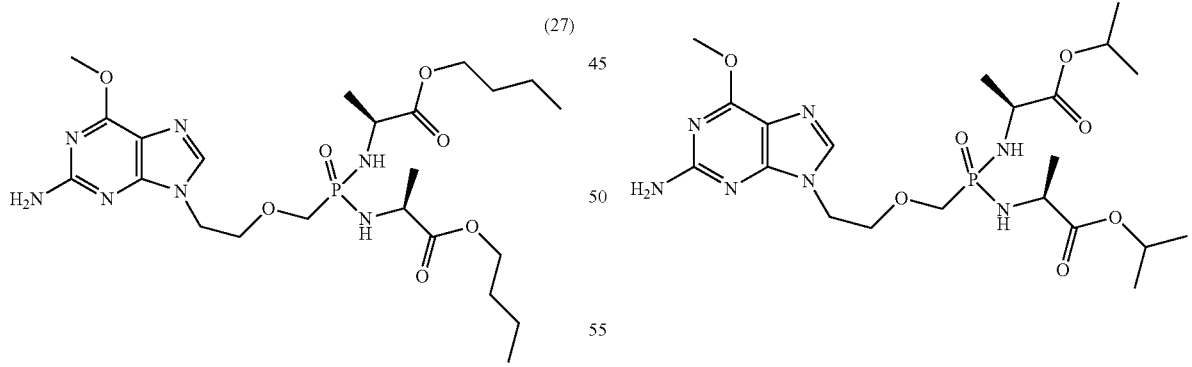

Compound (28) was isolated by column chromatography (SiO$_2$, 0-15% MeOH in dichloromethane) as an off-white solid (15 mg, 0.030 mmol, 17%).

$^1$H NMR (300 MHz, CD$_3$OD) d=7.93 (s, 1H), 4.32 (m, 2H), 4.12 (m, 4H), 4.05 (s, 3H), 3.90 (m, 4H), 3.75 (d, J=8.6 Hz, 2H), 1.30 (bm, 12H).

$^{31}$P NMR (75 MHz, CD$_3$OD) d 23.51.

LC/MS: r.t=1.74 min (3.5 min run), mass=502 (M+1).

Example 29

Compound (29) was isolated by column chromatography (SiO$_2$, 0-15% MeOH in dichloromethane) as a tan solid (20 mg, 0.038 mmol, 22%).

$^1$H NMR (300 MHz, CD$_3$OD) d=7.94 (s, 1H), 4.98 (m, 2H), 4.32 (t, J=4.9 Hz, 2H), 4.05 (s, 3H), 3.90 (m, 4H), 3.75 (d, J=8.6 Hz, 2H), 1.31 (m, 6H), 1.23 (m, 12H). $^{31}$P NMR (75 MHz, CD$_3$OD) d 23.48.

LC/MS: r.t=1.92 min (3.5 min run), mass=530 (M+1).

Example 30

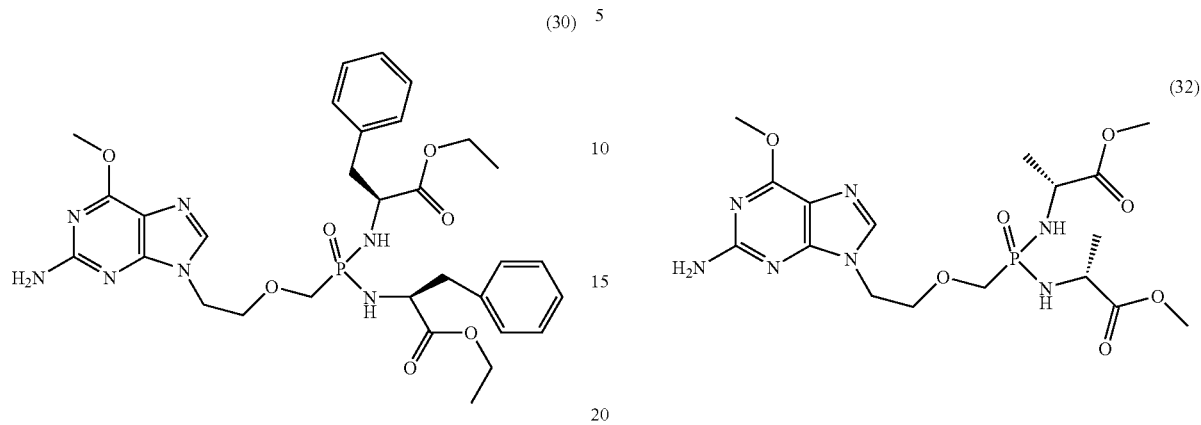

Compound (30) was isolated by column chromatography (SiO$_2$, 0-15% MeOH in dichloromethane) as a white solid (20 mg, 0.031 mmol, 17%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H). $^{31}$P NMR (75 MHz, CD$_3$OD) d 23.01. LC/MS: r.t=2.29 min (3.5 min run), mass=654 (M+1).

Example 31

Compound (31) was isolated by column chromatography (SiO$_2$, 0-15% MeOH in dichloromethane) as an off-white solid (22 mg, 0.031 mmol, 17%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t J=4.9 Hz, 2H), 3.70 (d, J=8.9 Hz, 2H), 1.87 (m, 2H), 1.07 (t, J=7.5 Hz, 3H). $^{31}$P NMR (75 MHz, CD$_3$OD) d 22.99. LC/MS: rt=2.65 min (3.5 min run), mass=710 (M+1).

Example 32

Compound (32) was isolated by column chromatography (SiO$_2$, 0-15% MeOH in dichloromethane) as an off-white solid (15 mg, 0.032 mmol, 17%).

$^1$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

$^{31}$P NMR (75 MHz, CD$_3$OD) d 23.50.

LC/MS: r.t=1.63 min (3.5 min run), mass=474 (M+1). Compounds 33 and 34 were prepared from (3) by the same method as described in Example 13.

Example 33

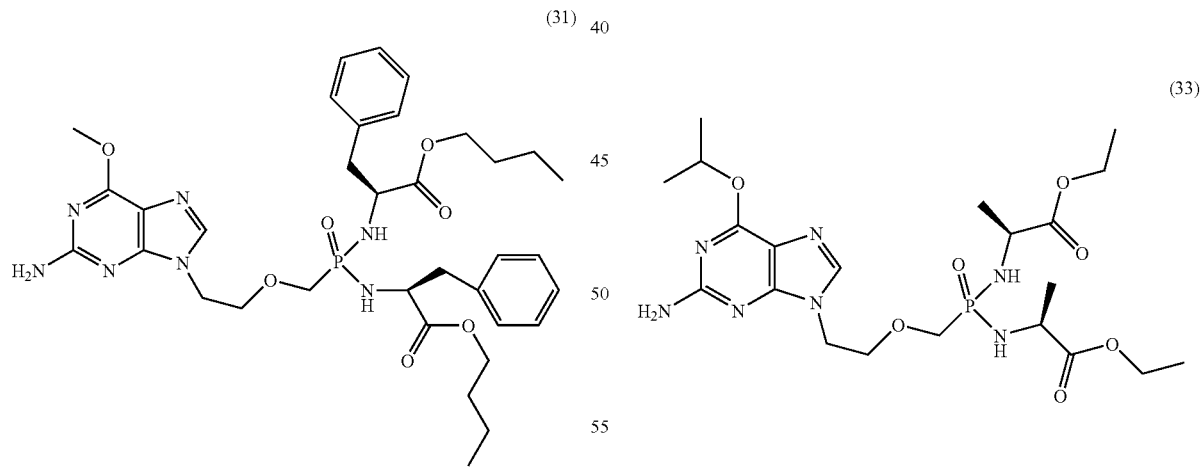

Compound (33) was isolated by column chromatography (SiO$_2$, 0-15% MeOH in dichloromethane) as an off-white solid (47 mg, 0.089 mmol, 53%).

$^1$H NMR (300 MHz, CD$_3$OD) d=7.91 (s, 1H), 5.55 (m, 1H), 4.31 (m, 2H), 4.14 (m, 4H), 3.89 (m, 4H), 3.75 (d, J=8.9 Hz, 2H), 1.40 (m, 6H), 1.25 (m, 12H). $^{31}$P NMR (75 MHz, CD$_3$OD) d 23.56.

LC/MS: r.t=1.74 min (3.5 min run), mass=530 (M+1).

Example 34

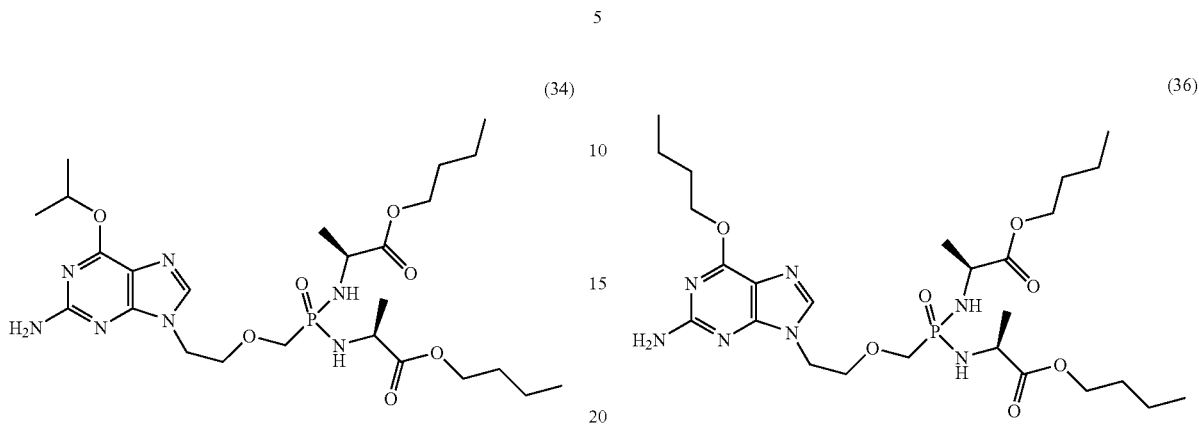

Compound (34) was isolated by column chromatography (SiO$_2$, 0-15% MeOH in dichloromethane) as an off-white solid (42 mg, 0.073 mmol, 44%).

$^1$H NMR (300 MHz, CD$_3$OD) d=7.91 (s, 1H), 5.56 (m, 1H), 4.31 (m, 2H), 4.10 (m, 4H), 3.89 (m, 4H), 3.75 (m, 2H), 1.62 (m, 4H), 1.41 (m, 10H), 1.33 (m, 6H), 0.95 (m, 6H).

$^{31}$P NMR (75 MHz, CD$_3$OD) d 23.51.

LC/MS: r.t=2.17 min (3.5 min run), mass=586 (M+1). Compounds 35 and 36 were prepared from (4) by the same method as described in Example 13.

Example 35

Compound (35) was isolated by column chromatography (SiO$_2$, 0-15% MeOH in dichloromethane) as a tan glassy solid (55 mg, 0.101 mmol, 56%).

$^1$H NMR (300 MHz, CD$_3$OD) d=7.92 (s, 1H), 4.49 (t, J=6.7 Hz, 2H), 4.32 (t, J=4.9 Hz, 2H), 4.18 (m, 4H), 3.89 (m, 4H), 3.75 (d, J=8.6 Hz, 2H), 1.80 (m, 2H), 1.54 (m, 2H), 1.32 (m, 6H), 1.24 (m, 6H), 1.00 (t, J=7.4 Hz, 3H). $^{31}$P NMR (75 MHz, CD$_3$OD) d 23.52.

LC/MS: r.t=1.88 min (3.5 min run), mass=544 (M+1).

Example 36

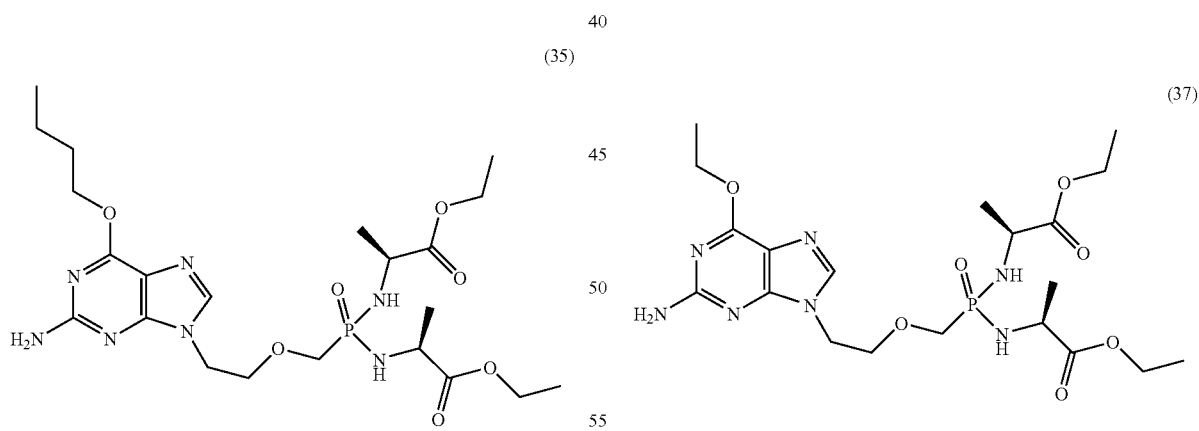

Compound (36) was isolated by column chromatography (SiO$_2$, 0-15% MeOH in dichloromethane) as an off-white solid (64 mg, 0.107 mmol, 45%).

$^1$H NMR (300 MHz, CD$_3$OD) d=7.92 (s, 1H), 4.49 (t, J=6.6 Hz, 2H), 4.31 (t, J=4.8 Hz, 2H), 4.09 (m, 4H), 3.89 (m, 4H), 3.75 (d, J=8.9 Hz, 2H), 1.82 (m, 2H), 1.60 (m, 6H), 1.39 (m, 4H), 1.32 (m, 6H), 0.94 (m, 9H). $^{31}$P NMR (75 MHz, CD$_3$OD) d 23.50.

LC/MS: r.t=2.29 min (3.5 min run), mass=600 (M+1).

Compounds 37 and 38 were prepared from (5) by the same method as described in Example 13.

Example 37

Compound (37) was isolated by column chromatography (SiO$_2$, 0-15% MeOH in dichloromethane) as a pale yellow solid (59 mg, 0.115 mmol, 49%).

$^1$H NMR (300 MHz, CD$_3$OD) d=7.98 (s, 1H), 4.51 (m, 2H), 4.33 (m, 2H), 4.14 (m, 4H), 3.90 (m, 4H), 3.75 (d, J=8.8 Hz, 2H), 1.41 (m, 3H), 1.26 (m, 6H), 1.23 (m, 6H).

$^{31}$P NMR (75 MHz, CD$_3$OD) d23.51.

LC/MS: r.t=1.65 min (3.5 min run), mass=516 (M+1).

Example 38

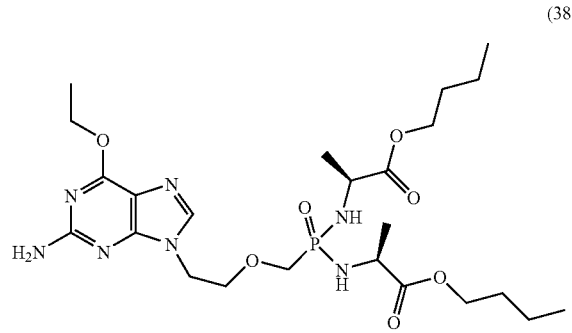

(38)

Compound (38) was isolated by column chromatography (SiO$_2$, 0-15% MeOH in dichloromethane) as a glassy beige solid (60 mg, 0.105 mmol, 44%).

$^1$H NMR (300 MHz, CD$_3$OD) d=7.92 (s, 1H), 4.54 (m, 2H), 4.31 (t, J=4.9 Hz, 2H), 4.09 (m, 4H), 3.89 (m, 4H), 3.75 (d, J=8.6 Hz, 2H), 1.60 (m, 4H), 1.44 (m, 6H), 1.33 (m, 8H), 0.94 (m, 5H).

$^{31}$P NMR (75 MHz, CD$_3$OD) d23.50.

LC/MS: r.t=2.10 min (3.5 min run), mass=572 (M+1). Compounds 39 and 40 were prepared from (6) by the same method as described in Example 13.

Example 39

(39)

Compound (39) was isolated by column chromatography (SiO$_2$, 0-15% MeOH in dichloromethane) as a white solid (49 mg, 0.086 mmol, 47%).

$^1$H NMR (300 MHz, CD$_3$OD) d=7.90 (s, 1H), 5.31 (m, 1H), 4.31 (m, 2H), 4.12 (m, 4H), 3.89 (m, 4H), 3.74 (d, J=8.8 Hz, 2H), 2.04 (bm, 2H), 1.85 (bm, 2H), 1.62 (m, 3H), 1.41 (m, 3H), 1.32 (m, 6H), 1.25 (m, 6H).

$^{31}$P NMR (75 MHz, CD$_3$OD) d 23.53.

LC/MS: r.t=1.97 min (3.5 min run), mass=570 (M+1).

Example 40

(40)

Compound (40) was isolated by column chromatography (SiO$_2$, 0-15% MeOH in dichloromethane) as an off-white solid (70 mg, 0.113 mmol, 63%).

$^1$H NMR (300 MHz, CD$_3$OD) d=8.42 (s, 1H), 5.37 (m, 1H), 4.40 (m, 2H), 4.12 (m, 6H), 3.91 (m, 4H), 3.23 (m, 2H), 3.12 (m, 2H), 2.11 (m, 4H), 1.83 (m, 8H), 1.65 (m, 3H), 1.34 (m, 3H), 1.24 (m, 6H)

$^{31}$P NMR (75 MHz, CD$_3$OD) d 23.38.

LC/MS: r.t=2.07 min (3.5 min run), mass=622 (M+1).

Example 41 was prepared from (7) by the same method as that described in Example 13.

Example 41

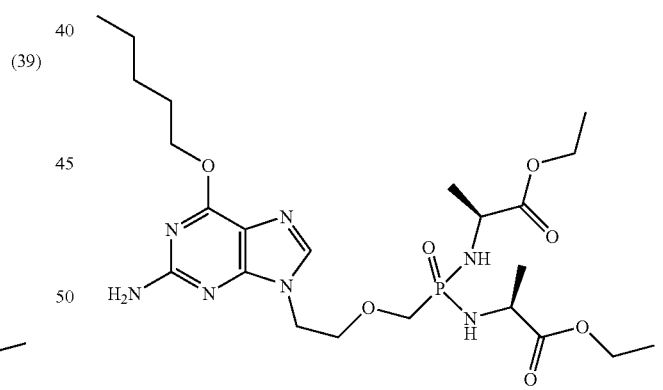

(41)

Compound (41) was isolated by column chromatography (SiO$_2$, 0-15% MeOH in dichloromethane) as a glassy pale yellow solid (54 mg, 0.097 mmol, 53%).

$^1$H NMR (300 MHz, CD$_3$OD) d=7.92 (s, 1H), 4.48 (t, J=6.7 Hz, 2H), 4.32 (t, J=4.9 Hz, 2H), 4.13 (m, 4H), 3.89 (m, 4H), 3.75 (d, J=8.6 Hz, 2H), 1.84 (m, 2H), 1.44 (m, 4H), 1.32 (m, 6H), 1.27 (m, 6H), 0.95 (t, J=7.0 Hz, 3H). $^{31}$P NMR (75 MHz, CD$_3$OD) d 23.52.

LC/MS: r.t=2.01 min (3.5 min run), mass=558 (M+1)

Compounds 42 through 44 were prepared from (8) by the same method as described in Example 13. .

Example 42

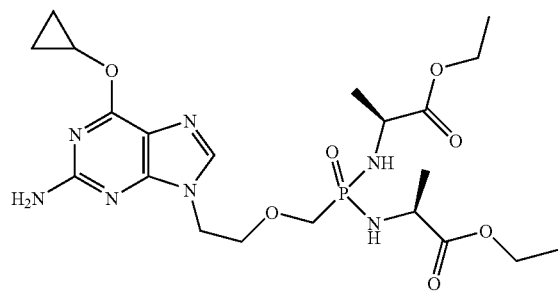

(42)

Compound (42) was isolated by column chromatography (SiO$_2$, 0-15% MeOH in dichloromethane) as a white solid (57 mg, 0.108 mmol, 52%).

$^1$H NMR (300 MHz, CD$_3$OD) d=7.92 (s, 1H), 4.54 (m, 1H), 4.32 (t, J=4.8 Hz, 2H), 4.14 (m, 4H), 3.90 (m, 4H), 3.75 (d, J=9.2 Hz, 2H), 1.32 (m, 6H), 1.25 (m, 6H), 0.83 (m, 4H).

$^{31}$P NMR (75 MHz, CD$_3$OD) d 23.51.

LC/MS: r.t=1.94 min (3.5 min run), mass=528 (M+1).

Example 43

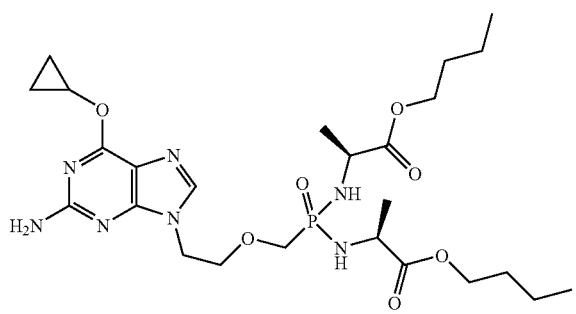

(43)

Compound (43) was isolated by column chromatography (SiO$_2$, 0-15% MeOH in dichloromethane) as a glassy beige solid (89 mg, 0.152 mmol, 73%).

$^1$H NMR (300 MHz, CD$_3$OD) d=7.93 (s, 1H), 4.54 (m, 1H), 4.32 (t, J=5.0 Hz, 2H), 4.10 (m, 4H), 3.89 (m, 4H), 3.75 (d, J=8.9 Hz, 2H), 1.60 (m, 4H), 1.39 (m, 4H), 1.33 (m, 6H), 0.95 (m, 6H), 0.83 (m, 4H). $^{31}$P NMR (75 MHz, CD$_3$OD) d 23.49.

LC/MS: r.t=2.36 min (3.5 min run), mass=584 (M+1).

Example 44

(44)

Compound (44) was isolated by column chromatography (SiO$_2$, 0-15% MeOH in dichloromethane) as a pale yellow solid (61 mg, 0.105 mmol, 51%).

$^1$H NMR (300 MHz, CD$_3$OD) d=8.60 (s, 1H), 4.62 (m, 1H), 4.43 (m, 2H), 4.11 (bm, 6H), 3.91 (m, 4H), 3.21 (m, 3H), 2.10 (m, 3H), 1.80 (m, 6H), 1.23 (m, 6H), 0.87 (s, 4H).

$^{31}$P NMR (75 MHz, CD$_3$OD) d 23.38, 24.49.

LC/MS: r.t=2.10 min (3.5 min run), mass=572 (M+1).

Example 45 was prepared from (9) by the same method as described in Example 13.

Example 45

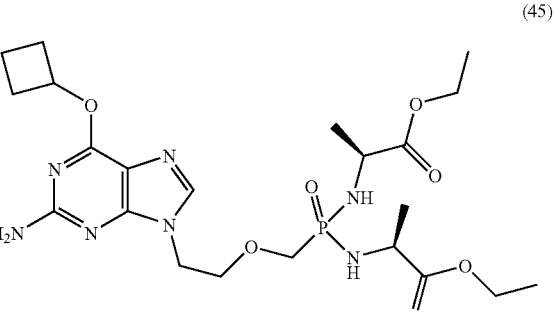

(45)

Compound (45) was isolated by column chromatography (SiO$_2$, 0-15% MeOH in dichloromethane) as a glassy pale yellow solid (41 mg, 0.097 mmol, 53%).

$^1$H NMR (300 MHz, CD$_3$OD) d=7.92 (s, 1H), 5.41 (m, 1H), 4.31 (t, J=4.9 Hz, 2H), 4.12 (m, 4H), 3.88 (m, 4H), 3.75 (d, J=8.8 Hz, 2H), 2.50 (m, 2H), 2.23 (m, 2H), 1.88 (m, 1H), 1.72 (m, 1H), 1.31 (m, 6H), 1.23 (m, 6H).

$^{31}$P NMR (75 MHz, CD$_3$OD) d 23.52.

LC/MS: r.t=1.82 min (3.5 min run), mass=542 (M+1).
Compounds 46 and 47 were prepared from (10) by the same method as described in Example 13.

Example 46

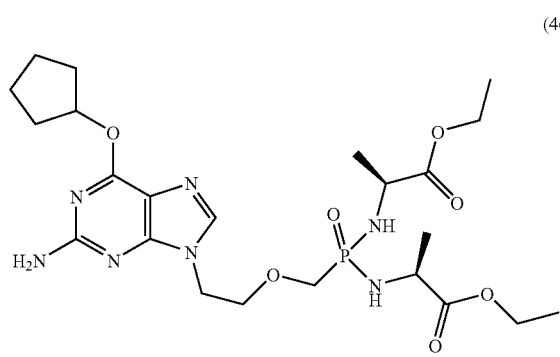

(46)

Compound (46) was isolated by column chromatography (SiO₂, 0-15% MeOH in dichloromethane) as a pale yellow solid (56 mg, 0.101 mmol, 56%).

$^1$H NMR (300 MHz, CD$_3$OD) d=7.90 (s, 1H), 5.66 (m, 1H), 4.31 (t, J=4.8 Hz, 2H), 4.12 (m, 4H), 3.89 (m, 4H), 3.75 (d, J=9.1 Hz, 2H), 2.01 (m, 2H), 1.87 (m, 4H), 1.68 (m, 2H), 1.32 (m, 6H), 1.23 (m, 6H).

$^{31}$P NMR (75 MHz, CD$_3$OD) d 23.53.

LC/MS: r.t=1.88 min (3.5 min run), mass=556 (M+1).

Example 47

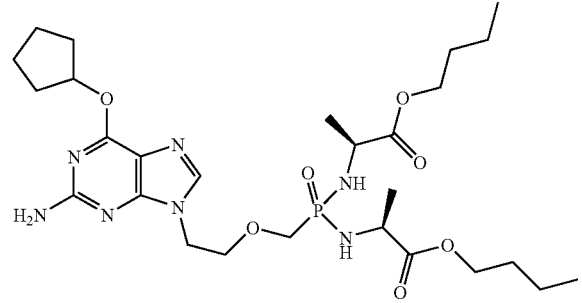

(47)

Compound (47) was isolated by column chromatography (SiO₂, 0-15% MeOH in dichloromethane) as a yellow solid (105 mg, 0.171 mmol, 72%).

$^1$H NMR (300 MHz, CD$_3$OD) d=7.91 (s, 1H), 5.67 (bs, 1H), 4.31 (t, J=4.9 Hz, 2H), 4.08 (m, 4H), 3.89 (m, 4H), 3.75 (d, J=8.3 Hz, 2H), 3.22 (m, 4H), 2.01 (m, 2H), 1.88 (m, 3H), 1.62 (m, 3H), 1.39 (m, 4H), 1.32 (m, 6H), 0.96 (m, 6H).

$^{31}$P NMR (75 MHz, CD$_3$OD) d 23.50.

LC/MS: r.t=2.28 min (3.5 min run), mass=612 (M+1).

Compounds 48 and 49 were prepared from (11) by the same method as described in Example 13.

Example 48

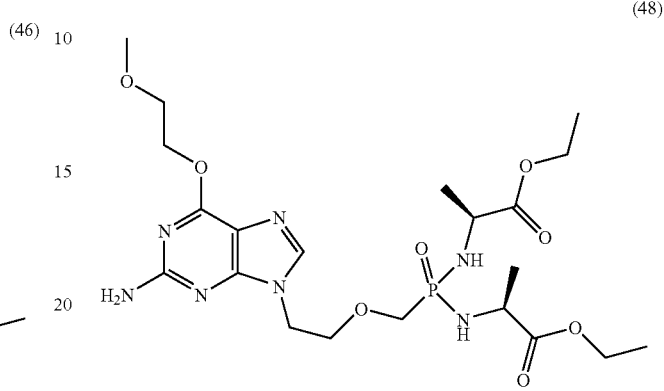

(48)

Compound (48) was isolated by column chromatography (SiO₂, 0-15% MeOH in dichloromethane) as a colorless glassy solid (103 mg, 0.189 mmol, 69%).

$^1$H NMR (300 MHz, CD$_3$OD) d=7.92 (s, 1H), 4.62 (t, J=4.7 Hz, 2H), 4.32 (t, J=4.7 Hz, 2H), 4.14 (m, 4H), 3.90 (m, 4H), 3.81 (m, 2H), 3.75 (d, J=9.2 Hz, 2H), 3.41 (s, 3H), 1.32 (m, 6H), 1.24 (m, 6H).

$^{31}$P NMR (75 MHz, CD$_3$OD) d 23.52.

LC/MS: r.t=1.67 min (3.5 min run), mass=546 (M+1).

Example 49

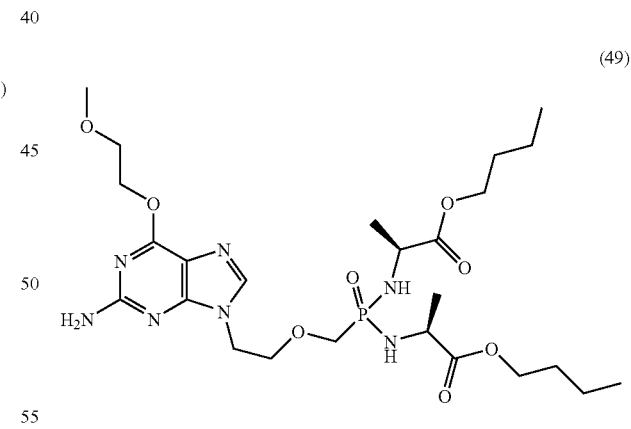

(49)

Compound (49) was isolated by column chromatography (SiO₂, 0-15% MeOH in dichloromethane) as a yellow solid (85 mg, 0.141 mmol, 52%).

$^1$H NMR (300 MHz, CD$_3$OD) d=7.93 (s, 1H), 4.61 (t, J=4.7 Hz, 2H), 4.32 (t, J=4.8 Hz, 2H), 4.09 (m, 4H), 3.89 (m, 4H), 3.80 (m, 2H), 3.75 (d, J=8.3 Hz, 2H), 3.41 (s, 3H), 1.60 (m, 4H), 1.33 (m, 10H), 0.94 (m, 6H).

$^{31}$P NMR (75 MHz, CD$_3$OD) d 23.50.

LC/MS: r.t=2.09 min (3.5 min run), mass=602 (M+1).

Compounds 50 and 51 were prepared from (12) by the same method as described in Example 13.

Example 50

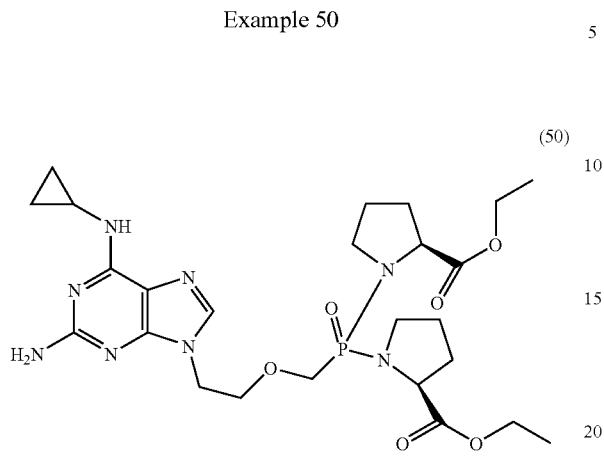

(50)

Compound (50) was isolated by column chromatography (SiO$_2$, 0-15% MeOH in dichloromethane) as a off-white solid (22 mg, 0.038 mmol, 18%).

$^1$H NMR (300 MHz, CD$_3$OD) d=7.77 (s, 1H), 4.27 (m, 2H), 4.13 (bm, 6H), 3.85 (m, 4H), 3.18 (m, 4H), 2.92 (m, 1H), 2.10 (m, 2H), 1.45-1.90 (bm, 6H), 1.23 (m, 6H), 0.85 (m, 2H), 0.60 (m, 2H).

$^{31}$P NMR (75 MHz, CD$_3$OD) d 23.38.

LC/MS: r.t=2.09 min (3.5 min run), mass=579 (M+1).

Example 51

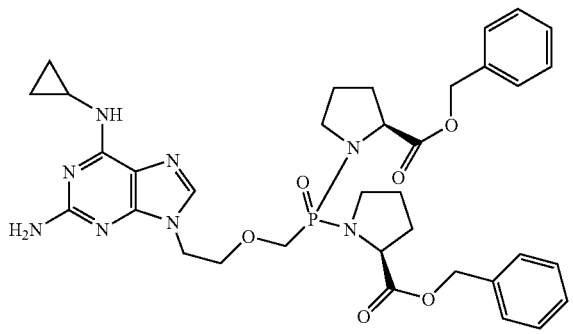

(51)

Compound (51) was isolated by column chromatography (SiO$_2$, 0-15% MeOH in dichloromethane) as a pale yellow solid (40 mg, 0.057 mmol, 27%).

$^1$H NMR (300 MHz, CD$_3$OD) d=7.70 (s, 1H), 7.34 (m, 10H), 5.09 (m, 4H), 4.16 (m, 4H), 3.6-3.9 (bm, 4H), 3.12 (m, 4H), 2.92 (m, 1H), 2.05 (m, 2H), 1.89 (m, 2H), 1.73 (m, 4H), 0.84 (m, 2H), 0.59 (m, 2H).

$^{31}$P NMR (75 MHz, CD$_3$OD) d 23.36.

LC/MS: r.t=2.04 min (3.5 min run), mass=703 (M+1).

Example 52

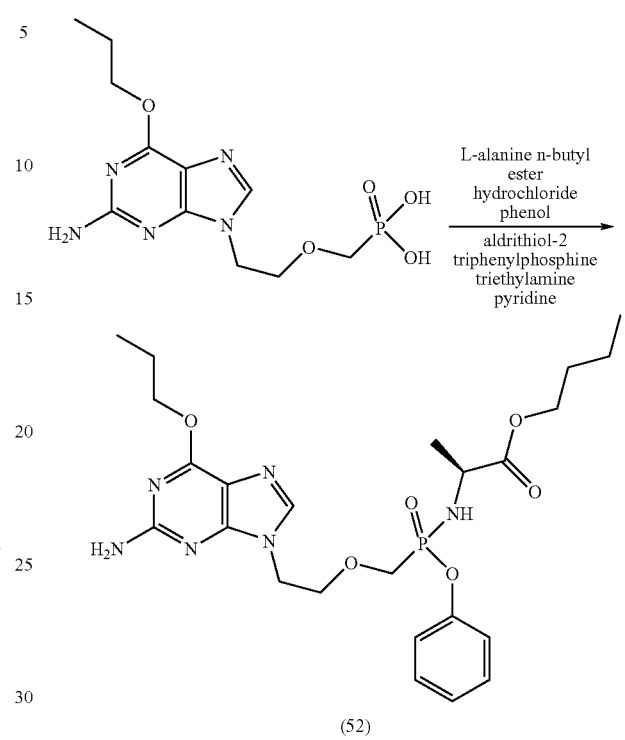

(52)

[[2-(2-Amino-6-chloro-9H-purin-9-yl)ethoxy]methyl]-phosphonic acid, bis(1-methylethyl) ester (78 mg, 0.239 mmol, 1 eq.), phenol (112 mg, 1.193 mmol, 5 eq.), and L-alanine n-butyl ester hydrochloride (78 mg, 0.43 mmol, 1.8 eq.) were weighed into a small flask and purged with N$_2$. Pyridine (1 mL) was added and the reaction was warmed to 60° C. with stirring. A solution of aldrithiol-2 (368 mg, 1.67 mmol, 7 eq.), triphenylphosphine (438 mg, 1.67 mmol, 7 eq.) and triethylamine (400 µL, 2.86 mmol, 12 eq.) in 1.5 mL pyridine was added. The reaction was stirred at 60° C. under N$_2$ overnight. The reaction was then concentrated to a solid and placed under high vacuum for 1 hour to remove residual pyridine. Column chromatography (SiO$_2$, 0-15% MeOH in dichloromethane) provided the desired product as a pale yellow solid (70 mg, 0.131 mmol, 55%).

$^1$H NMR (300 MHz, CD$_3$OD) d=7.90 (d, J=6.7 Hz, 1H), 7.29 (m, 2H), 7.16 (m, 1H), 7.05 (m, 2H), 4.44 (m, 2H), 4.32 (m, 2H), 4.04 (m, 3H), 3.94 (m, 4H), 1.86 (m, 2H), 1.60 (m, 2H), 1.35 (bm, 4H), 1.23 (m, 2H), 1.06 (t, J=7.5 Hz, 3H), 0.92 (m, 3H).

$^{31}$P NMR (75 MHz, CD$_3$OD) d 22.885, 24.02 (diastereomers).

LC/MS: r.t.=2.18 min (3.5 min run), mass=535 (M+1).

The diastereomers were separated by preparative Chiral HPLC, using a Chiral-Pak AS column and 50:50 methanol:ethanol mobile phase.

Isomer B (52b) (the first isomer to elute from the column) was isolated after solvent removal as a white solid (70 mg).

$^1$H NMR (300 MHz, CD$_3$OD) d=7.88 (s, 1H), 7.28 (m, 2H), 7.15 (m, 1H), 7.05 (m, 2H), 4.44 (t, J=6.7 Hz, 2H), 4.32 (t, J=5.0 Hz, 2H), 4.05 (m, 3H), 3.90 (m, 4H), 1.86 (m, 2H), 1.58 (m, 2H), 1.35 (m, 4H), 1.23 (d, J=7.3 Hz, 3H), 1.06 (t, J=7.5 Hz, 3H), 0.91 (t, J=7.3 Hz, 3H).
$^{31}$P NMR (75 MHz, CD$_3$OD) d 24.02.
LC/MS: r.t.=2.18 min (3.5 min run), mass=535 (M+1).

Isomer A (52a) (the second isomer to elute from the column) was isolated after solvent removal as a white solid (65 mg).
$^{1}$H NMR (300 MHz, CD$_3$OD) d=7.90 (s, 1H), 7.29 (m, 2H), 7.16 (m, 1H), 7.05 (m, 2H), 4.44 (t, J=6.7 Hz, 2H), 4.33 (t, J=5.0 Hz, 2H), 4.05 (m, 3H), 3.94 (m, 4H), 1.86 (m, 2H), 1.60 (m, 2H), 1.35 (m, 2H), 1.23 (d, J=7.3 Hz, 3H), 1.06 (t, J=7.5 Hz, 3H), 0.91 (t, J=7.3 Hz, 3H).
$^{31}$P NMR (75 MHz, CD$_3$OD) d 22.88.
LC/MS: r.t.=2.18 min (3.5 min run), mass=535 (M+1).

Compounds 53 through 57 were prepared from Example 1 by the same method as described in Example 52.

Example 53

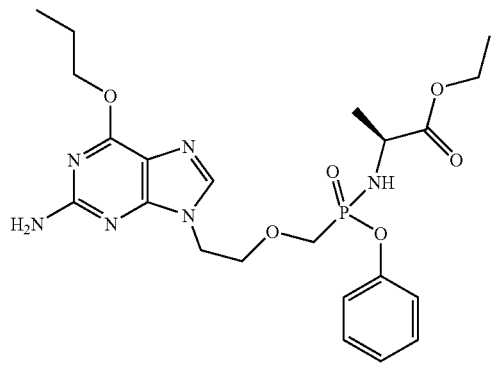

(53)

Compound (53) was synthesized in a manner analogous to Example 52 and was isolated by column chromatography (SiO$_2$, 0-15% MeOH in dichloromethane) as an off-white solid (15 mg, 0.030 mmol, 10%).
$^{1}$H NMR (300 MHz, CD$_3$OD) d=7.89 (d, J=6.1 Hz, 1H), 7.28 (m, 2H), 7.15 (m, 1H), 7.05 (m, 2H), 4.45 (m, 2H), 4.33 (m, 2H), 4.08 (m, 2H), 3.95 (m, 5H), 1.87 (m, 2H), 1.23 (m, 6H), 1.06 (t, J=7.5 Hz, 3H).
$^{31}$P NMR (75 MHz, CD$_3$OD) d 22.895, 24.04 (diastereomers).
LC/MS: r.t=2.14 min (3.5 min run), mass=507 (M+1).

The diastereomers were separated by preparative Chiral HPLC, using a Chiral-Pak OJ column and 70:30 heptane:isopropanol mobile phase.
Isomer B (53b)
Chiral preparative HPLC afforded Isomer B (the first isomer to elute from the column) as a white solid, 71 mg.
$^{1}$H NMR (300 MHz, CD$_3$OD) d=7.88 (s, 1H), 7.26 (m, 2H), 7.15 (m, 1H), 7.04 (m, 2H), 4.45 (t, J=6.6 Hz, 2H), 4.31 (t, J=51 Hz, 2H), 4.09 (m, 2H), 3.90 (m, 5H), 1.86 (m, 2H), 1.21 (m, 6H), 1.06 (t, J=7.5 Hz, 3H).
$^{31}$P NMR (75 MHz, CD$_3$OD) d 22.89.
LC/MS: r.t.=2.14 min (3.5 min run), mass=507 (M+1).
Isomer A (53a)
Chiral preparative HPLC afforded Isomer A (the second isomer to elute from the column) as a white solid, 51 mg.
$^{1}$H NMR (300 MHz, CD$_3$OD) d=7.91 (s, 1H), 7.28 (m, 2H), 7.16 (m, 1H), 7.06 (m, 2H), 4.44 (t, J=6.7 Hz, 2H), 4.33 (t, J=5.0 Hz, 2H), 4.07 (m, 2H), 3.94 (m, 5H), 1.86 (m, 2H), 1.21 (m, 6H), 1.06 (t, J=7.4 Hz, 3H).
$^{31}$P NMR (75 MHz, CD$_3$OD) d 24.04.
LC/MS: r.t.=2.14 min (3.5 min run), mass=507 (M+1).

Example 54

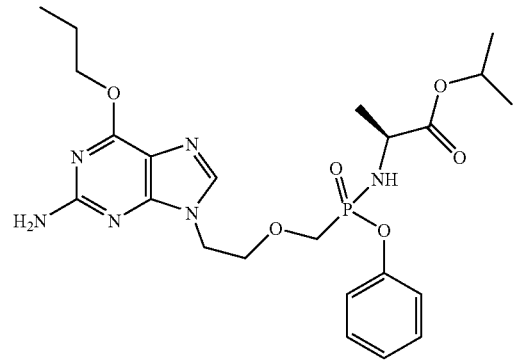

(54)

Compound (54) was synthesized in a manner analogous to Example 52 and was isolated by column chromatography (SiO$_2$, 0-15% MeOH in dichloromethane) as a tan solid (15 mg, 0.029 mmol, 10%).
$^{1}$H NMR (300 MHz, CD$_3$OD) d=7.89 (d, J=5.9 Hz, 1H), 7.27 (m, 2H), 7.15 (m, 1H), 7.05 (m, 2H), 4.90 (m, 1H), 4.43 (m, 2H), 4.31 (m, 2H), 3.95 (m, 5H), 1.87 (m, 2H), 1.22 (m, 9H), 1.06 (t, J=7.5 Hz, 3H).
$^{31}$P NMR (75 MHz, CD$_3$OD) d 22.96, 24.05 (diastereomers).
LC/MS: r.t=2.24 min (3.5 min run), mass=521 (M+1).

Example 55

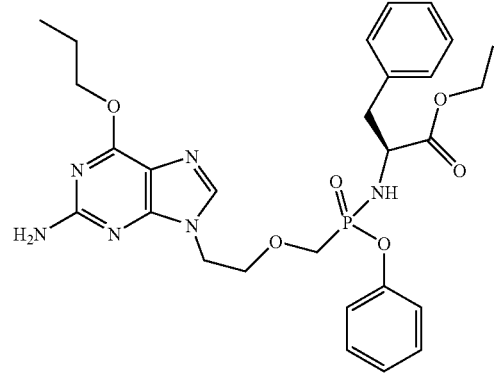

(55)

Compound (55) was synthesized in a manner analogous to Example 52 and isolated by column chromatography (SiO$_2$, 0-15% MeOH in dichloromethane) as a yellow solid (25 mg, 0.043 mmol, 14%).
$^{1}$H NMR (300 MHz, CD$_3$OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).
$^{31}$P NMR (75 MHz, CD$_3$OD) d 23.21, 23.71 (diastereomers).
LC/MS: r.t=2.40 min (3.5 min run), mass=583 (M+1).

Example 56

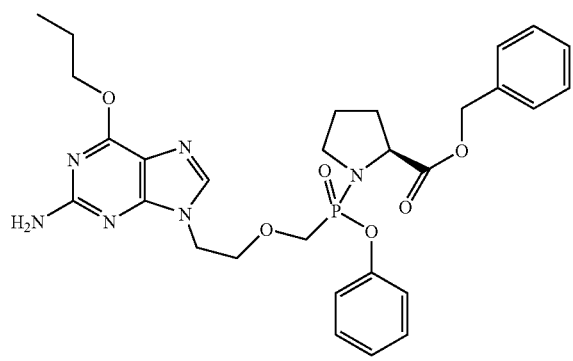

(56)

Compound (56) was synthesized in a manner analogous to Example 52 and was isolated by column chromatography (SiO$_2$, 0-15% MeOH in dichloromethane) as a colorless glassy solid (11 mg, 0.0185 mmol, 4%).

$^1$H NMR (300 MHz, CD$_3$OD) d=7.88 (s=1H), 7.33 (bm, 7H), 7.16 (m, 1H), 7.03 (m, 2H), 5.10 (m, 2H), 4.43 (t, J=6.6 Hz, 2H), 4.32 (m, 3H), 4.05 (m, 1H), 3.85 (m, 4H), 3.07 (m, 2H), 2.03 (m, 1H), 1.5 (m, 4H), 1.05 (t, J=7.5 Hz, 3H).

$^{31}$P NMR (75 MHz, CD$_3$OD) d 21.84, 22.72 (diastereomers).

LC/MS: r.t=2.23 min (3.5 min run), mass=595 (M+1).

Example 57

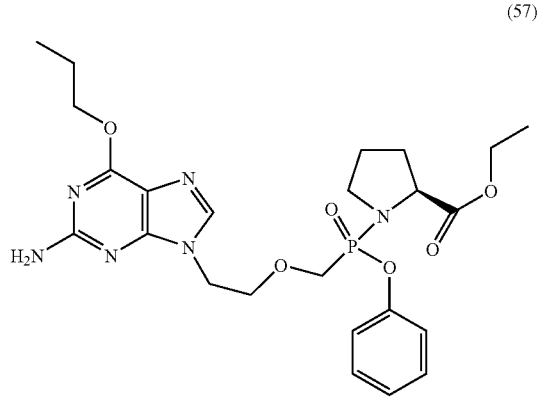

(57)

Compound (57) was synthesized in a manner analogous to Example 52 and was isolated by column chromatography (SiO$_2$, 0-15% MeOH in dichloromethane) as a colorless glassy solid (10 mg, 0.019 mmol, 6%).

$^1$H NMR (300 MHz, CD$_3$OD) d=7.89 (d, J=9 Hz, 1H), 7.31 (m, 2H), 7.17 (m, 1H), 7.04 (m, 2H), 4.44 (m, 2H), 4.33 (m, 3H), 4.12 (m, 3H), 3.97 (m, 4H), 3.10 (m, 2H), 2.00 (m, 1H), 1.85 (m, 6H), 1.23 (m, 3H), 1.06 (t, J=7.5 Hz, 3H).

$^{31}$P NMR (75 MHz, CD$_3$OD) d 21.83, 22.79 (diastereomers),

LC/MS: r.t=2.00 min (3.5 min run), mass=533 (M+1).

Example 58 was prepared from (8) by the same method as described in Example 52.

Example 58

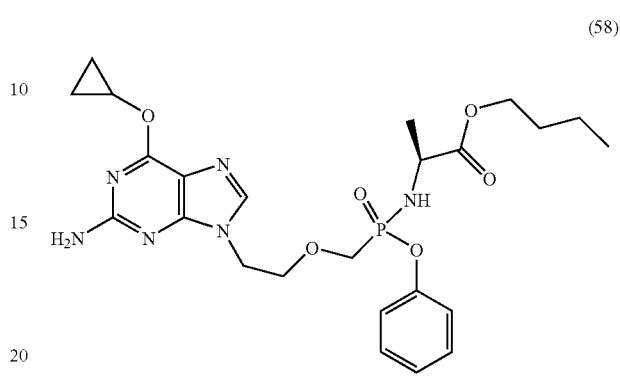

(58)

Compound (58) was synthesized in a manner analogous to Example 52 and was isolated by column chromatography (SiO$_2$, 0-15% MeOH in dichloromethane) as a white solid (62 mg, 0.116 mmol, 56%).

$^1$H NMR (300 MHz, CD$_3$OD) d=7.89 (d, J=6.4 Hz, 1H), 7.29 (m, 2H), 7.15 (m, 1H), 7.05 (m, 2H), 4.55 (m, 1H), 4.33 (m, 2H), 4.08 (m, 2H), 3.96 (m, 5H), 1.58 (m, 2H), 1.37 (m, 2H), 1.23 (d, J=7.1 Hz, 3H), 0.93 (m, 3H), 0.83 (m, 4H).

$^{31}$P NMR (75 MHz, CD$_3$OD) d 22.87, 24.004 (diastereomers).

LC/MS: r.t=2.30 min (3.5 min run), mass=533 (M+1).

Example 59

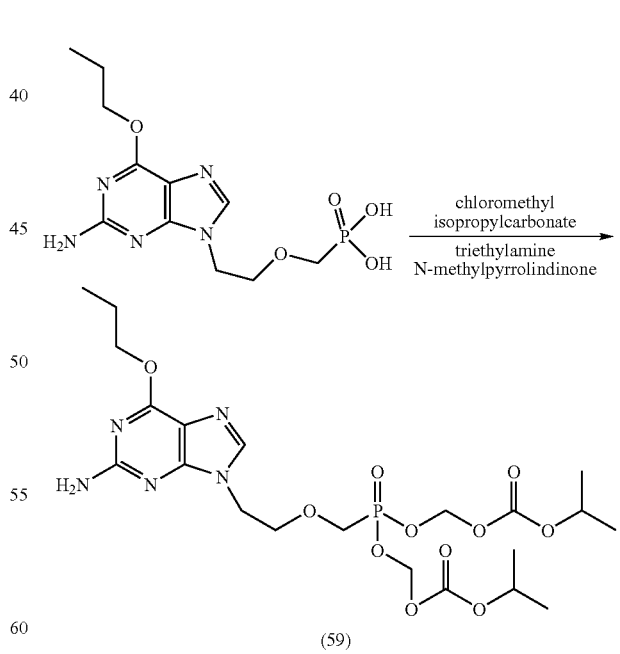

(59)

[[2-(2-Amino-6-chloro-9H-purin-9-yl)ethoxy]methyl]-phosphonic acid, bis(1-methylethyl) ester (140 mg, 0.423 mmol, 1 eq.) was weighed into a small flask and purged with N$_2$. N-methylpyrrolidinone (1 mL) and triethylamine (295 µL, 2.115 mmol, 5 eq.) were added and the reaction was warmed to 60° C. with stirring. Once a clear solution had formed, chloromethyl isopropyl carbonate (324 mg, 2.115 mmol, 5 eq.) was added. The reaction was stirred at 60° C. under N₂ for three hours and then partitioned between ethyl acetate and water. The aqueous layer washed three times with ethyl acetate, and the combined organic layers were washed once with brine and concentrated to an oil that was placed under high vacuum for 1 hour. Column chromatography (SiO₂, 0-15% MeOH in dichloromethane) provided the desired product (59) as a pale yellow oil (12 mg, 0.021 mmol, 5%).

¹H NMR (300 MHz, CD₃OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

³¹P NMR (75 MHz, CD₃OD) d 21.29.

LC/MS: r.t.=2.34 min (3.5 min run), mass=564 (M+1).

Example 60 was prepared from (2) by the same method as described in Example 59.

Example 60

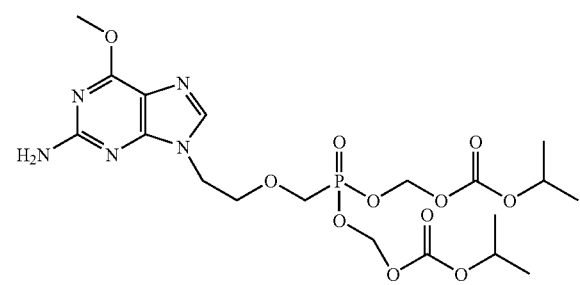
(60)

Example 60 was isolated by column chromatography (SiO₂, 0-15% MeOH in dichloromethane) as a colorless viscous oil (10 mg, 0.019 mmol, 10%).

¹H NMR (300 MHz, CD₃OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

³¹P NMR (75 MHz, CD₃OD) d 21.28.

LC/MS: r.t=2.07 min (3.5 min run), mass=536 (M+1).

Example 61 was prepared from the compound of Example 3 by the same method as described in Example 59.

Example 61

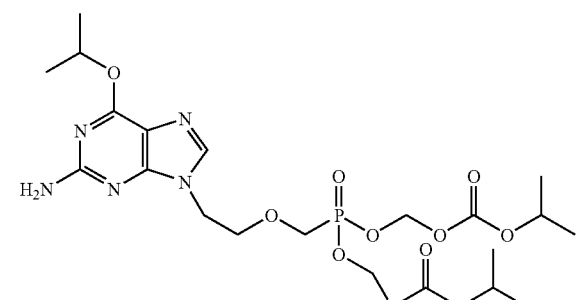
(61)

(61) was isolated by column chromatography (SiO₂, 0-15% MeOH in dichloromethane) as a colorless viscous oil (10 mg, 0.019 mmol, 10%).

¹H NMR (300 MHz, CD₃OD) d=8.20 (s, 1H), 4.48 (t, J=6.7 Hz, 2H), 4.36 (t, J=4.9 Hz, 2H), 3.91 (t, J=4.9 Hz, 2H), 3.70 (d, J=8.9 Hz, 2H), 1.87 (m, 2H), 1.07 (t, J=7.5 Hz, 3H).

³¹P NMR (75 MHz, CD₃OD) d 21.28.

LC/MS: r.t=2.07 min (3.5 min run), mass=536 (M+1).

Example 62

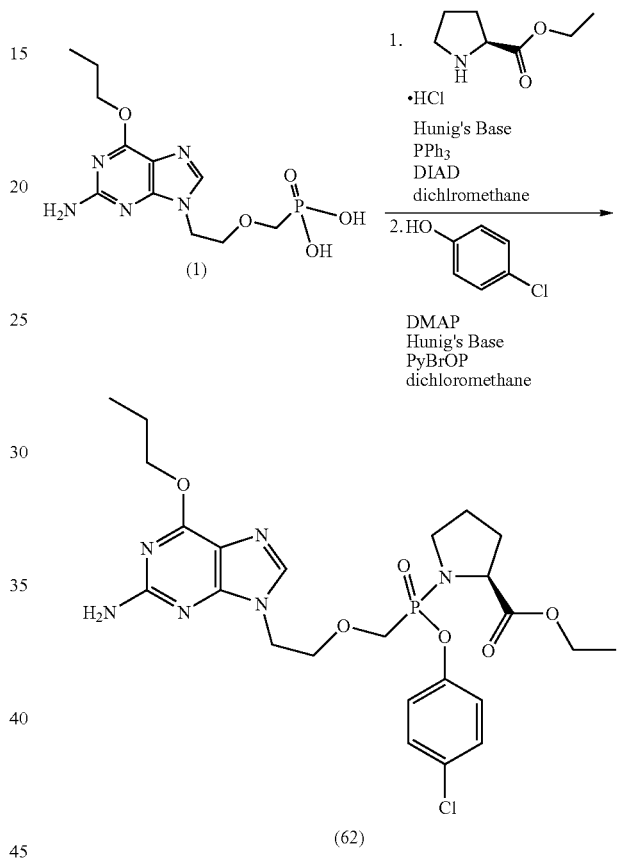
(62)

Triphenylphosphine (60 mg, 0.23 mmol, 1.25 eq.) was weighed into a small flask and purged with N₂ then dissolved in 2 mL dichloromethane. Diisopropyl azodicarboxylate (DIAD, 46 mg, 0.23 mmol, 1.25 eq.) was added next and then was added L-proline ethyl ester hydrochloride (165 mg, 0.92 mmol, 5 eq.). N,N-diisopropylethylamine (200 uL, ~1.1 mmol, ~6 eq) was added and the reaction mixture stirred 15 minutes. [[2-(2-Amino-6-chloro-9H-purin-9-yl)ethoxy]methyl]-phosphonic acid, bis(1-methylethyl) ester (61 mg, 0.184 mmol, 1 eq.) was weighed into a small flask and purged with N₂. The mixture of reagents was then quickly added to the flask containing [[2-(2-amino-6-chloro-9H-purin-9-yl)ethoxy]methyl]-phosphonic acid, bis(1-methylethyl) ester and the reaction was stirred at room temperature under N₂ for 2 hours. The reaction was then concentrated to an oil, redissolved in methanol, and the intermediate was isolated from this solution by reverse-phase HPLC as a white solid (30 mg, 0.066 mmol, 36%). P-chlorophenol (17 mg, 0.132 mmol, 2 eq.), DMAP (4 mg, 0.033 mmol, 0.5 eq.), and PyBroP (62 mg, 0.132 mmol, 2 eq.) were all weighed into the flask containing the intermediate. This flask was purged with N₂ and then 1 mL dichloromethane and N,N-diisopropylethylamine (69 uL, 0.396 mmol, 6 eq) were added. The reaction was stirred at room temperature overnight. The reaction was then concentrated to an oil, and redissolved in methanol. Compound 62 was isolated from this solution by reverse-phase HPLC as a white solid (8 mg, 0.014 mmol, 8%).

$^1$H NMR (300 MHz, CD$_3$OD) d=7.89 (d, J=9 Hz, 1H), 7.30 (m, 2H), 7.11 (m, 2H), 4.44 (m, 2H), 4.33 (m, 2H), 4.13 (m, 3H), 3.96 (m, 3H), 3.17 (m, 2H), 2.01 (m, 1H), 1.86 (m, 6H), 1.23 (m, 3H), 1.06 (t, J=7.5 Hz, 3H).

$^{31}$P NMR (75 MHz, CD$_3$OD) d 22.33, 23.31 (diastereomers).

LC/MS: r.t=2.98 min (6 min run), mass=568 (M+1).

Example 63

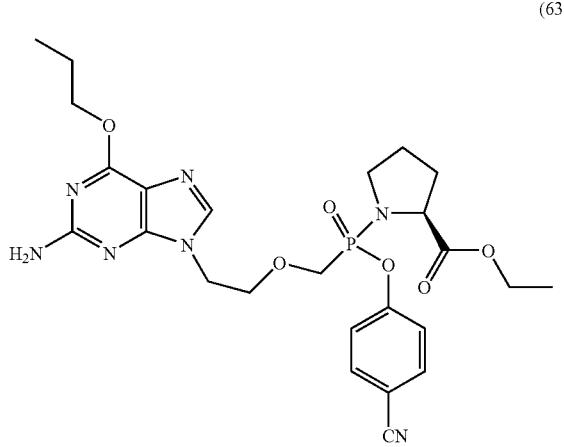

(63)

Compound (63) was prepared by the same method as described in Example 62 except that p-cyanophenol was substituted for p-chlorophenol. Compound (63) was isolated by reverse-phase HPLC as a white solid (31 mg, 0.056 mmol, 18%).

$^1$H NMR (300 MHz, CD$_3$OD) d=7.90 (d, J=9 Hz, 1H), 7.70 (d, J=9 Hz, 2H), 7.31 (m, 1H), 7.20 (m, 1H), 4.44 (m, 2H), 4.33 (m, 2H), 4.12 (m, 4H), 4.00 (m, 2H), 3.20 (m, 2H), 2.02 (m, 1H), 1.85 (m, 6H), 1.23 (m, 3H), 1.06 (t, J=7.5 Hz, 3H).

$^{31}$P NMR (75 MHz, CD$_3$OD) d 22.66, 23.72 (diastereomers).

LC/MS: r.t=2.98 min (6 min run), mass=558 (M+1).

Example 64

Cytostatic Cell Culture Assay (GI$_{50}$)

The assay is based on quantification of cell counts by a colorimetric detection of the cell associated proteins. The assay relies on the ability of sulforhodamine B (SRB) to bind to protein components of cells that have been fixed to tissue-culture plates by trichloroacetic acid (TCA). SRB is a bright-pink aminoxanthene dye with two sulfonic groups that bind to basic amino-acid residues under mild acidic conditions, and dissociate under basic conditions. As the binding of SRB is stoichiometric, the amount of dye extracted from stained cells is directly proportional to the cell mass.

Cell lines: All cell lines were obtained from ATCC (Manassas, Va.). Cultivation media containing Glutamax, and trypsin were purchased from Invitrogen (Carlsbad, Calif.). Doxorubicin, Clofarabine, TCA and SRB were from Sigma-Aldrich (St. Louis, Mo.). Gemcitabine was obtained from Moravek Biochemicals (Brea, Calif.)

Assay Protocol:

1. Maintain cell lines in the media listed in Table 1. Trypsinize the sub-confluent cells, count them, and adjust the cell concentrations according to the cell counts listed in Table 1.
2. Distribute the cells into the 96-well plates in 150 μL of media. Incubate the plates overnight in humidified CO$_2$ incubator at 37° C.
3. Fix one plate of each cell line with TCA. Discard the cultivation media from the plates by flicking them gently and add 100 ul cold 10% (vol/vol) TCA to each well. Incubate the plates at 4 degree refrigerator for 1 hour. Discard TCA from the plates by flicking them gently. Rinse plates four times in a washing basin containing tap water. Store the plates at room temperature. These plates represent cell counts on day zero.
4. Prepare a set of medium solutions containing various concentrations of tested compounds by making 5-fold serial dilutions in 96-well plate. Add 50 μL of the diluted compounds per well. Include controls with untreated cells and cells treated with doxorubicin, clofarabine and gemcitabine.
5. Incubate the plates for 5 days at 37° C.
6. Fix the plates with TCA. Discard the cultivation media from the plates by flicking them gently and add 100 ul cold 10% (vol/vol) TCA to each well. Incubate the plates at 4 degree refrigerator for 1 hour. Discard TCA from the plates by flicking them gently. Rinse plates four times in a washing basin containing tap water.
7. Remove excess water by tapping the plates face down, gently on a paper towel. Allow the plates to air-dry at room temperature.
8. Add 100 ul of 0.057% SRB solution in 1% (vol/vol) acetic acid to each well of the plates fixed with TCA on day zero and five. Leave at room temperature for 30 minutes.
9. Flick the plates gently to discard SRB. Rinse the plates four times with 1% (vol/vol) Acetic Acid.
10. Store the plates at 37 degree incubator to facilitate faster drying.
11. Once the plates are completely dry, add 200 ul of 10 mM Tris base solution (pH 10.5) to each well. Leave at room temperature for 30 minutes for SRB to solubilize.
12. Measure the OD at 500 nm in a microplate reader
13. Calculate the percentage of cell-growth inhibition using the next formula:

% of control cell growth=100×($OD_{sample}$-mean $OD_{day0}$)/($OD_{neg\ control}$-mean $OD_{day0}$)

For GI$_{50}$ determination, plot a dose-response curve between the compound concentration and percent of growth inhibition. GI$_{50}$ values can be derived by fitting dose-response curves using sigmoidal dose response equation.

| CELL LINE | Medium | Seeding Density | Dissociation Agent |
|---|---|---|---|
| HCT 116 | RPMI, 10% FBS, 1X Pen/Strep | 800 cells/well | Trypsin |
| HCT 15 | RPMI, 10% FBS, 1X Pen/Strep | 1600 cells/well | Trypsin |
| BT549 | RPMI, 10% FBS, 1X Pen/Strep | 4000 cells/well | Tryple Express (Invitrogen) |

| CELL LINE | Medium | Seeding Density | Dissociation Agent |
|---|---|---|---|
| HS 578 | RPMI, 10% FBS, 1X Pen/Strep | 4000 cells/well | Tryple Express (Invitrogen) |
| PC3 | F12K, 10% FBS, 1X Pen/Strep | 2500 cells/well | Trypsin |
| DU145 | MEM, 10% FBS, 1X Pen/Strep | 800 cells/well | Trypsin |
| H23 | RPMI, 10% FBS, 1X Pen/Strep | 6000 cells/well | Trypsin |
| A549 | RPMI, 10% FBS, 1X Pen/Strep | 1500 cells/well | Trypsin |

The following table shows that the compounds of the present invention inhibit cancer cell growth.

| | GI50 (μM) | | | | | | | |
|---|---|---|---|---|---|---|---|---|
| Compound | HCT-116 | HCT-15 | BT-549 | Hs-578 | PC3 | Du-145 | NCI-H23 | A549 |
| Example 1 | 1.10 | 0.886 | 0.900 | 3.81 | 1.10 | 0.076 | 0.287 | 1.24 |
| Example 2 | 5.9 | 4.65 | 4.87 | 2.01 | 3.70 | 0.475 | 0.589 | 2.42 |
| Example 3 | 2.44 | 2.53 | 2.48 | 2.45 | 1.38 | 0.177 | 0.551 | 2.98 |
| Example 4 | 3.13 | 2.98 | 3.76 | 3.32 | 1.44 | 0.235 | 0.633 | 4.54 |
| Example 5 | 3.59 | 2.44 | 2.00 | 2.59 | 2.48 | 0.223 | 0.639 | 2.84 |
| Example 6 | >10 | 13 | 17 | 11 | 3.01 | 0.439 | 6.0 | >10 |
| Example 7 | 2.45 | 2.61 | 2.57 | 1.57 | 0.595 | 0.101 | 0.596 | 3.36 |
| Example 8 | 5.4 | 4.14 | 2.71 | 2.83 | 2.83 | 0.536 | 0.675 | 2.82 |
| Example 9 | 1.72 | 1.22 | 1.55 | 1.55 | 0.955 | 0.077 | 0.359 | 1.83 |
| Example 10 | 1.79 | 2.38 | 2.99 | 2.26 | 1.01 | 0.054 | 0.603 | 3.06 |
| Example 11 | 11 | >10 | >10 | 5.1 | 3.76 | 0.805 | 1.98 | 11 |
| Example 12 | 38 | 38 | 70 | 18 | 6.1 | 1.23 | 2.19 | 35 |
| Example 13 | 0.013 | 1.09 | 0.061 | 0.105 | 0.011 | 0.002 | 0.004 | 0.052 |
| Example 14 | 0.488 | >10 | 0.266 | 0.202 | 0.275 | 0.028 | 0.029 | 0.381 |
| Example 15 | 0.018 | 1.28 | 0.102 | 0.112 | 0.026 | 0.003 | 0.007 | 0.081 |
| Example 16 | 1.32 | >10 | 1.83 | 0.870 | 0.591 | 0.067 | 0.092 | 0.736 |
| Example 17 | 0.004 | 0.336 | 0.017 | 0.005 | 0.006 | 0.001 | 0.002 | 0.005 |
| Example 18 | 9.0 | 24 | 7.6 | 9.1 | 5.4 | 1.28 | 2.33 | 9.9 |
| Example 19 | 0.005 | 0.467 | 0.053 | 0.005 | 0.010 | 0.001 | 0.001 | 0.004 |
| Example 20 | 0.264 | 2.35 | 0.167 | 0.132 | 0.111 | 0.027 | 0.030 | 0.530 |
| Example 21 | 0.041 | 6.7 | 0.033 | 0.017 | 0.026 | 0.002 | 0.002 | 0.128 |
| Example 22 | 0.194 | >10 | 0.116 | 0.082 | 0.121 | 0.035 | 0.038 | 0.640 |
| Example 23 | 0.028 | 2.47 | 0.007 | 0.004 | 0.011 | 0.001 | 0.003 | 0.317 |
| Example 24 | 0.979 | >10 | 0.386 | 0.452 | 0.634 | 0.138 | 0.124 | 3.82 |
| Example 25 | 0.043 | 1.49 | 0.015 | 0.008 | 0.016 | 0.002 | 0.002 | 0.450 |
| Example 26 | 0.119 | 1.95 | 0.067 | 0.097 | 0.081 | 0.002 | 0.009 | 1.05 |
| Example 27 | 0.023 | 2.37 | 0.033 | 0.053 | 0.013 | 0.002 | 0.004 | 0.026 |
| Example 28 | 0.859 | >10 | 0.573 | 0.380 | 0.381 | 0.047 | 0.028 | 0.736 |
| Example 29 | 0.988 | >10 | 1.11 | 0.378 | 0.325 | 0.029 | 0.032 | 0.387 |
| Example 30 | 0.027 | 1.90 | 0.023 | 0.017 | 0.103 | 0.003 | 0.010 | 0.036 |
| Example 31 | 0.006 | 0.604 | 0.020 | 0.005 | 0.016 | 0.001 | 0.002 | 0.006 |
| Example 32 | 22 | >10 | >10 | 6.6 | 8.0 | 1.49 | 2.62 | 11 |
| Example 33 | 0.652 | >10 | 0.423 | 0.243 | 0.190 | 0.018 | 0.019 | 0.762 |
| Example 34 | 0.055 | 2.65 | 0.195 | 0.031 | 0.021 | 0.004 | 0.005 | 0.041 |
| Example 35 | 0.140 | 8.9 | 0.145 | 0.046 | 0.028 | 0.005 | 0.014 | 0.187 |
| Example 36 | 0.007 | 0.869 | 0.120 | 0.011 | 0.003 | 0.000 | 0.002 | 0.013 |
| Example 37 | 0.509 | >10 | 0.292 | 0.198 | 0.146 | 0.023 | 0.031 | 0.458 |
| Example 38 | 0.012 | 0.799 | 0.053 | 0.020 | 0.002 | 0.001 | 0.002 | 0.017 |
| Example 39 | 1.48 | >10 | 2.65 | 0.697 | 0.141 | 0.102 | 0.198 | 3.19 |
| Example 40 | 2.44 | >10 | 1.78 | 0.276 | 0.109 | 0.074 | 0.252 | 8.8 |
| Example 41 | 0.133 | 6.4 | 0.301 | 0.062 | 0.010 | 0.001 | 0.011 | 0.195 |
| Example 42 | 0.430 | 10 | 0.104 | 0.162 | 0.237 | 0.010 | 0.015 | 1.71 |
| Example 43 | 0.011 | 1.52 | 0.017 | 0.032 | 0.032 | 0.000 | 0.001 | 0.102 |
| Example 44 | 0.154 | 9.1 | 0.016 | 0.026 | 0.183 | 0.003 | 0.227 | 1.25 |
| Example 45 | 0.372 | 8.3 | 0.269 | 0.174 | 0.113 | 0.008 | 0.022 | 0.451 |
| Example 46 | 0.269 | 6.3 | 0.286 | 0.096 | 0.085 | 0.017 | 0.023 | 0.474 |
| Example 47 | 0.055 | 1.81 | 0.326 | 0.050 | 0.008 | 0.001 | 0.004 | 0.103 |
| Example 48 | 2.52 | >10 | 1.71 | 0.976 | 0.372 | 0.108 | 0.061 | 4.09 |
| Example 49 | 0.109 | 5.1 | 0.050 | 0.025 | 0.003 | 0.001 | 0.002 | 0.368 |
| Example 50 | 3.07 | >10 | 1.62 | 0.308 | 0.608 | 0.250 | 0.118 | 3.70 |
| Example 51 | 0.850 | 8.5 | 0.527 | 0.096 | 0.214 | 0.256 | 0.263 | 1.67 |
| Example 52a | 0.043 | 0.553 | 0.105 | 0.013 | 0.008 | 0.0003 | 0.0009 | 0.048 |
| Example 52b | 0.011 | 0.517 | 0.100 | 0.002 | 0.003 | 0.0003 | 0.001 | 0.015 |
| Example 53a | 0.154 | 2.11 | 0.249 | 0.062 | 0.031 | 0.002 | 0.005 | 0.268 |
| Example 53b | 0.329 | 2.04 | 0.564 | 0.177 | 0.180 | 0.014 | 0.070 | 0.647 |
| Example 54 | 0.840 | 2.77 | 1.77 | 0.894 | 0.472 | 0.065 | 0.067 | 0.317 |
| Example 55 | 0.047 | 0.815 | 0.756 | 0.149 | 0.059 | 0.004 | 0.009 | 0.080 |
| Example 56 | 1.93 | 3.86 | 1.09 | 1.49 | 1.25 | 0.722 | 0.389 | 2.13 |
| Example 57 | 1.61 | 5.2 | 1.12 | 1.11 | 0.696 | 0.372 | 0.241 | 2.42 |
| Example 58 | 0.114 | 1.03 | 0.585 | 0.042 | 0.060 | 0.001 | 0.003 | 0.204 |
| Example 59 | 0.118 | 0.534 | 0.045 | 0.061 | 0.040 | 0.002 | 0.010 | 0.168 |

-continued

| Compound | HCT-116 | HCT-15 | BT-549 | Hs-578 | PC3 | Du-145 | NCI-H23 | A549 |
|---|---|---|---|---|---|---|---|---|
| | | | GI50 (µM) | | | | | |
| Example 60 | 0.079 | 0.766 | 0.042 | 0.022 | 0.052 | 0.002 | 0.005 | 0.091 |
| Example 61 | 0.370 | 0.671 | 0.057 | 0.038 | 0.071 | 0.002 | 0.010 | 0.319 |
| Example 62 | 2.79 | 10.0 | 4.44 | 1.07 | 0.044 | 0.001 | 0.049 | 1.87 |
| Example 63 | 0.184 | 3.35 | 0.282 | 0.007 | 0.002 | 0.001 | 0.001 | 0.014 |

Cytotoxicity Cell Culture Assay ($CC_{50}$):

The assay is based on the quantification of cell numbers by measuring the intracellular ATP levels. Ultra-Glo Recombinant Luciferase in the presence of cellular ATP converts beetle luciferin to oxylucifer and luminescence, which is proportional to number of cells, is recorded.

Materials: MT4 cell line was obtained from ATCC (Manassas, Va.). Cultivation media, HEPES, and bovine serum albumine were purchased from Invitrogen (Carlsbad, Calif.). Black 384-well Nunc cell culture plates were from VWR, and Cell Titer-Glo Luminescent Cell Viability assay was purchased from Promega.

Assay Protocol for Determination of $CC_{50}$:

1. Maintain MT-4 cells in RPMI-1640 medium supplemented with 10% fetal bovine serum, 10 mM Hepes and antibiotics.
2. Prepare a set of solutions containing various concentrations of the tested inhibitors by making 5-fold serial dilutions in 384-well plate (20 µl/well) in cultivation medium. Distribute cells into the 384-well plate (2000 cells in 20 µl/well). Include samples with untreated cells as a control.
3. Incubate the cells for 5 days at 37° C., 5% $CO_2$ in humidified incubator.
4. Prepare CellTiter Glo solution by mixing CellTiter-Glo substrate with CellTiter Glo buffer in dark Add 40 µL of the solution to each well.
5. After 3 minutes incubation, read chemiluminescence.
6. Plot the percentage luminescence relative to untreated control and estimate the CC50 value as drug concentration resulting in a 50% inhibition of the cell growth. Consider the luminescence being directly proportional to the cell numbers.

Compounds (1)-(60) were assayed and found to have acceptable toxicity and activity against the tumor cells.

Example 65

Compound (21) was evaluated for efficacy in a dog with naturally occurring non-Hodgkin's lymphoma (NHL). Canine NHL has proven to be a relevant model for preclinical evaluation of new therapeutics, both for initial induction and rescue of drug-resistant relapse (Reference Vail D M, Thamm D H. Spontaneously occurring tumors in companion animals as models for drug development. In: Teisher B A, ed. Anticancer Drug Development Guide. 2nd ed. Totowa (NJ): Humana Press Inc; 2004; 259-286.) Evaluation of novel therapeutic approaches in dogs with spontaneous cancer offers potential benefit to canine patients and a rapid assessment of therapeutic index. Because the tumors arise spontaneously in an immunologically intact host and have greater heterogeneity than passaged cell lines, it is not surprising that responses to standard chemotherapeutic agents in canine malignancies are similar to those of the corresponding tumors in man and that the preclinical results attained may be more predictive of the activity in humans (references; Khanna C, Paoloni M. Translation of new cancer treatments from pet dogs to humans. Nature Rev Cancer. 2008; 8:7-16.; Vail D M, Young K M. Canine lymphoma and lymphoid leukemia. In: Withrow S J, Vail D M, eds. Small Animal Clinical Oncology. 4th Ed. St. Louis (MO): Saunders; 2007. p. 699-733.) Non-Hodgkin's lymphoma in dogs represents a relatively homogenous population with respect to histological type as defined by the REAL/WHO or NCI-Working Formulation schema (i.e., 85% are medium- to high-grade B-cell NHL) with the majority being diffuse large B-cell lymphoma (reference Jacobs R M, Messick J B, Valli V E. Tumors of the hemolymphatic system. In: Meuten D J, editor. Tumors in Domestic Animals. 4th Ed. Ames (IA): Iowa State Press; 2002:119-198).

Cancers in pet dogs are characterized by tumor growth over long periods of time in the setting of an intact immune system, inter-individual and intra-tumoral heterogeneity, the development of recurrent or resistant disease, and metastasis to relevant distant sites. In these ways, dog cancers capture the 'essence' of the problem of human cancer in a manner not possible with other animal model systems. For many of these cancers, strong similarities to human cancers are seen, including histological appearance, tumor genetics, biological behavior and response to conventional therapies. The compressed course of cancer progression seen in dogs allows timely assessment of new cancer therapies.

Compound (21) was administered at a dose of 0.3 mg/kg of body weight by 30 minute IV infusion in Sterile Saline Injection (0.9% sodium chloride for injection) (total volume 2 ml/kg or 100 ml) once every 21 days to a dog that had non-Hodgkin's lymphoma involving multiple lymphnodes. Diagnosis was confirmed by histological evaluation of the tumor. The effect of treatment on the tumor was measured using the Response Evaluation Criteria in Solid Tumors (RECIST) Guideline (Therasse et al 2000). The size of the tumors and response to treatment was evaluated by in these peripherally accessible lymph nodes, by measuring the longest dimension using callipers and evaluating changes in the individual tumor measurement and their sums. The response to treatment is shown by a significant reduction in tumor size starting on Day 7 after the first treatment and continuing with continued improvement to day 42. The reduction in tumor size, overall sum of all tumors, was characterized as a Partial Response (PR) if at least a 30% decrease in the sum of the LD of target lesions, taking as reference the baseline sum, and as a Complete Response (CR) if lymphnodes returned to a size within normal limits. Confirmation was done by cytological examination of an aspirated biopsy to confirm the absence of tumor cells.

Treatment with Compound (21) in this dog with non-Hodgkin's lymphoma resulted in a Partial Response after one treatment and with continued treatment resulted in a Complete Response with complete elimination of the tumor.

Dog Treated with Compound (21)

| Lymphnodes | Treatment #1 0.3 mg/kg Day 0 Pre treatment | Day 1 | Day 7 | Day 14 | Treatment #2 0.3 mg/kg Day 21 | Day 28 | Treatment #3 0.3 mg/kg Day 42 |
|---|---|---|---|---|---|---|---|
| L SMLN | 3.1 | 2.0 | 1.1 | 1.0 | 2.3 | 1.5 | WNL** |
| R SMLN | 2.9 | 3.1 | 1.0 | 1.0 | 2.0 | 1.0 | WNL |
| L PSLN | 5.0 | 3.9 | 1.0 | 1.2 | 2.8 | 1.5 | WNL |
| R PSLN | 3.6 | 3.6 | 1.0 | 1.0 | 2.7 | 1.5 | WNL |
| L PopLN | 2.3 | 2.1 | 1.6 | 1.0 | 1.3 | | WNL |
| Sum (cm) | 16.9 | 14.7 | 5.7 | 5.2 | 11.1 | 5.5 | |
| Change | | −2.2 | −11.2 | −11.7 | −5.8 | −11.4 | |
| % change | −13.0 | −66.3 | −69.2 | −34.3 | −67.5 | −100% | |
| Response | SD | PR | PR | PR | PR | CR | |

**WNL refers to when a lymph node is decreased to a size considered within normal ranges for that node.

| Abbreviations | |
|---|---|
| ATCC | American Type Culture Colection |
| DMF | dimethylformamide |
| DMSO | dimethylsulfoxide |
| dt | doublet of triplets |
| Et | ethyl |
| EDTA | ethylenediaminetetraacetic acid |
| FAB | fast atom bombardment |
| gem | geminal |
| HR | high resolution |
| i | ipso |
| IR | infrared spectroscopy |
| m | multiplet |
| m | meta |
| Me | methyl |
| MeOH | methanol |
| MeONa | sodium methoxide |
| MS | mass spectrometry |
| ν | wave number |
| NMR | nuclear magnetic resonance |
| o | ortho |
| p | para |
| Ph | phenyl |
| PPh$_3$ | triphenylphosphine |
| Py | pyridyl |
| pyrr | pyrrolyl |
| q | quartet |
| rel. | relative |
| RT | room temperature |
| s | singlet |
| sat. | saturated |
| sol. | solution |
| t | triplet |
| TBS | tert-butyldimethylsilyl |
| td | triplet of doublets |
| TDA-1 | tris[2-(2-methoxyethoxy)ethyl]amine |
| THF | tetrahydrofuran |
| TFA | trifluoroacetic acid |
| TPPTS | sodium triphenylphosphine trisulfonate |
| Tr | trityl, triphenylmethyl |
| vic | vicinal |
| HPLC | high-pressure liquid chromatography |
| FBS | fetal bovine serum |
| RPMI | Royal Park Memorial Institute |
| TCA | trichloroacetic acid |
| DIAD | di-isopropyl azodicarboxylate |
| PyBOP | benzotriazol-1-yl-oxytripyrrolidinophosphonium hexafluorophosphate |
| DME | dimethoxyethane |
| DCM | dichloromethane |

-continued

| Abbreviations | |
|---|---|
| ACN | acetonitrile |
| NaHNDS | Sodium hexamethyldisilazide |
| SRB | sulforhodamine B |

We claim:
1. A compound having structure (4)

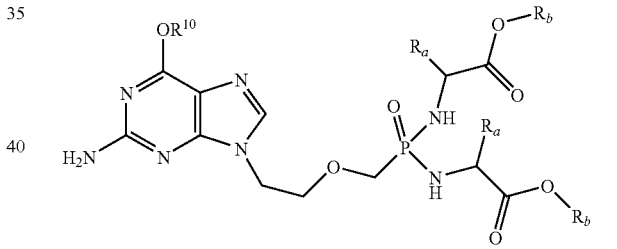

(4)

wherein each $R_a$ independently is $C_1$-$C_4$ alkyl, or benzyl, each $R_b$ independently is $C_1$-$C_4$ alkyl, $R^{10}$ is $C_1$-$C_8$ alkyl, or $C_2$-$C_8$ alkenyl, or $C_2$-$C_8$ alkynyl, wherein $C_1$-$C_8$ alkyl is optionally substituted by one $C_1$-$C_4$ alkoxy group or pharmaceutically acceptable salt or enriched optical isomer thereof.

2. A compound having structure (5)

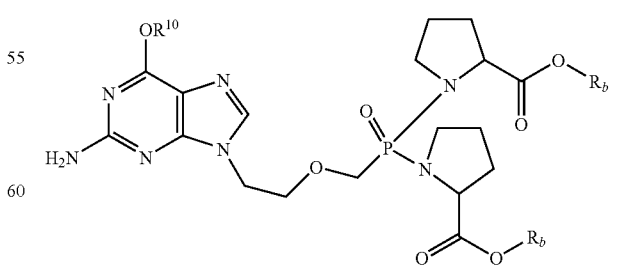

(5)

wherein each $R_b$ independently is $C_1$-$C_4$ alkyl, or benzyl, $R^{10}$ is $C_1$-$C_4$ alkyl; or a pharmaceutically acceptable salt or enriched optical isomer thereof.

3. A compound having structure (7):
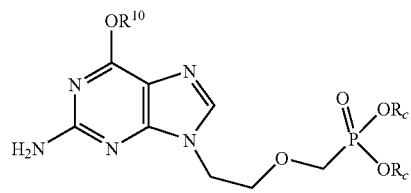
(7)
wherein
each $R_c$ independently is $C_1$-$C_4$ alkyl that is substituted by one $C_1$-$C_4$ alkyl-O—C(O)—O-group; $R^{10}$ is $C_1$-$C_4$ alkyl; or a pharmaceutically acceptable salt or an enriched optical isomer thereof.
4. A compound selected from the group consisting of:
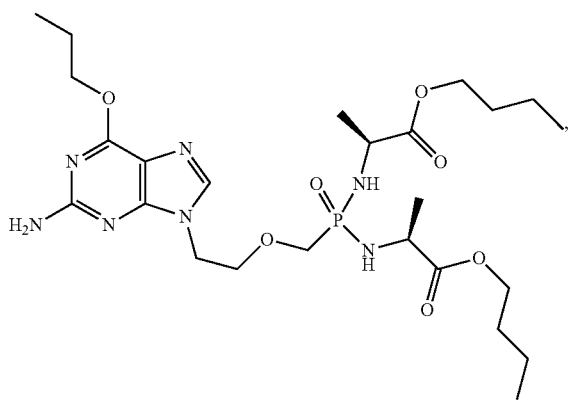
(13)
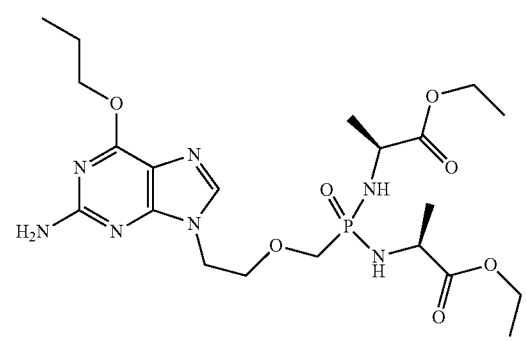
(14)
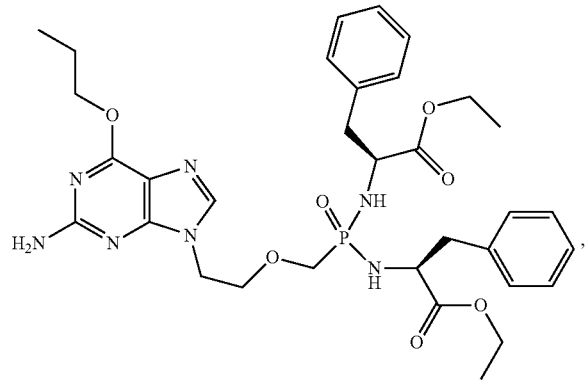
(15)
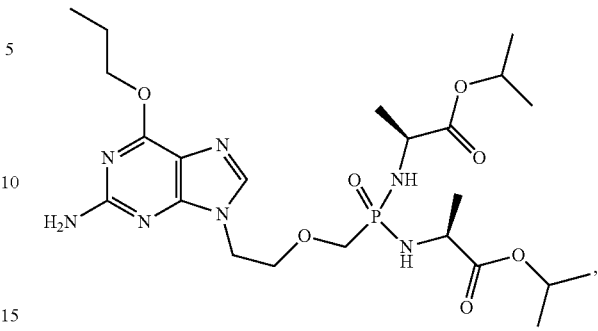
(16)
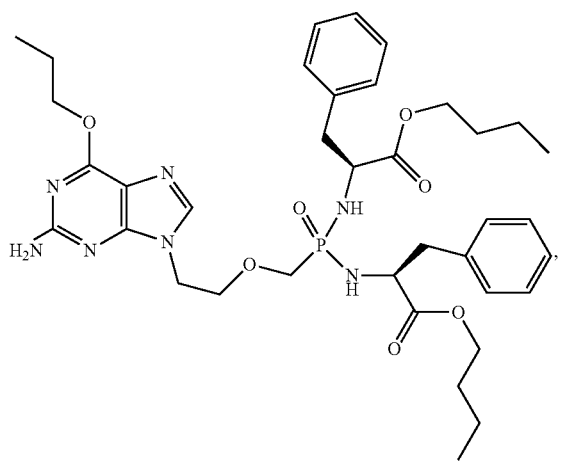
(17)
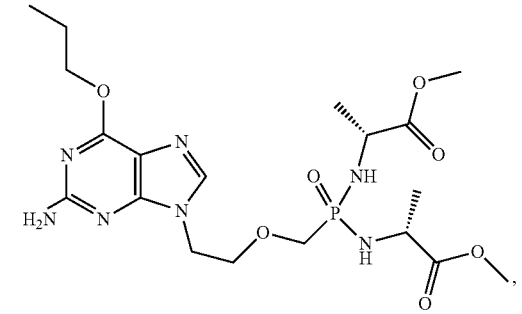
(18)
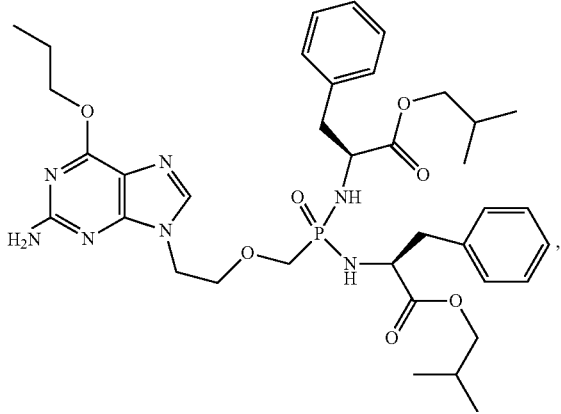
(19)

69
-continued
(20)
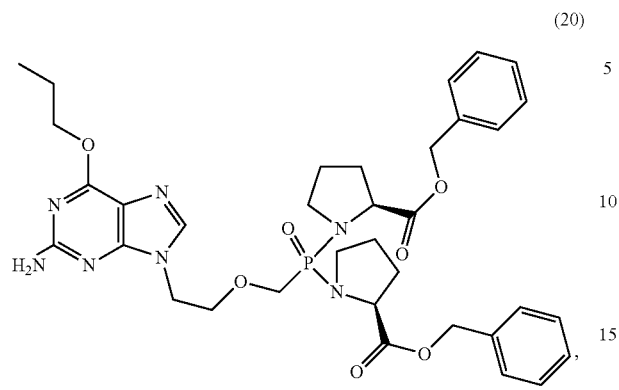
(21)
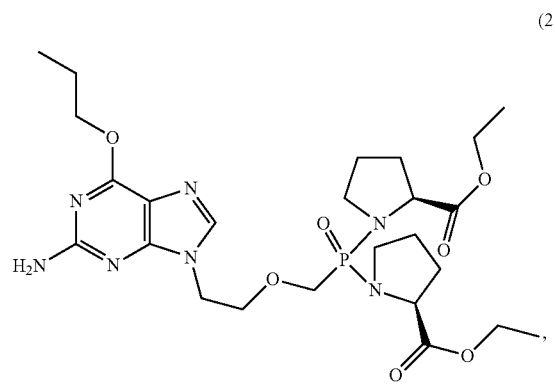
(22)
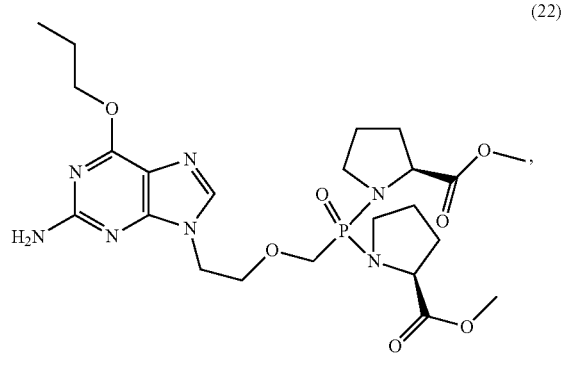
(23)
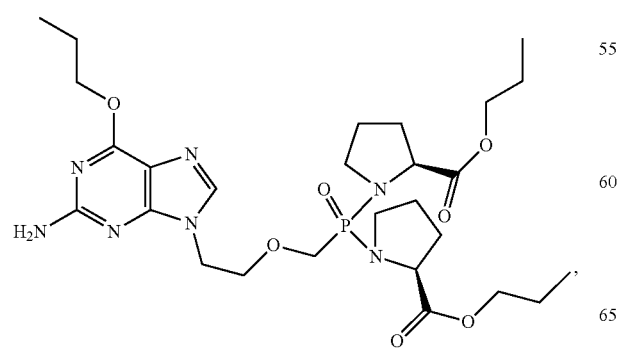
70
-continued
(24)
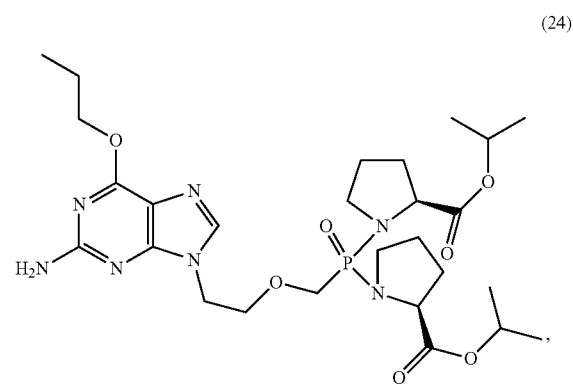
(25)
(26)
(27)
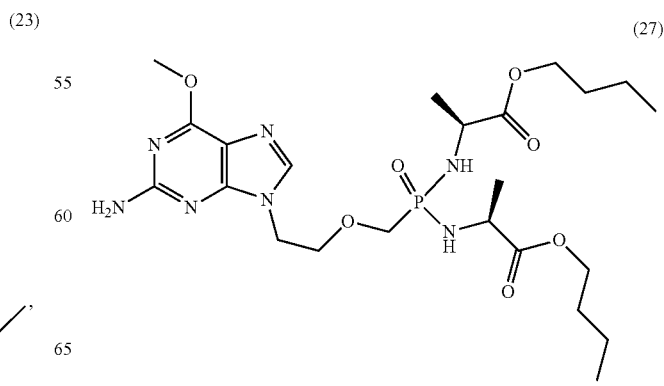

(28) 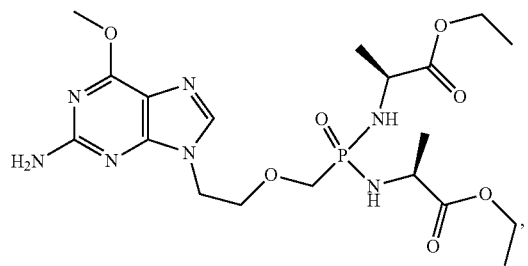
(29) 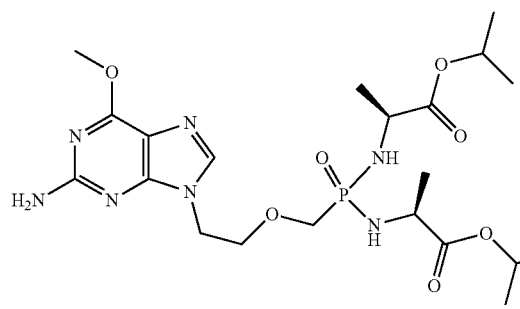
(30) 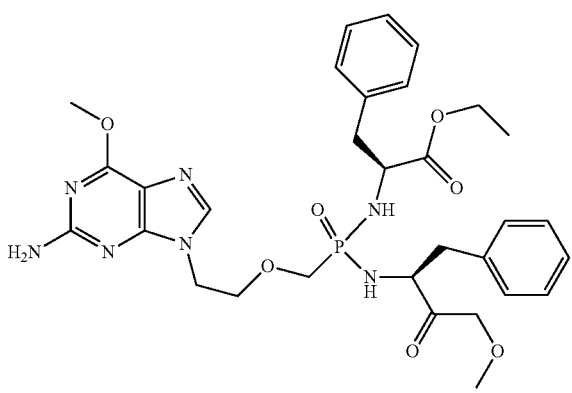
(31) 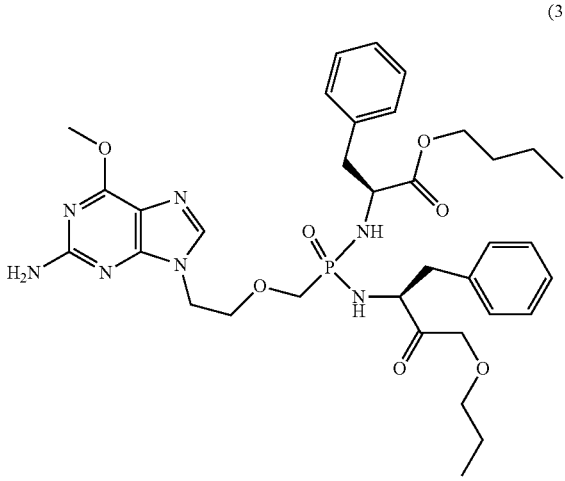
(32) 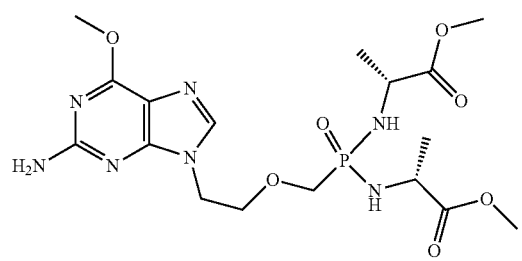
(33) 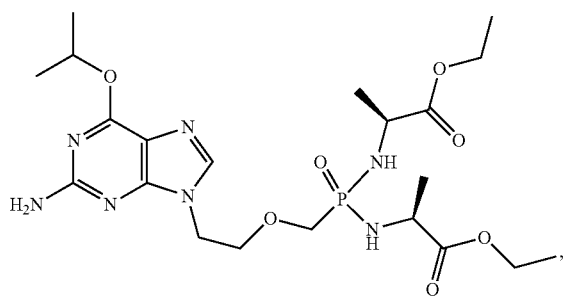
(34) 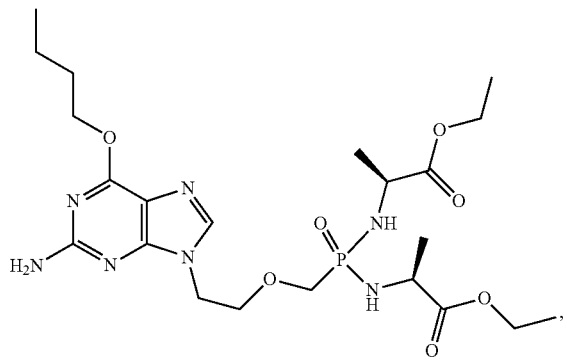
(35) 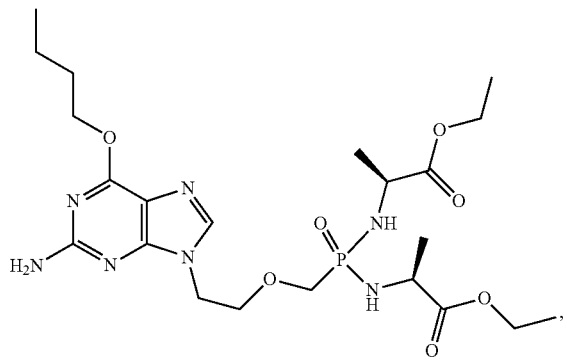

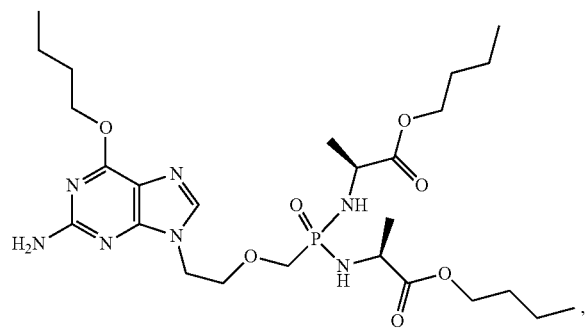
(36)
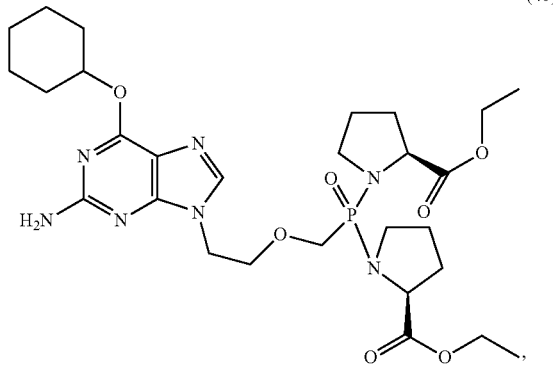
(40)
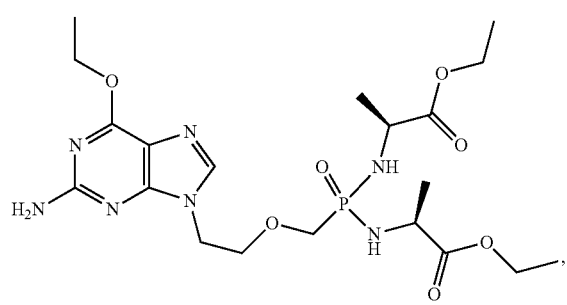
(37)
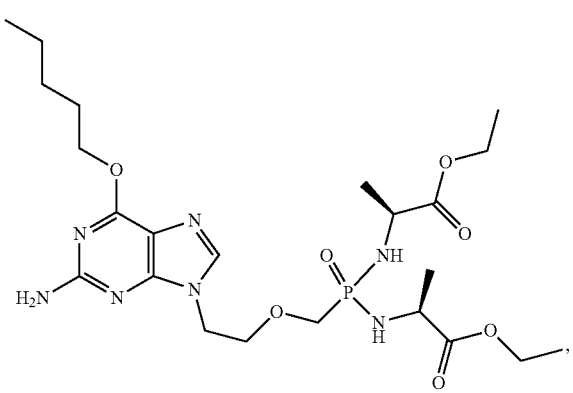
(41)
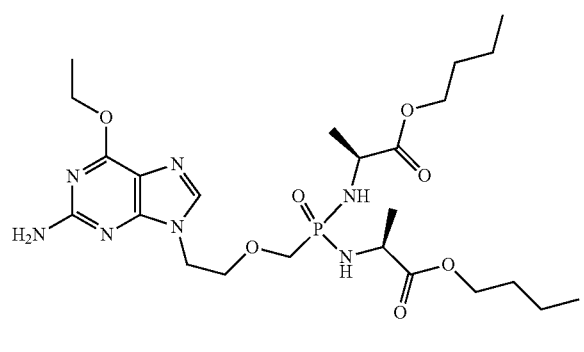
(38)
(39)
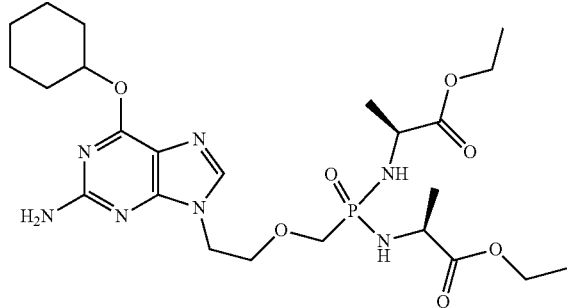
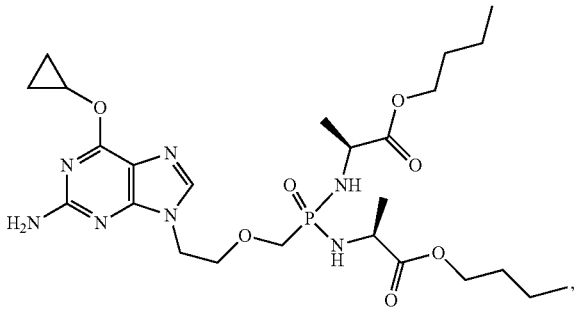
(42)
(43)

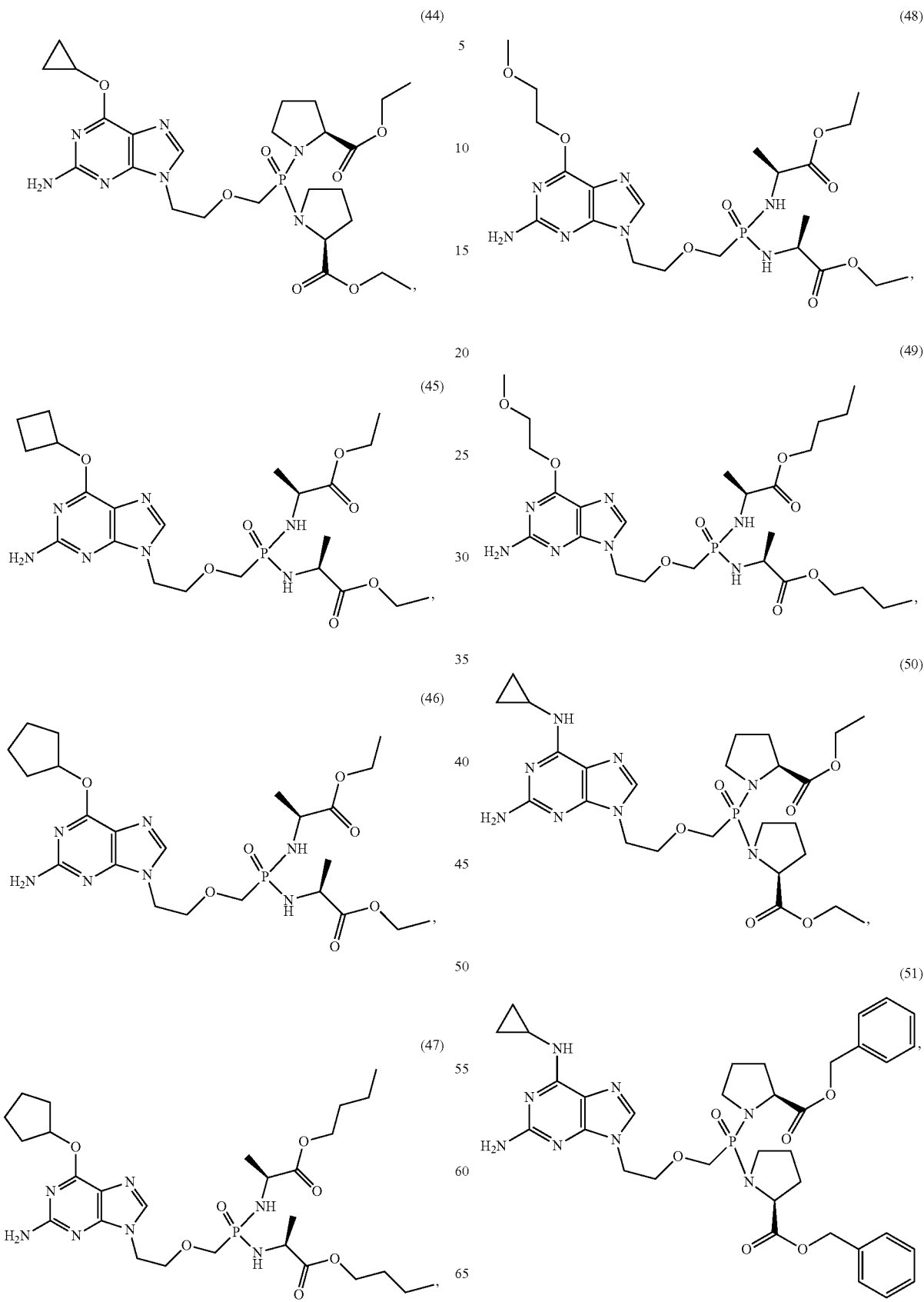

77
-continued
(52)
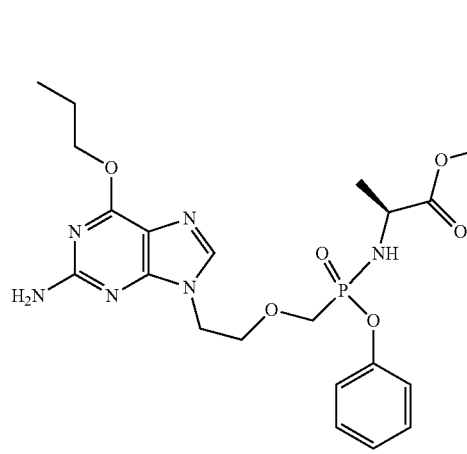
(53)
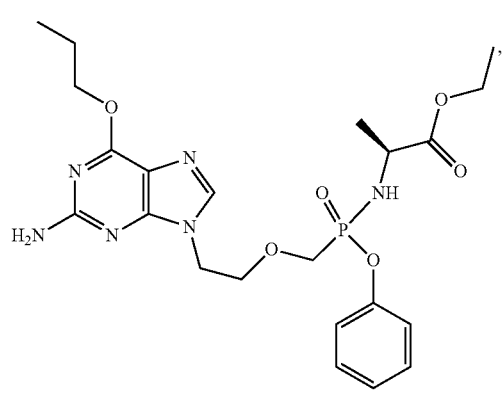
(54)
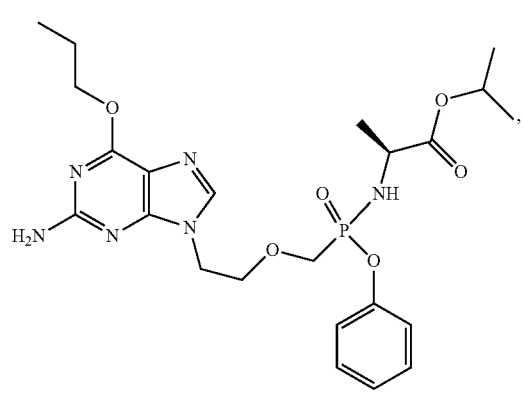
(55)
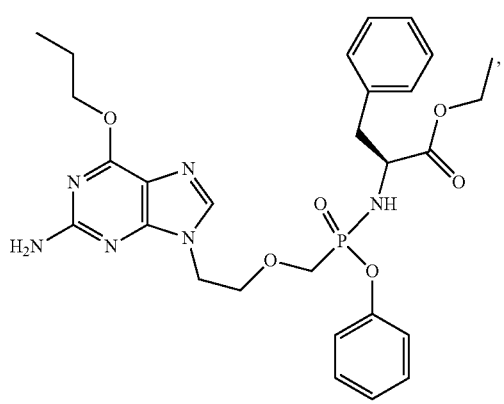
78
-continued
(56)
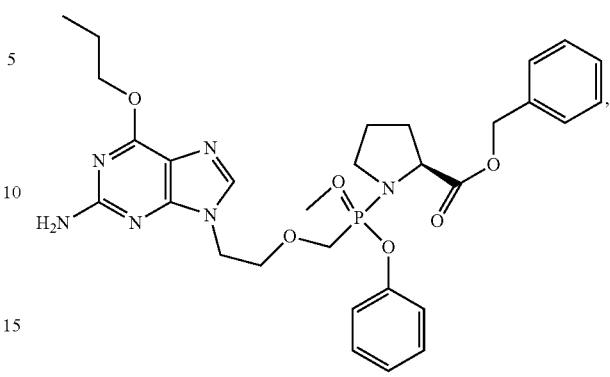
(57)
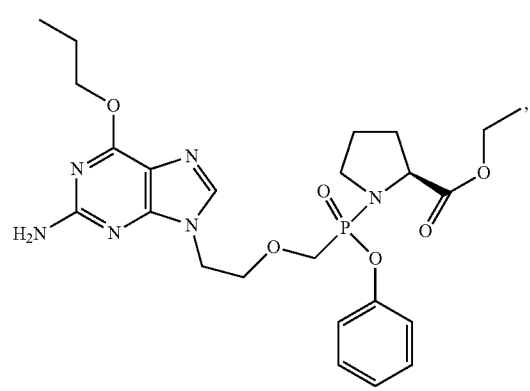
(58)
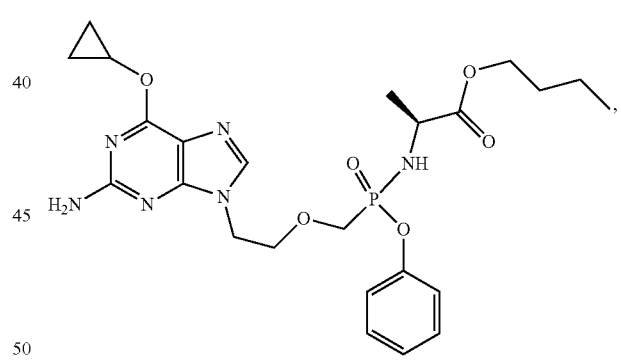
(59)
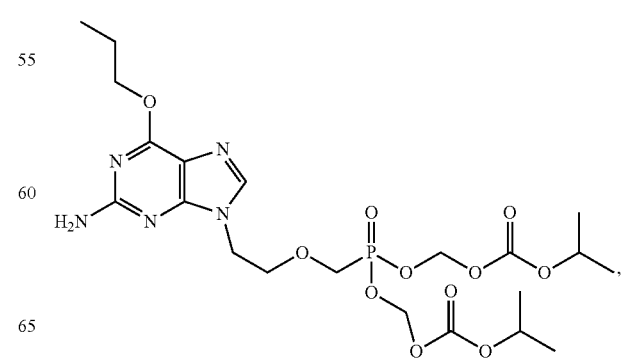

(60)

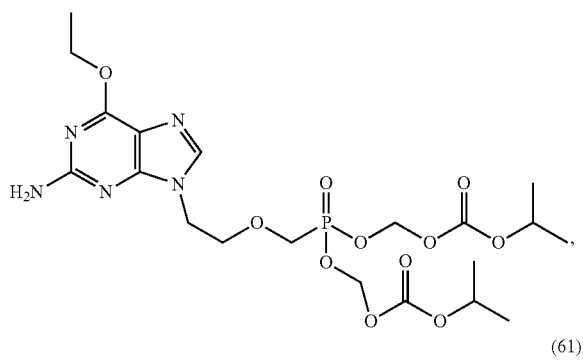

(61)

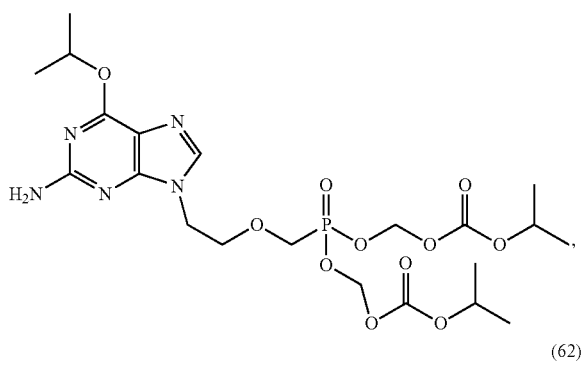

(62)

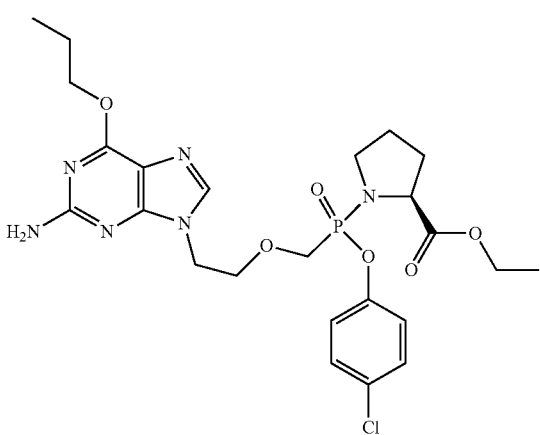

(63)

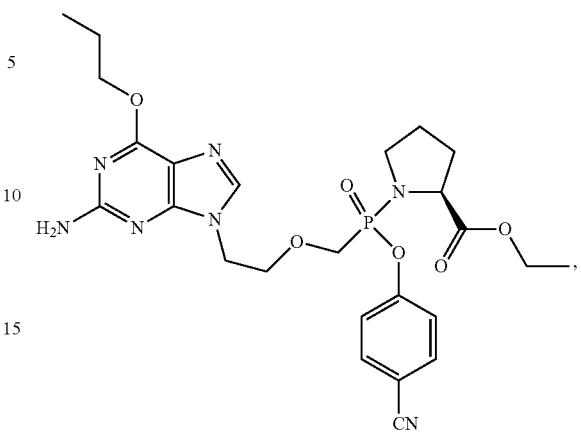

or a pharmaceutically acceptable salt, or enriched optical isomer thereof.

5. A pharmaceutical composition comprising a therapeutically effective amount of the compound according to claim 1 and a carrier.

6. A pharmaceutical composition comprising a therapeutically effective amount of the compound according to claim 2 and a carrier.

7. A pharmaceutical composition comprising a therapeutically effective amount of the compound according to claim 3 and a carrier.

8. A pharmaceutical composition comprising a therapeutically effective amount of the compound according to claim 4 and a carrier.

9. A pharmaceutical composition comprising a therapeutically effective amount of the compound according to claim 3 and a second therapeutic agent selected from an anti-viral agent or an anti-tumor/cancer agent.

10. A pharmaceutical composition comprising a therapeutically effective amount of the compound according to claim 4 and a second therapeutic agent selected from an anti-viral agent or an anti-tumor/cancer agent.

* * * * *